US010513525B2

(12) United States Patent
Du Bois et al.

(10) Patent No.: US 10,513,525 B2
(45) **Date of Patent: *Dec. 24, 2019**

(54) METHODS AND COMPOSITIONS FOR STUDYING, IMAGING, AND TREATING PAIN

(71) Applicant: THE BOARD OF TRUSTEES OF THE LELAND STANFORD JUNIOR UNIVERSITY, Palo Alto, CA (US)

(72) Inventors: Justin Du Bois, Menlo Park, CA (US); John Mulcahy, Redwood City, CA (US); Brian Andresen, Sharon, MA (US); David C. Yeomans, Sunnyvale, CA (US); Sandip Biswal, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/923,349

(22) Filed: Oct. 26, 2015

(65) Prior Publication Data

US 2016/0115173 A1 Apr. 28, 2016

Related U.S. Application Data

(63) Continuation of application No. 12/800,053, filed on May 7, 2010, now Pat. No. 9,174,999.

(60) Provisional application No. 61/176,172, filed on May 7, 2009.

(51) Int. Cl.

| | |
|---|---|
| ***A61K 31/519*** | (2006.01) |
| ***C07D 487/16*** | (2006.01) |
| ***C07D 487/14*** | (2006.01) |
| ***A61K 8/49*** | (2006.01) |
| ***A61K 49/00*** | (2006.01) |
| ***A61Q 19/02*** | (2006.01) |
| ***A61Q 19/08*** | (2006.01) |
| ***A61K 51/04*** | (2006.01) |

(52) U.S. Cl.

CPC .......... *C07D 487/16* (2013.01); *A61K 8/4953* (2013.01); *A61K 49/0002* (2013.01); *A61K 49/0004* (2013.01); *A61K 49/0032* (2013.01); *A61K 49/0052* (2013.01); *A61K 51/0459* (2013.01); *A61Q 19/02* (2013.01); *A61Q 19/08* (2013.01); *C07D 487/14* (2013.01)

(58) Field of Classification Search

CPC .................................................... C07D 487/16

See application file for complete search history.

(56) References Cited

U.S. PATENT DOCUMENTS

| | | | |
|---|---|---|---|
| 3,957,996 | A | 5/1976 | Adams et al. |
| 6,030,974 | A | 2/2000 | Schwartz et al. |
| 6,326,020 | B1 | 12/2001 | Kohane et al. |
| 7,576,202 | B2 | 8/2009 | Myasoedov et al. |
| 2002/0161013 | A1 | 10/2002 | Liu |
| 2005/0137177 | A1 | 6/2005 | Shafer |
| 2005/0202093 | A1 | 9/2005 | Kohane et al. |
| 2006/0057647 | A1 | 3/2006 | Robillot |
| 2007/0280970 | A1 | 12/2007 | Wilson |
| 2008/0021051 | A1 | 1/2008 | Wilson |
| 2008/0045553 | A1 | 2/2008 | Wilson |

FOREIGN PATENT DOCUMENTS

| | | | |
|---|---|---|---|
| CN | 1192903 | * | 9/1998 |
| CN | 1363275 | * | 8/2002 |
| EP | 0857972 | | 8/1998 |
| WO | 2003006507 A1 | | 1/2003 |
| WO | 2004072640 A1 | | 8/2004 |
| WO | 2010027641 A1 | | 3/2010 |

OTHER PUBLICATIONS

Watanae et al, Bioconjugate Chem, vol. 17, p. 459-465 (Year: 2006).*
Machine translation of Chinese Patent CN1363275, Zhou, p. 1-16 (Year: 2002).*
PAN, machine translation of CN1192903, p. 1-21. (Year: 1998).*
Tanino (1977) J. Am. Chem. Soc. 99:2818-2819.
Shimizu et al. (1981) J. Am. Chem. Soc. 103:605-609.
Koehn et al. (1982) "Dinoflagellate neurotoxins related to saxitoxin: structure and latent active of toxins B1 and B2" 23:2247-2248.
Harada et al. (1983) Agric. Biol. Chem. 47:191-193.
Hall et al. (1984) Tet. Lett. 25:3537-3538.
Jacobi et al. (1984) J. Am. Chem. Soc. 106:5594-5598.
Shimizu et al. (1984) Tetrahedron 40:539-544.
Shimuzu et al. (1986) Pure and Applied Chem. 58:2:257-262.
Arakawa et al. (1994) Toxicon 32:175-183.

(Continued)

*Primary Examiner* — Karen Cheng
(74) *Attorney, Agent, or Firm* — David A. Roise; VLP Law Group LLP

(57) ABSTRACT

Saxitoxin analogue compounds, compositions, pharmaceutical compositions, methods of synthesis of saxitoxin analogues, methods of imaging, methods of treatment, including methods of treating pain, are provided. Saxitoxin (STX), gonyautoxin (GTX), and zetekitoxin, and variant STX compounds bind to sodium channels and are effective to reduce or block flow of sodium ions through such channels. Such channel block affects nerve and muscle action, and may be effective to reduce or block pain sensations, relax muscles, reduce muscle spasm, and reduce wrinkles. STX analogue binding to sodium channels may also be useful to locate, image, or mark sodium channels, and so be useful in studying sodium channels and sodium channel disorders, and in the diagnosis and treatment of patients suffering from sodium channel disorders. In embodiments, the variant STX compounds include conjugates having increased serum half-life as compared to STX when administered to a subject. Also provided are methods for alleviating pain in a subject in need of treatment.

8 Claims, 12 Drawing Sheets

(56) References Cited

OTHER PUBLICATIONS

Arakawa et al. (1995) Toxicon 33:1577-1584.
Strichartz et al. (1995) Toxicon 33:723-737.
Schlager et al. (1996) Med. Defense Bioscience Proc. 3:1590-1597.
Onodera et al. (1997) Natural Toxins 5:146-151.
Zaman et al. (1998) Toxicon 36:627-630.
Sato et al. (2000) Bioorganic & Medicinal Chemistry Letters 10:6:1787-1789.
Anderson et al. (2003) Mol. Cancer Ther. 2:1149-1154.
Negri et al. (2003) Chem. Res. Toxicol. 16:1029-1033.
Yotsu-Yamashita et al. (2004) PNAS 101:4346-4351.
Cox et al. (2006) Nature 444:894-898.
Fleming et al. (2006) J. Am. Chem. Soc. 128:3926-3927.
Llewellyn (2006) Nat. Prod. Rep. 23:200-222.
Waxman (2006) Nature 444:831-832.
Biswal et al. (2007) Radiology 244:651-671.
Dib-Hajj et al. (2007) Trends Neurosci. 30:555-563.
Fleming et al. (2007) J. Am. Chem. Soc. 129:9964-9975.
Goldberg et al. (2007) Clinical Genetics 71:311-319.
Dell'Aversano et al. (2008) J. Nat. Prod. 71:1518-1523.
Mulcahy et al. (2008) J. Am. Chem. Soc. 130:12630-12631.
Iwamoto et al. (2009) Chem. Asian J. 4:277-285.
Robillot et al. (2009) Toxicon 53:460-465.
Mao et al. (2010) Med. Chem. Lett. 1:135-138.
Vale (2010) Phytochem. Rev. 9:525-535.
Vale (2010) Toxicon 55:162-165.
Dorr et al. (2011) J. American Society Mass. Spec. 22:2011-2020.
International Search Report and Written Opinion dated Jan. 25, 2011 for application PCT/US2010/034035.
Walls et al (2012) Bioorg. Med. Chem. 20:5269-5276.
European Supplemental Search Report dated Jan. 16, 2013 in European Patent Application No. 10772881.8.
Biotinylation web site (http://www.piercenet.com/browse.cfm.fldlD=84EBE112-F871-4CA5-807F-47327153CFCB retrieved Apr. 5, 2012).
Bundgaard, Design of Prodrugs, 1985, Elsevier, Chapter 1, p. 1-4.
Han, Targeted Prodrug Design to Optimize Drug Deliver, 2000, AAPS Pharmsci, vol. 2(1), p. 1-11.

* cited by examiner saxitoxins:

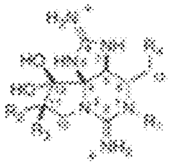

| | STX | NEO | dcSTX | dcNEO | doSTX | 11αOH-STX | 11βOH-STX | 11,11-$(OH)_2$-STX |
|---|---|---|---|---|---|---|---|---|
| $R_1$ | H | OH | H | OH | H | H | H | H |
| $R_2$ | H | H | H | H | H | H | OH | OH |
| $R_3$ | H | H | H | H | H | OH | H | OH |
| $R_4$ | $OC(O)NH_2$ | $OC(O)NH_2$ | OH | OH | H | $OC(O)NH_2$ | $OC(O)NH_2$ | $OC(O)NH_2$ |

gonyautoxins:

| | GTX1 | GTX2 | GTX3 | GTX4 | GTX5 | GTX6 | dcGTX1 | dcGTX2 | dcGTX3 |
|---|---|---|---|---|---|---|---|---|---|
| $R_1$ | OH | H | H | OH | H | OH | OH | H | H |
| $R_2$ | H | H | $OSO_3^-$ | $OSO_3^-$ | H | H | H | H | $OSO_3^-$ |
| $R_3$ | $OSO_3^-$ | $OSO_3^-$ | H | H | H | H | $OSO_3^-$ | $OSO_3^-$ | H |
| $R_4$ | $OC(O)NH_2$ | $OC(O)NH_2$ | $OC(O)NH_2$ | $OC(O)NH_2$ | $OC(O)NHSO_3^-$ | $OC(O)NHSO_3^-$ | OH | OH | OH |

C-toxins: $R_4 = OC(O)NHSO_3^-$

| | C1 | $C_2$ | C3 | C4 |
|---|---|---|---|---|
| $R_1$ | H | H | OH | OH |
| $R_2$ | H | $OSO_3^-$ | H | $OSO_3^-$ |
| $R_3$ | $OSO_3^-$ | H | $OSO_3^-$ | H |

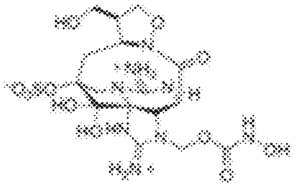

*zetekitoxin AB*

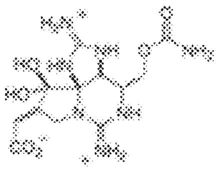

*11-saxitoxinethanoic acid*

Figure 1

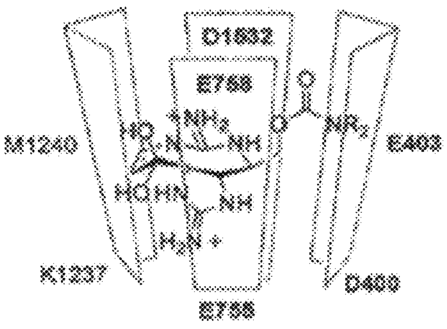

(+)-STX 1: R = H
2: R = Me

Figure 2A

Figure 2B

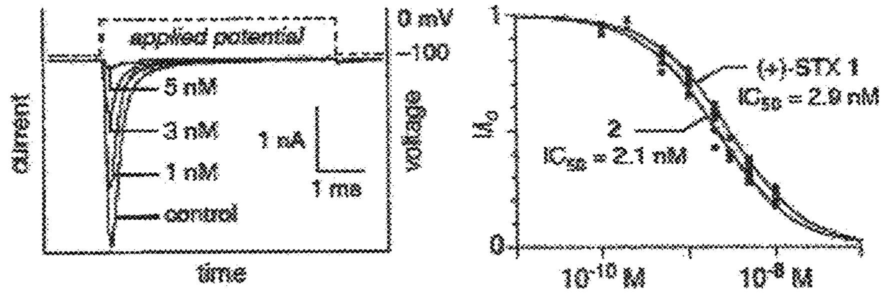
Figure 3A Figure 3B
Figure 3. Current recordings at varying concentrations of inhibitor on $rNa_V1.4$ expressed in CHO cells. Dose-response curves for (+)-STX 1 (top) and 2 (bottom).
Figure 3
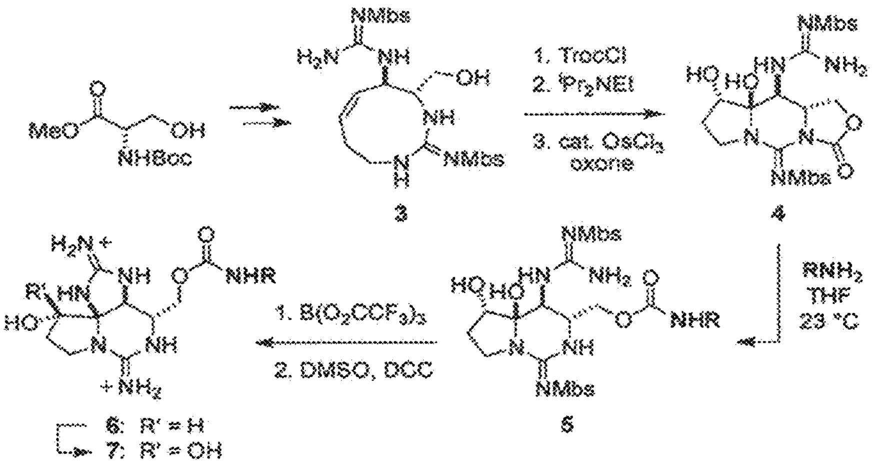
3
4
5
6: R' = H
7: R' = OH
Figure 4

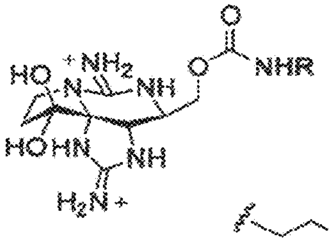
| R | | $IC_{50}$ (nM) |
| --- | --- | --- |
| $C_6H_{13}$ | 8 | 26 ± 3 |
| *i*-Pr | 9 | 83 ± 13 |
| $C_6H_{12}NH_3^+$ | 10 | 19 ± 0.8 |
| $C_5H_{10}CO_2^-$ | 11 | 135 ± 7 |
| 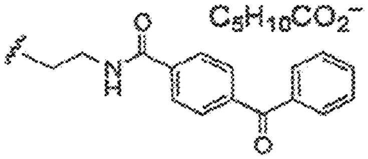 | 12 | 87 ± 9 |
Recorded $IC_{50}$ values for STX derivatives against $rNa_V1.4$.
Figure 5
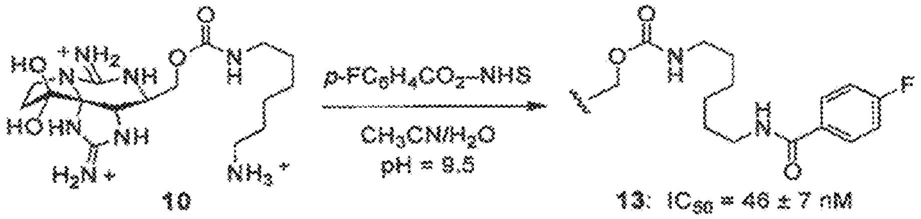
10
13: $IC_{50}$ = 46 ± 7 nM
A final-step ligation strategy for STX modification
Figure 6

(+)-STX R = H (+)-GTX 3 R = $OSO_3^-$

1

2

1

3 or

4

(+)-gonyautoxin 3

(+)-gonyautoxin 3 gonyautoxin 2

Figure 14. Measured potencies against rNa$_V$1.4 (CHO cells) for C13-modified forms of STX.

1 2 3

4a: $R_1$ = $R_2$ = Me
4b: $R_1$ = H, $R_2$ = $(CH_2)_{13}Me$

5a: $R_1$ = $R_2$ = Me
5b: $R_1$ = H, $R_2$ = $(CH_2)_{13}Me$

X = $CH_2$ or O

X = $CH_2$ or O

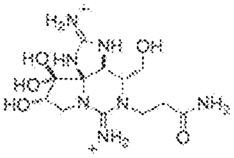
AW.1
$IC_{50}$ of ~ 4 μM against $Na_V1.4$
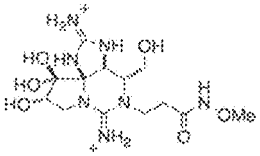
AW.2
~ 20% blockage of $Na_V1.4$ at 6 μM
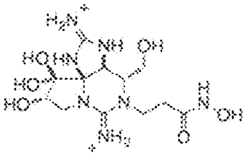
AW.3
~ 35% blockage of $Na_V1.4$ at 7 μM
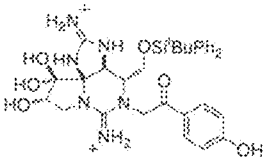
AW.4
Figure 21
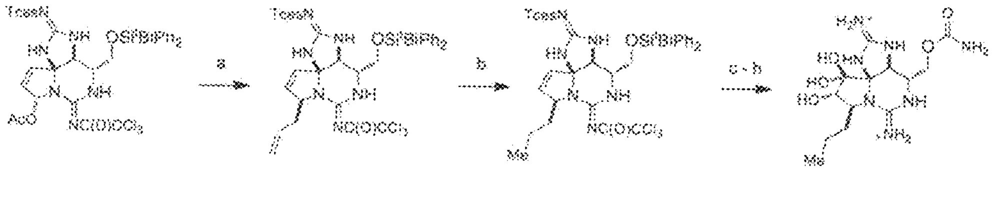
Figure 22.

METHODS AND COMPOSITIONS FOR STUDYING, IMAGING, AND TREATING PAIN

CROSS-REFERENCE TO RELATED APPLICATIONS

This application is a continuation of U.S. patent application Ser. No. 12/800,053, filed May 7, 2010, and claims the benefit under 35 U.S.C. § 119(e) of U.S. Provisional Patent Application 61/176,172 filed May 7, 2009 entitled "METHODS AND COMPOSITIONS FOR STUDYING, IMAGING, AND TREATING PAIN", the contents of which are hereby incorporated by reference in their entireties.

This application is related to PCT Application filed on May 7, 2010, having serial number PCT/US10/34035 entitled "METHODS AND COMPOSITIONS FOR STUDYING, IMAGING, AND TREATING PAIN", to Du Bois et al., the contents of which is hereby incorporated by reference in its entirety.

STATEMENT REGARDING FEDERALLY SPONSORED RESEARCH

This invention was made with Government support under Contract/Grant No. 5R01NS045684-07, awarded by the National Institutes of Health. The Government has certain rights in this invention.

BACKGROUND

The waters of the "red tide" are awash with noxious agents, the most infamous of which are the paralytic shellfish poisons (PSP) (*Seafood and Freshwater Toxins: Pharmacology, Physiology, and Detection*; Botana, L. M., Ed.; Marcel Dekker: New York, 2000.) Small molecule, bis-guanidinium structures—saxitoxin, neosaxitoxin, and the gonyautoxins—unique in both their form and function, represent the principle constituents of PSP's. (For leading reviews, see: (a) Llewellyn, L. E. *Nat. Prod. Rep.* 2006, 23, 200-222. (b) Hall, S.; Strichartz, G.; Moczydlowski, E.; Ravindran, A.; Reichardt, P. B. *ACS Symp. Series* 1990, 418, 29-65.) These highly polar, heteroatom-rich compounds are exquisitely designed corks that act to stopper ion flux through voltage-gated $Na^+$ channels ($Na_V$), thus inhibiting electrical conduction in cells. (see, e.g., *Tetrodotoxin, Saxitoxin, and the Molecular Biology of the Sodium Channel*; Eds. C. Y. Kao; S. R. Levinson; Ann. New York Acad. Sci.: New York, Vol 479, 1986; Tikhonov, D. B.; Zhorov, B. S. *Biophys. J.* 2005, 88, 184-197, and references therein.)

The intricate molecular shape common to these toxins coupled with their importance as pharmacological tools for ion channel study have inspired efforts aimed at their de novo assembly. Three prior works have described preparations of saxitoxin (STX) and one a decarbamoyloxy form. ((See, e.g., (a) Tanino, H.; Nakata, T.; Kaneko, T.; Kishi, Y. *J. Am. Chem. Soc.* 1977, 99, 2818-2819. (b) Kishi, Y. *Heterocycles* 1980, 14, 1477-1495. (c) Jacobi, P. A.; Martinelli, M. J.; Polanc, S. *J. Am. Chem. Soc.* 1984, 106, 5594-5598. (d) Martinelli, M. J.; Brownstein, A. D.; Jacobi, P. A.; Polanc, S. *Croat. Chem. Acta* 1986, 59, 267-295. (e) Fleming, J. J.; Du Bois, J. *J. Am. Chem. Soc.* 2006, 128, 3926-3927. (f) Fleming, J. J.; McReynolds, M. D.; Du Bois, J. J. Am. Chem. Soc. 2007, 129, 9964-9975. Following their earlier report, Kishi et al have described an asymmetric synthesis of (−)-decarbamoylsaxitoxin, see: Hong, C. Y.; Kishi, Y. *J. Am. Chem. Soc.* 1992, 114, 7001-7006. See also, e.g., Iwamoto, O.; Koshino, H.; Hashizume, D.; Nagasawa, K. *Angew. Chem. Int. Ed.* 2007, 46, 8625-8628.)

Pain sensations include sharp pain, dull pain, ache, and other forms of pain sensations. Pain is a sensation that may be of varying intensity and duration, and may result from a variety of causes. For example, pain may be acute, e.g., as a result of injury, illness or trauma; may be chronic, e.g., as a result of a chronic disease or condition, inflammation, cancer, or other cause; may be localized or diffuse; may be of low intensity, or of moderate intensity, or of high intensity. Thus, pain is a varied sensation, which includes, for example, acute pain, chronic pain, visceral pain, surgical pain, joint pain, bone pain, back pain, headache pain, neurogenic pain, phantom-limb pain, and other forms and experiences of pain. However, in general, whatever the intensity or duration, and whatever the cause, people prefer to lessen or eliminate the pain sensation, wherever possible.

Pain can often be alleviated by the administration of pharmaceuticals to a subject. One mechanism of alleviating pain sensation is to block the transmission of nerve signals, as, for example, by blocking conduction of nerve impulses along nerve fibers. For example, such impulses can be blocked by reducing, blocking, or altering the action of sodium channels. Sodium channels can be affected by compounds such as saxitoxin, gonyautoxin, zetekitoxin, and other molecules known as "site one sodium channel blockers" (see, e.g., Llewellyn, *Nat. Prod. Rep.* 23: 200-222 (2006)). However, as suggested by the term "toxin" in their names, such molecules may also have effects in addition to blocking pain sensation. Thus, identification of molecules which are effective to alleviate the sensation of pain, without dangerous side effects, is desired.

Chronic pain is a major, universal health problem and one of the most common reasons that people seek medical care. "Why am I in (chronic) pain?" "What's causing my pain?" or "Where is the pain coming from?" are some of the tough questions that individuals suffering from chronic pain often struggle with to get answers. The paucity of objective, diagnostic tests and a limited armamentarium of effective and safe medicines no doubt fuel the aggravation shared by chronic pain sufferers and their caregivers. Current methods used to diagnose a patient's pain are highly subjective and rely on patient self-reporting. Individuals suffering from chronic pain endure a number of tests and are often relegated to empiric analgesic testing and surgical procedures with limited objective basis for such treatments. Additionally, currently used state-of-the-art medical imaging technologies such as x-rays, computed tomography (CT), ultrasound, and conventional magnetic resonance imaging (MRI), have been inadequate in the assessment of chronic pain syndromes because they rely heavily upon anatomic abnormalities. Significant intervertebral disc abnormalities using conventional MRI, for example, can be found in 27-31% asymptomatic subjects. Additionally, the natural progression of degenerative disc disease in individuals does not correlate with development of pain symptomology, and provocative discography and MR-based morphometric measurements have only weak association with back pain episodes. More recently, meniscal tears as detected on MRI have been found to be nearly equally prevalent (~60%) in symptomatic and asymptomatic knees of middle aged and elderly persons, again, underscoring the poor relationship between MR findings and pain causation. Yet, despite such evidence to the contrary, the use of such anatomy-based imaging findings unfortunately remains an important part of the treatment algorithm for a wide range of diseases! As a result, a large number of patients are subject to unnecessary surgeries and inadequate treatments.

SUMMARY

Briefly described, embodiments of this disclosure include compounds, compositions, pharmaceutical compositions, methods of studying pain, methods of imaging pain, methods of treating pain, and the like.

In one embodiment, the present disclosure provides for a compound having structure A, B, C, or D shown below, or a pharmaceutically acceptable salt, isomer, tautomer or prodrug thereof.

In embodiments, the present disclosure provides compounds related to saxitoxin (STX), gonyautoxin (GTX), and zetekitoxin, and provides variant STX compounds. In embodiments, the variant STX compounds include conjugates having increased serum half-life as compared to STX when administered to a subject, and an increased duration of action as compared to STX when administered to a subject.

In one embodiment, the present disclosure provides for a method of treating a subject, wherein the method includes administering to the subject a compound of any one of structure A, B, C, or D shown below, or a pharmaceutically acceptable salt, isomer, tautomer or prodrug thereof, in an amount that is effective to treat pain in the subject.

In embodiments, the present disclosure provides a method for alleviating pain in a subject in need of treatment, the method comprising administering to the subject an effective amount of a compound of any one of structure A, B, C, or D shown below, or a pharmaceutically acceptable salt, isomer, tautomer or prodrug thereof, whereby pain in said subject is alleviated.

In one embodiment, the present disclosure provides for a method of treating voltage-gated sodium channel-enhanced activated pain pathways in a subject, the method including administering to the subject a compound of any one of structure A, B, C, or D shown below, or a pharmaceutically acceptable salt, isomer, tautomer or prodrug thereof, in an amount that is effective to treat pain in the subject.

In one embodiment, the present disclosure provides for a method for the preparation of a saxitoxin analogue, comprising: reacting a nine-membered ring guanidine to form a C13-Troc carbonate; closing a guanidine ring in the product of (i) in the presence of a Lewis acid; and oxidizing and deprotecting the product of (ii), whereby a saxitoxin analogue is formed.

In one embodiment, the present disclosure provides for a method for the preparation of a saxitoxin analogue, comprising: reacting 1-serine methyl ester to form an aldehyde; condensing the aldehyde of (i) with an amine; reacting the product of (ii) effective to close the ring and to provide a urea compound; reacting the product of (iii) in a process comprising allyl deprotection and isothiourea formation; and aminating the product of (iv), whereby a saxitoxin analogue is formed.

Compounds of the present disclosure are useful as analgesics, in the treatment of pain, including the alleviation of pain, reduction of the severity of pain, and in the abolition of pain and/or pain sensation in a subject.

For example they are useful in the treatment of types of pain of the following (non-limiting) list of pain to be treated: acute pain, anal fissure pain, arthritis pain, back pain, blepharospasm pain, cancer pain, chronic pain, dental pain, fibromyalgia pain, joint pain, migraine headache pain, neck pain, visceral pain, neuropathic pain, obstetric pain, post-herpetic neuralgia pain, post-operative pain, sympathetically maintained pain, shingles pain, tension headache pain, trigeminal neuralgia pain, myositis pain, musculoskeletal pain; lower back pain, pain from sprains and strains; pain associated with functional bowel disorders such as non-ulcer dyspepsia, non-cardiac chest pain and irritable bowel syndrome; pain associated with myocardial ischemia; toothache pain; and pain from dysmenorrhea.

Saxitoxin analogue compounds disclosed herein may also be useful to treat blepharospasm, cardiac arrythmia, epilepsy, focal dystonia, hyperhidrosis, muscle spasms, and urinary bladder relaxation, and to alleviate pain and discomfort associated with these disorders.

Saxitoxin analogue compounds disclosed herein may be linked to a label, an oligonucleotide, a protein, a lipid, a steroid, an antibody or an antibody fragment. A label may be, for example, selected from the group consisting of a radioisotope, a fluorescent moiety, a chemiluminescent moiety, an enzyme, an antibody, an antibody fragment, a magnetic particle, and a quantum dot.

Such linkages may be covalent linkages, or other linkages. Conjugate compounds comprising a saxitoxin analogue compound linked to a label, an oligonucleotide, a protein, an antibody or an antibody fragment may be detected in an assay and may be detected within the body of a subject to which they have been administered. Such conjugate compounds comprising a saxitoxin analogue compound linked to an oligonucleotide, a protein, a lipid, a steroid, an antibody or an antibody fragment may be directed to a desired location, organ tissue, cell, cellular compartment. For example, the oligonucleotide, protein, lipid, steroid, antibody, or antibody fragment moiety of such a conjugate compound may be effective to direct a saxitoxin analogue to a specific voltage-gated sodium channel isoform or $Na_V$-expressing cell type or to localize or anchor a saxitoxin analogue near to a voltage-gated sodium channel.

Pharmaceutical compositions comprising a saxitoxin analogue compound as disclosed herein include pharmaceutical compositions comprising a saxitoxin analogue compound as described herein, or an isomer thereof, a tautomer thereof, or a prodrug of any of the above, or a pharmaceutically acceptable salt of any of the above.

The compounds and pharmaceutical compositions described herein may be used in methods of treating a subject, the method comprising administering to the subject a saxitoxin analogue compound, or an isomer thereof, a tautomer thereof, or a prodrug of any of these, or a pharmaceutical composition or a pharmaceutically acceptable salt of any of these, in an amount that is effective to treat a disorder in the subject. The disorder may be, for example, pain. Pain disorders to be treated include, for example, acute pain, anal fissure pain, arthritis pain, back pain, blepharospasm pain, cancer pain, chronic pain, dental pain, fibromyalgia pain, joint pain, migraine headache pain, neck pain, visceral pain, neuropathic pain, obstetric pain, post-herpetic neuralgia pain, post-operative pain, sympathetically maintained pain, shingles pain, tension headache pain, trigeminal neuralgia pain, myositis pain, musculoskeletal pain; lower back pain, pain from sprains and strains; pain associated with functional bowel disorders such as non-ulcer dyspepsia, non-cardiac chest pain and irritable bowel syndrome; pain associated with myocardial ischemia; toothache pain; and pain from dysmenorrhea.

Methods of treating a subject further include methods comprising administering to the subject a saxitoxin analogue compound, or an isomer thereof, a tautomer thereof, or a prodrug of any of these, or a pharmaceutical composition or a pharmaceutically acceptable salt of any of these, in an amount that is effective to treat a voltage-gated sodium channel-enhanced ailment. In embodiments, the voltage-gated sodium channel-enhanced ailment is selected from the group consisting of acute pain, anal fissures, arthritis, back pain, chronic pain, dental pain, fibromyalgia, joint pain, migraine headaches, neck pain, neuropathic pain, obstetric pain, post-herpetic neuralgia, post-operative pain, shingles, tension headaches or trigeminal neuralgia, blepharospasm, cancer, cardiac arrythmia, epilepsy, focal dystonia, hyperhidrosis, muscle spasms, and urinary bladder relaxation.

Methods of treating a subject further include methods comprising administering to the subject a saxitoxin analogue compound, or an isomer thereof, a tautomer thereof, or a prodrug of any of these, or a pharmaceutical composition or a pharmaceutically acceptable salt of any of these, in an amount that is effective to treat a disorder selected from, for example, blepharospasm, cardiac arrythmia, epilepsy, focal dystonia, hyperhidrosis, muscle spasms, and urinary bladder relaxation, and to alleviate pain and discomfort associated with these disorders.

Further methods include method of reducing neuronal activity or effecting muscular relaxation in a subject, comprising administering to the subject a compound of any one of saxitoxin analogue, or an isomer thereof, a tautomer thereof, or a prodrug of any of these, or a pharmaceutically acceptable salt of any of these, in an amount that is effective to reduce neuronal activity in the subject or to bring about muscular relaxation in the subject.

Further methods include methods of treating a subject comprising administering to the subject a saxitoxin analogue compound, or an isomer thereof, a tautomer thereof, or a prodrug of any of these, or a pharmaceutically acceptable salt of any of these, in an amount that is effective to reduce or eliminate wrinkles.

Further methods include a method of diagnosing a subject, the method comprising administering to the subject a saxitoxin analogue compound, or an isomer thereof, a tautomer thereof, or a prodrug of any of these, or a pharmaceutically acceptable salt of any of these, in an amount that is effective to localize a voltage-gated sodium channel-enhanced ailment to a specific area in the subject's body. For example, a subject may be administered a saxitoxin analogue compound, which may be a labeled saxitoxin analogue compound, before or during an imaging procedure (e.g., before or during a CAT scan procedure, before or during a PET scan procedure, before or during an MRI procedure, and before or during a SPECT imaging session).

Also disclosed herein are synthetic methods, including methods for the preparation of a naturally occurring saxitoxin analogue as illustrated in FIG. 1 by chemical synthesis by the method illustrated in FIG. 4 or in FIG. 10. For example, methods disclosed herein include methods for preparing a gonyautoxin, as illustrated in FIG. 10.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1 illustrates structures of saxitoxin analogues as discussed herein, including saxitoxins, gonyautoxins, and zetekitoxin.

FIG. 2A illustrates saxitoxin showing its position when bound within a sodium channel.

FIG. 2B provides a further illustration showing a saxitoxin molecule in position when bound within a sodium channel.

FIG. 3A shows recordings of sodium currents in cells exposed to varying concentrations of saxitoxin (amounts shown in the figure in nanomolar (nM)).

FIG. 3B shows plots of the effects of various concentrations of saxitoxin on sodium currents in CHO cells as a function of saxitoxin concentration (top curve) and saxitoxin analogue N,N-dimethyl STX (compound 2; bottom curve).

FIG. 4 shows a synthetic scheme useful for preparing saxitoxin analogues.

FIG. 5 illustrates saxitoxin analogues and provides values for the potency of these analogues in antagonizing sodium currents ($rNa_v1.4$).

FIG. 6 illustrates a ligation strategy for modification of saxitoxin analogues.

FIG. 14A shows the reduction of sodium currents due to 0, 1 nanomolar (nM), 3 nM, and 5 nM STX.

FIG. 21 illustrates a series of N7-substituted saxitoxin analogues and notes $IC_{50}$ data, measured by sodium current blockade due to the compounds.

FIG. 22 illustrates a synthetic scheme effective to provide an n-propyl group at the R3 position, and further chemical steps to produce a C10-substituted analogue of GTX 3. Conditions: (a) allyltrimethylsilane, $BF_3OEt_2$, $CH_2Cl_2$, 70%; (b) $[Ru(Cl)_2(Ph_3P)_3]$, $H_2$, EtOH, toluene, 94%; (c) $^nBu_4NF$, THF; (d) $Cl_3CC(O)NCO$, $CH_2Cl_2$, 0° C.; then MeOH; (e) 4 mol % $OsO_4$, NMO, THF/$H_2O$; (f) PhC(O)CN, DMAP, $CH_2Cl_2$, −78° C.; (g) Dess-Martin periodinane, $CH_2Cl_2$; (h) $H_2$, Pd/C, $CF_3CO_2H$, MeOH; then $NH_3$, MeOH.

DETAILED DESCRIPTION

Figure 7:
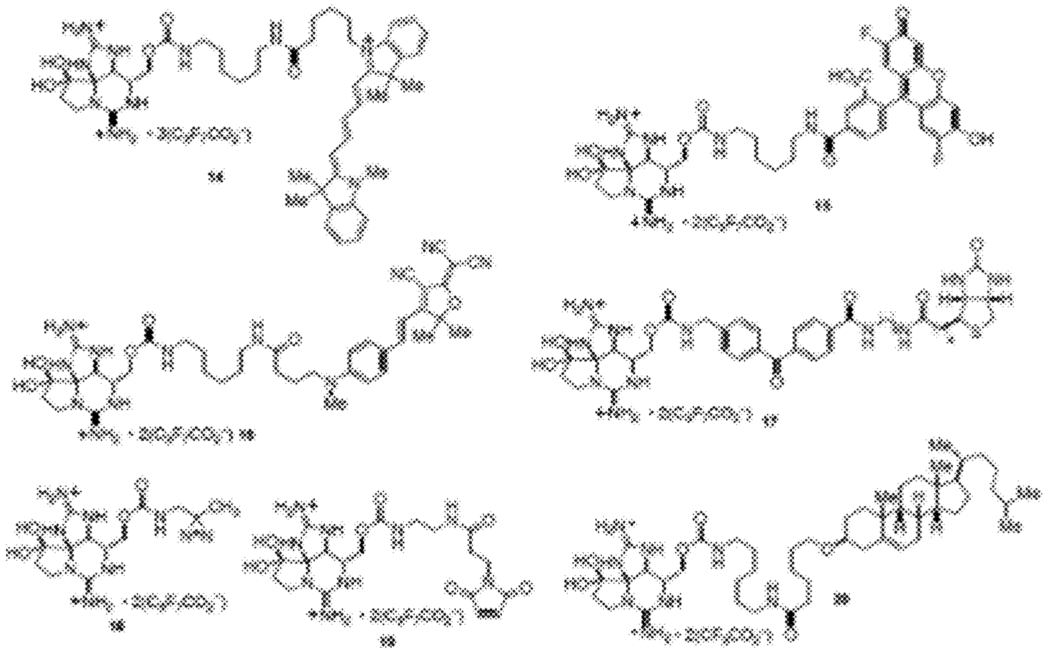
FIG. 7 illustrates examples of saxitoxin analogues modified by covalent linkages with various fluorophores (labels).

Before the present disclosure is described in greater detail, it is to be understood that this disclosure is not limited to particular embodiments described, and the embodiment of the present disclosure as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of synthetic organic chemistry, biochemistry, biology, molecular biology, recombinant DNA techniques, pharmacology, and the like, which are within the skill of the art. Such techniques are explained fully in the literature.

The examples herein are put forth so as to provide those of ordinary skill in the art with an illustrative disclosure and description of how to perform the methods and use the compounds disclosed and claimed herein. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

The term "saxitoxin analogue" includes saxitoxins, neosaxitoxins, gonyautoxins, and zetekitoxin AB and related compounds. The structures of such related compounds are discussed in more detail below, but will be understood to include the compounds of FIG. 1 and related compounds including variant compounds related to the molecules described herein. Saxitoxin analogues bind sodium channels, as discussed below. An abbreviation for "saxitoxin" is "STX." An abbreviation for gonyautoxin is "GTX."

The term "naturally occurring saxitoxin analogue" refers to saxitoxin, neosaxitoxin, a gonyautoxin and other related compounds found in nature.

Other compounds which may bind sodium channels include tetrodotoxin (TTX) and local anesthetics such as xylocaine, bupivacaine and lidocaine. Some sodium channels are "insensitive" to TTX, although most are tetrodotoxin sensitive (TTX-s).

As used herein, "pain" generally refers to the physiological and psychological sensation or perception of physical or physiological pain. "Pain," as used herein, also includes nociception, the biological experience of pain that is mediated through receptors and neurotransmitters and other aspects of the nervous system. Thus, as used herein, "imaging pain" refers to a form of visual indication of the perception of physical or physiological pain by the subject imaged. "Pain" may be specifically located to a site of injury, or may be generalized; likewise, an image of pain may visually indicate a general state of pain perception or it may specifically indicate the location of the pain or source of pain. Pain includes, without limitation, acute pain, chronic pain, visceral pain, surgical pain, joint pain, bone pain, back pain, headache pain, neurogenic pain, phantom-limb pain, and other forms of pain. Thus, pain to be treated includes, in non-limiting examples: acute pain, anal fissure pain, arthritis pain, back pain, blepharospasm pain, cancer pain, chronic pain, dental pain, fibromyalgia pain, joint pain, migraine headache pain, neck pain, visceral pain, neuropathic pain, obstetric pain, post-herpetic neuralgia pain, post-operative pain, sympathetically maintained pain, shingles pain, tension headache pain, trigeminal neuralgia pain, myositis pain, musculoskeletal pain; lower back pain, pain from sprains and strains; pain associated with functional bowel disorders such as non-ulcer dyspepsia, non-cardiac chest pain and irritable bowel syndrome; pain associated with myocardial ischemia; toothache pain; and pain from dysmenorrhea.

Saxitoxin analogue compounds disclosed herein may also be useful to treat blepharospasm, cancer, cardiac arrythmia, epilepsy, focal dystonia, hyperhidrosis, muscle spasms, and urinary bladder relaxation, and to alleviate pain and discomfort associated with these disorders.

Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

As used herein, the terms "treatment", "treating", and "treat" are defined as acting upon pain with a compound or composition of the present disclosure to reduce or ameliorate the generation of, sensation of, perception of, and/or effects of the pain and/or its symptoms. "Treatment," as used herein, covers any treatment of pain in a host (e.g., a mammal, typically a human or non-human animal of veterinary interest), and includes: (a) reducing the risk of occurrence of pain in a subject (b) impeding the initiation of pain, and (c) relieving the pain, i.e., causing regression of the pain and/or relieving one or more pain symptoms. Thus, the terms "treat," "treating," "treatment," and the like, include alleviation of pain, lessening of pain, limiting pain, reducing pain, mitigating pain, ameliorating pain, blocking pain, preventing pain, among other forms of action on pain sensation, pain perception, propagation of pain signals in the nervous system, or other action on pain.

As used herein, the terms "prophylactically treat" or "prophylactically treating" refers to completely or partially preventing pain or symptoms thereof and/or may be therapeutic in terms of a partial or complete relief from the pain and/or adverse effect attributable to the pain.

As used herein, the term "host," "subject," or "patient," includes humans and mammals (e.g., mice, rats, pigs, cats, dogs, and horses). Typical hosts to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living host" refers to a host noted above or another organism that is alive. The term "living host" refers to the entire host or organism and not just a part excised (e.g., a liver or other organ) from the living host.

The term "isolated compound" means a compound which has been substantially separated from, or enriched relative to, other compounds with which it occurs in nature. Isolated compounds are usually at least about 80%, at least about 90% pure, at least about 98% pure, or at least about 99% pure, by weight. The present disclosure is meant to include diastereomers as well as their racemic and resolved, enantiomerically pure forms and pharmaceutically acceptable salts thereof.

The term "unit dosage form," as used herein, refers to physically discrete units suitable as unitary dosages for human and/or animal subjects, each unit containing a predetermined quantity of a compound calculated in an amount sufficient to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the host.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The terms "therapeutically effective amount" and "an effective amount" are used interchangeably herein and refer to that amount of a compound (which may be referred to as an agent, a pharmaceutical compound or a drug and included in a composition or a pharmaceutical composition) being administered that is sufficient to effect the intended application including, but not limited to, pain treatment or disease or condition treatment. For example, an effective amount of a compound will relieve to some extent one or more of the symptoms of the pain, condition, or disease being treated, and/or that amount that will prevent, to some extent, one or more of the symptoms of the pain, condition, or disease that the host being treated has or is at risk of developing. The therapeutically effective amount may vary depending upon the intended application (in vitro or in vivo), or the subject and pain, condition, or disease being treated, e.g., the weight and age of the subject, the severity of the pain, condition, or disease, the manner of administration and the like, which can readily be determined by one of ordinary skill in the art. The term also applies to a dose that will induce a particular response in target cells. The specific dose will vary depending on the particular compounds chosen, the dosing regimen to be followed, whether it is administered in combination with other compounds, timing of administration, the tissue to which it is administered, and the physical delivery system in which it is carried.

As used herein, the terms "serum half-life" and "plasma half-life" are used as understood in the art, and refer to the time taken for the amount or concentration of a substance in the serum of a subject, after administration, to fall to half the initial value. Serum half-life and plasma half-life are useful to determine or infer the duration of action of a compound, such as a pharmaceutical compound, tracer, or other compound which may be administered to a subject; a longer serum half-life, and a longer plasma half-life, indicate a longer duration of action of the compound.

As used herein, the term "duration of action" refers to the length of time, after administration, that a compound has a noticeable effect on a subject to which it has been administered. For example, where the compound has an anesthetic effect, the duration of action would include the time in which the subject experiences an anesthetic effect after administration of the compound. A compound that has a longer duration of action than a reference compound is a compound for which the action (e.g., anesthesia) is longer-lasting than the action (e.g., anesthesia) of the reference compound.

As used herein, a "sodium channel" is any of the general class of macromolecule, found in nature in biological membranes such as, e.g., nerve cell membranes. When present in natural membranes, sodium channels are sensitive to voltage differences across those membranes, and can allow the passage of sodium ions across cell membranes. Binding of some toxins can block the passage of sodium ions which would otherwise occur in the absence of the toxins. Sodium channels occur in nature in many forms (e.g., genes encoding ten unique $Na^+$ channel isoforms ($Na_V$1.1-1.9, $Na_X$ where x indicates the sodium channel subtype) have been identified in mammalian cells (Hille, B. *Ion Channels of Excitable Membranes,* 3rd Ed., Sinauer: Sunderland, Mass., 2001. Page 73-78)). Variants of sodium channels, whether genetic variants, splice variants, glycosylation variants, post-translational processing variants, or other variants, including artificial variants, are included in the term "sodium channel" as used herein.

A sodium channel in a membrane is able to pass charged ions, particularly sodium ions, and to produce "sodium currents" which may be measured by a variety of experimental techniques. The magnitude and time-course of a sodium current may be affected by external factors, including the application of drugs and toxins. STX compounds, including saxitoxin analogues as disclosed herein, may reduce the magnitude of sodium currents. Such a reduction may be termed "block" or "blockade" or other term indicating a decrease in magnitude, and may be partial or complete block of the flow of ions through the sodium channel.

Sodium channels are critical to the normal functioning of the nervous and muscular system. Block of sodium currents, such as by binding of a saxitoxin analogue to a sodium channel, can block nerve conduction, such as blocking conduction along pain fibers, along other nerve fibers, block muscular contraction, and so can affect the sensation, movement, and other physiological attributes of a subject. Blockade of pain fibers can lead to analgesia and anesthesia; block of muscular action can lead to weakness or paralysis of affected muscles, and can lead to a relaxation of affected muscles. Such relaxation may be effective to reduce or eliminate wrinkles in skin where the affected muscles include muscles near to or connected to the skin. Block of sodium currents, such as by binding of a saxitoxin analogue to a sodium channel, can affect the cardiovascular system, the gastrointestinal system, the bladder, the heart, sense organs, and other organs and organ systems. The administration of saxitoxin analogues effective to reduce or eliminate sodium channel activity in a subject, whether at a particular location, or in a tissue, organ, organ system, or systemically, is useful to treat or ameliorate diseases, disorders, and conditions which include pain, muscle spasm, epilepsy, blepharospasm, focal dystonia, hyperhidrosis, and urinary bladder relaxation, cardiac disorders and conditions including cardiac arrythmia, digestive tract disorders and conditions, sensory disorders and conditions, cancer, skin conditions, other disorders and conditions as disclosed herein, and to alleviate pain and discomfort associated with these disorders.

As used herein, a "receptor" is a molecule or portion of a molecule to which a ligand binds; for example, a sodium channel acts as a receptor for STX when STX binds to the sodium channel. Different molecules may bind to a receptor with different specificity; some ligands bind to receptors with high specificity.

As used herein, the term "ligand" refers to a molecule that binds to a receptor; in embodiments, a ligand may be more mobile than a receptor to which it binds. In embodiments, a ligand may be a smaller, or a less massive, molecule than a receptor to which it binds. For example, a STX molecule is typically smaller, less massive, and more mobile under physiological conditions than a sodium channel.

As used herein, the term "receptor specificity" refers to the specificity of binding to a receptor by a particular ligand. Measurements of receptor specificity provide insight and detail regarding the pharmacokinetic properties of the interaction between a receptor and a ligand.

"Pharmaceutically acceptable salt" refers to those salts (organic or inorganic) that retain the biological effectiveness and optionally other properties of the free bases. Thus, a "pharmaceutically acceptable salt" includes any salt that is pharmaceutically acceptable and has the desired pharmacological properties. A "pharmaceutically acceptable salt" may be any salt derived from an inorganic or organic acid or an inorganic or organic base. The term "pharmaceutically acceptable anion" refers to the anion of such acid addition salts. The term "pharmaceutically acceptable cation" refers to a cation formed by addition of a base. The salt and/or the anion or cation are chosen not to be biologically or otherwise undesirable. Pharmaceutically acceptable salts can be obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like. Such salts include salts that may be derived from an inorganic or organic acid, or an inorganic or organic base, including amino acids, which is not toxic or undesirable in any way. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid).

"Pharmaceutically acceptable esters" means any ester that is pharmaceutically acceptable and has the desired pharmacological properties. Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester may be a mono-acid-mono-salt or ester or a di-salt or ester; and similarly, where there are more than two acidic groups present, some or all of such groups can be salified or esterified.

In the event that embodiments of the disclosed compounds form salts, these salts are within the scope of the present disclosure. Reference to a compound of any of the formulas herein is understood to include reference to salts thereof, unless otherwise indicated. The term "salt(s)", as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps that may be employed during preparation. Salts of the compounds of a compound may be formed, for example, by reacting the compound with an amount of acid or base, such as an equivalent amount, in a medium such as one in which the salt precipitates or in an aqueous medium followed by lyophilization.

Embodiments of the agents that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, malates (salts formed with malic acid), maleates (formed with maleic acid), ethanesulfonates (formed with ethanesulfonic acid), methanesulfonates (formed with methanesulfonic acid), 2-naphthalenesulfonates, nicotinates, nitrates, oxalates, pectinates, persulfates, 3-phenylpropionates, phosphates (formed with phosphoric acid), picrates, pivalates, propionates, salicylates, succinates, sulfates (such as those formed with sulfuric acid), sulfonates (such as those mentioned herein including those formed with p-toluenesulfonic acid), tartrates, thiocyanates, toluenesulfonates such as tosylates, undecanoates, and the like.

In embodiments having features of the present disclosure, saxitoxin analogues may include or form salts including chloride, acetate, ascorbates, aspartates, benzoates, benzenesulfonates, bisulfates, borates, gluconates, citrate, sulfate, tartrate and toluenesulfonate.

Embodiments of the compounds that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with compounds such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Solvates of the compounds of the disclosure are also contemplated herein.

In an embodiment, the compounds of the present disclosure may possess one or more chiral centers, and can therefore be produced as individual stereoisomers or as mixtures of stereoisomers, depending on whether individual stereoisomers or mixtures of stereoisomers of the starting materials are used. Unless indicated otherwise, the description or naming of a compound or groups of compounds is intended to include both the individual isomers or mixtures (racemic or otherwise) of stereoisomers. Methods for the determination of stereochemistry and the separation of stereoisomers are well known to a person of ordinary skill in the art [see the discussion in Chapter 4 of March J.: Advanced Organic Chemistry, 4th ed. John Wiley and Sons, New York, N.Y., 1992].

To the extent that the disclosed active compounds, and salts thereof, may exist in their tautomeric form, all such tautomeric forms are contemplated herein as part of the present disclosure.

All stereoisomers of the compounds, such as those that may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of a compound that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N. J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11:345-365; Gaignault et al. (1996). Designing Prodrugs and Bioprecursors I. Carrier Prodrugs, Pract. Med. Chem. 671-696; M. Asgharnejad (2000) Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3): 183-209; Browne (1997). Fosphenytoin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab., 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

As used herein, the term "substituted" preferably refers to substitution with the named substituent or substituents, multiple degrees of substitution being allowed unless otherwise stated.

As used herein, the term "optionally" means that the subsequently described event(s) may or may not occur, and includes both event(s), which occur, and events that do not occur.

As used herein, the term "derivative" and its grammatical variants preferably refers to any chemical derivative of a compound of the present disclosure, for example, an ester or an amide, and preferably a pharmaceutically functional compound which upon administration to a mammal is capable of providing (directly or indirectly) a compound of the present disclosure or an active metabolite thereof. Such derivatives are clear to those skilled in the art, without undue experimentation, and with reference to the teaching of *Burger's Medicinal Chemistry And Drug Discovery, 5th Edition*, Vol 1: Principles and Practice, which is incorporated herein by reference to the extent that it teaches physiologically functional derivatives. Such derivatives include so-called prodrug-compounds, for example compounds according to the present disclosure that are derivatized with alkyl groups, acyl groups, sugars or peptides, such as oligopeptides, and that are easily degraded or metabolized to the active compounds according to the present disclosure. Such derivatives include biodegradable polymer derivatives of the compounds according to the present disclosure. Suitable polymers and methods for producing biodegradable polymeric derivatives are known in the art, for example from Int. J. Pharm. 115, 61-67 (1995).

As used herein, the term "lipid" is used as it is understood in the art, and refers to the broad class of chemical compounds that includes, without limitation, for example, sterols, monoglycerides, diglycerides, triglycerides, phospholipids, sphingolipids, polyketides, fats, and waxes.

As used herein, the term "steroid" is used as it is understood in the art, and refers to the broad class of chemicals, of which cholesterol is an exemplary member, which include a sterane core of comprising four fused rings (three cyclohexane rings and a cyclopentane ring), and includes compounds with varying amounts of oxidation of the ring structures and includes compounds with all possible substituents on the ring structures.

The term "administration" refers to introducing a compound of the present disclosure into a host. One preferred route of administration of the agents is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

The term "aliphatic group" refers to a saturated or unsaturated linear or branched hydrocarbon group and encompasses alkyl, alkenyl, and alkynyl groups, for example.

The terms "alk" or "alkyl" refer to straight or branched chain hydrocarbon groups having 1 to 24 carbon atoms, or having 1 to 12 carbon atoms, or having 2 to 5 carbon atoms, or having 6 to 18 carbon atoms, or preferably having 2 to 12 carbon atoms, such as methyl, ethyl, n-propyl, i-propyl, n-butyl, i-butyl, t-butyl, pentyl, hexyl, heptyl, n-octyl, dodecyl, octadecyl, amyl, 2-ethylhexyl, and the like. An alkyl group is optionally substituted, unless stated otherwise, with one or more groups, selected from aryl (optionally substituted), heterocyclo (optionally substituted), carbocyclo (optionally substituted), halo, hydroxy, protected hydroxy, alkoxy (e.g., $C_1$ to $C_7$) (optionally substituted), acyl (e.g., $C_1$ to $C_7$), aryloxy (e.g., $C_1$ to $C_7$) (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted)amino, protected amino, amido, carbamate, lactam, urea, urethane, sulfonyl, etc.

The term "alkenyl" refers to straight or branched chain hydrocarbon groups having 2 to 12 carbon atoms, or having 2 to 4 carbon atoms, or having 2 to 5 carbon atoms, or having 6 to 18 carbon atoms, or preferably having 2 to 12 carbon atoms, and at least one double carbon to carbon bond (either cis or trans), such as ethenyl. An alkenyl group is optionally substituted, unless stated otherwise, with one or more groups, selected from aryl (including substituted aryl), heterocyclo (including substituted heterocyclo), carbocyclo (including substituted carbocyclo), halo, hydroxy, alkoxy (optionally substituted), aryloxy (optionally substituted), alkylester (optionally substituted), arylester (optionally substituted), alkanoyl (optionally substituted), aroyl (optionally substituted), cyano, nitro, amino, substituted amino, amido, carbamate, lactam, urea, urethane, sulfonyl, and the like.

The term "alkynyl" refers to straight or branched chain hydrocarbon groups having 2 to 12 carbon atoms, or having 2 to 4 carbon atoms, or having 2 to 5 carbon atoms, or having 6 to 18 carbon atoms, or preferably having 2 to 12 carbon atoms, and at least one triple carbon to carbon bond, such as ethynyl. An alkynyl group is optionally substituted, unless stated otherwise, with one or more groups, selected from aryl (including substituted aryl), heterocyclo (including substituted heterocyclo), carbocyclo (including substituted carbocyclo), halo, hydroxy, alkoxy (optionally substituted), aryloxy (optionally substituted), alkylester (optionally substituted), arylester (optionally substituted), alkanoyl (optionally substituted), aroyl (optionally substituted), cyano, nitro, amino, substituted amino, amido, carbamate, lactam, urea, urethane, sulfonyl, and the like.

The term "alkoxy" refers to an alkyl group linked to oxygen thus: R—O—. In this function, R represents the alkyl group. An example would be the methoxy group $CH_3O$—.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carbamate, carboxyl, etc. Thus, "alkyl group" includes ethers, esters, haloalkyls, nitroalkyls, carboxyalkyls, hydroxyalkyls, sulfoalkyls, etc.

"Cyano" refers to a —CN functional group.

The terms "halo" and "halogen" refer to the fluoro, chloro, bromo or iodo groups. There can be one or more halogen, which are the same or different.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" refers to a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like. A cycloalkyl group is optionally substituted, unless stated otherwise, with one or more groups, selected from aryl (including substituted aryl), heterocyclo (including substituted heterocyclo), carbocyclo (including substituted carbocyclo), halo, hydroxy, protected hydroxy, alkoxy (e.g., $C_1$ to $C_7$) (optionally substituted), acyl (e.g., $C_1$ to $C_7$), aryloxy (e.g., $C_1$ to $C_7$) (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted)amino, protected amino, amido, carbamate, lactam, urea, urethane, sulfonyl, etc.

The term "(cycloalkyl)alkyl" refers to the above-defined cycloalkyl group substituted by an above defined alkyl group. Examples of such a group include (cyclohexyl)methyl, 3-(cyclopropyl)-n-propyl, 5-(cyclopentyl)hexyl, 6-(adamantyl)hexyl, and the like. A (cycloalkyl)alkyl group is optionally substituted, unless stated otherwise, with one or more groups, selected from alkyl (including substituted alkyl), aryl (including substituted aryl), heterocyclo (including substituted heterocyclo), carbocyclo (including substituted carbocyclo), halo, hydroxy, protected hydroxy, alkoxy (e.g., $C_1$ to $C_7$) (optionally substituted), acyl (e.g., $C_1$ to $C_7$), aryloxy (e.g., $C_1$ to $C_7$) (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted)amino, protected amino, amido, carbamate, lactam, urea, urethane, sulfonyl, etc.

The term "substituted phenyl" refers to a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino or phenyl, substituted or unsubstituted, such that, for example, a biphenyl or naphthyl group results.

Examples of the term "substituted phenyl" include a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(iso-propyl)phenyl, 2, 3, or 4-ethylphenyl, 2, 3 or 4-(n-propyl)phenyl and the like; a mono or di(alkoxy)phenyl group, for example, 2,6-dimethoxyphenyl, 2, 3 or 4-(iso-propoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl) phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" refers to one of the above substituted phenyl groups attached to one of the above-described alkyl groups. The (substituted phenyl)alkyl is connected to another moiety. Examples of (substituted phenyl)alkyl include such groups as 2-phenyl-1-chloroethyl, 2-(4'-methoxyphenyl)ethyl, 4-(2',6'-dihydroxy phenyl)n-hexyl, 2-(5'-cyano-3'-methoxyphenyl)n-pentyl, 3-(2',6'-dimethylphenyl)n-propyl, 4-chloro-3-aminobenzyl, 6-(4'-methoxyphenyl)-3-carboxy(n-hexyl), 5-(4'-aminomethylphenyl)-3-(aminomethyl)n-pentyl, 5-phenyl-3-oxo-n-pent-1-yl, (4-hydroxynapth-2-yl)methyl and the like.

The terms "ar" or "aryl" refer to aromatic homocyclic (i.e., hydrocarbon) mono-, bi- or tricyclic ring-containing groups preferably having 6 to 12 members such as phenyl, naphthyl and biphenyl. An aryl group is optionally substituted, unless stated otherwise, with one or more groups, selected from alkyl (optionally substituted alkyl), alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, carbamate, lactam, urea, urethane, sulfonyl, etc. Optionally, adjacent substituents, together with the atoms to which they are bonded, form a 3- to 7-member ring.

The term "heteroaryl" refers to optionally substituted five-membered or six-membered rings that have 1 to 4 heteroatoms, such as oxygen, sulfur and/or nitrogen atoms, either alone or in conjunction with, additional nitrogen, sulfur or oxygen ring atoms. Furthermore, the above optionally substituted five-membered or six-membered rings can optionally be fused to an aromatic 5-membered or 6-membered ring system. For example, the rings can be optionally fused to an aromatic 5-membered or 6-membered ring system such as a benzene, pyridine or a triazole system.

The following ring systems are examples of the heterocyclic (whether substituted or unsubstituted) functional groups denoted by the term "heteroaryl": thienyl, furyl, pyrrolyl, imidazolyl, pyrazolyl, oxazolyl, isoxazolyl, thiazolyl, isothiazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

A heteroaryl group is optionally substituted, unless stated otherwise, with one or more groups, selected from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl (optionally, substituted), cycloalkyl (optionally substituted), (cycloalkyl)alkyl (optionally substituted), phenyl (optionally substituted), phenylalkyl (optionally substituted phenylalkyl). Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The terms "heterocycle", "heterocyclic", "heterocyclic group" or "heterocyclo" refer to fully saturated or partially unsaturated or completely unsaturated, including aromatic ("heteroaryl") or nonaromatic cyclic groups (for example, 3- to 13-member monocyclic, 7- to 17-member bicyclic, or 10- to 20-member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. A heterocyclic group attached at a nitrogen of the heterocycle is referred to as an N-attached heterocycle, and a heterocyclic group attached at a carbon of the heterocycle is referred to as a C-attached heterocycle. The rings of multi-ring heterocycles may be fused, bridged and/or joined through one or more spiro unions.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranly, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl, or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4 dioxa-8-azaspiro[4.5]decane), imidazopyridinyl (such as imidazo[1,5-a]pyridin-3-yl), triazolopyridinyl (such as 1,2,4-triazolo [4,3-a]pyridin-3-yl), and hexahydroimidazopyridinyl (such as 1,5,6,7,8,8a-hexahydroimidazo[1,5-a]pyridin-3-yl), and the like.

Exemplary tricyclic heterocyclic groups include carbazolyl, benzidolyl, phenanthrolinyl, acridinyl, phenanthridinyl, xanthenyl and the like.

An heterocyclo group is optionally substituted, unless stated otherwise, with one or more groups, selected from alkyl (including substituted alkyl), alkenyl, oxo, aryl (including substituted aryl), heterocyclo (including substituted heterocyclo), carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, etc., where optionally one or more pair of substituents together with the atoms to which they are bonded form a 3- to 7-member ring.

The term "alkanoyl" refers to an alkyl group (which may be optionally substituted as described above) linked to a carbonyl group (i.e. —C(O)-alkyl). Similarly, the term "aroyl" refers to an aryl group (which may be optionally substituted as described above) linked to a carbonyl group (i.e., —C(O)-aryl).

The term "(monosubstituted)amino" refers to an amino group with one substituent chosen from the group consisting of phenyl, substituted phenyl, alkyl (including substituted alkyl), $C_1$ to $C_4$ acyl, $C_2$ to $C_7$ alkenyl (including $C_2$ to $C_7$ substituted alkenyl), $C_2$ to $C_7$ alkynyl, $C_7$ to $C_{16}$ alkylaryl (including $C_7$ to $C_{16}$ substituted alkylaryl), and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" refers to an alkyl group as defined above, substituted at any position by a heteroaryl group, as above defined.

"Isosteres" are different atoms, molecules, or ions that have different molecular formulae but have similar or identical outer shell electron arrangements and also have similar properties (e.g., pharmacological properties (e.g., pharmacokinetic and pharmacodynamic)).

"Moiety" refers to a specific segment or functional group of a molecule. Chemical moieties are often recognized chemical entities embedded in or appended to a molecule.

As used herein, the term "R" and its related terms R1, R2, R3, etc. indicate substituents, as defined herein.

"Sulfate" refers to $SO_3^-$.

"Nitro" refers to the $—NO_2$ radical.

"Oxa" refers to the —O— radical.

"Oxo" refers to the =O radical.

"Sulfonyl" refers to the groups: $—S(O_2)—H$, $—S(O_2)$-(alkyl), $—S(O_2)$-(cycloalkyl), $—S(O_2)$-(amino), $—S(O_2)$-(aryl), $—S(O_2)$-(heteroaryl), and $—S(O_2)$-(heterocycloalkyl). "Sulfonamidyl" or "sulfonamido" refers to a $—S(=O)_2—NRR$ radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the $—S(=O)_2—NRR$ radical may be taken together with the nitrogen to which it is attached to form a 4-, 5-, 6-, or 7-membered ring ($—S(O_2)$-(heterocycloalkyl). In some embodiments, it is a $C_1$-$C_{10}$ sulfonamido, wherein each R in sulfonamido contains 1 carbon, 2 carbons, 3 carbons, or 4 carbons total. A sulfonamido group is optionally substituted by one or more of the substituents described herein for alkyl, cycloalkyl, aryl, heteroaryl, respectively. A "sulfone" refers to a $—S(O_2)$-(alkyl), $—S(O_2)$-(aryl), $—S(O_2)$-(heteroaryl), or $—S(O_2)$-(heterocycloalkyl) (when the sulfone group is attached to a carbon atom in the heterocycloalkyl). A sulfonamido group is optionally substituted by one or more of the substituents described herein for alkyl, cycloalkyl, aryl, heteroaryl, respectively.

As used herein, "label" and grammatical variants thereof refers to a detectable compound or composition which is conjugated directly or indirectly to another compound, such as, e.g., a saxitoxin analogue, so as to generate a "labeled" compound. The label comprises a detectable moiety. The detectable moiety may be capable of producing, either directly or indirectly, a detectable signal. The label may be detectable by itself (e.g. radioisotope labels or fluorescent labels) or, in the case of an enzymatic label, may catalyze chemical alteration of a substrate compound or composition which is detectable.

A compound can be directly or indirectly conjugated to a label which provides a detectable signal, e.g. radioisotope, fluorescers, enzyme, antibodies, particles such as magnetic particles, chemiluminescers, quantum dots, or specific binding molecules, etc. Preferred labels include, but are not limited to, fluorescent labels, label enzymes and radioisotopes. Suitable labels include, for example, fluorescent or chemiluminescent compounds, such as luciferin, fluorescein isothiocyanate, rhodamine, tetramethylrhodamine, eosin, erythrosin, coumarin, methyl-coumarins, pyrene, Malacite green, stilbene, Lucifer Yellow, CASCADE BLUE®, TEXAS RED®, IAEDANS, EDANS, BODIPY FL, LC Red 640, Cy 5, Cy 5.5, LC Red 705 and OREGON GREEN™. Suitable optical dyes are described in the 1996 Molecular Probes Handbook by Richard P. Haugland, hereby expressly incorporated by reference.

Suitable labels also include fluorescent proteins or peptides (e.g., Green Fluorescent Protein (GFP) and GFP variants and related peptides); (GFP; Chalfie, et al., Science 263(5148):802-805 (Feb. 11, 1994); and EGFP; Clontech—Genbank Accession Number U55762), blue fluorescent protein (BFP; Quantum Biotechnologies, Inc. 1801 de Maisonneuve Blvd. West, 8th Floor, Montreal (Quebec) Canada H3H 1J9; Stauber, R. H. Biotechniques 24(3):462-471 (1998); 3. Heim, R. and Tsien, R. Y. Curr. Biol. 6:178-182 (1996)), enhanced yellow fluorescent protein (EYFP; Clontech Laboratories, Inc., 1020 East Meadow Circle, Palo Alto, Calif. 94303), luciferase (Ichiki, et al., J. Immunol. 150(12):5408-5417 (1993)), and Renilla WO 92/15673; WO 95/07463; WO 98/14605; WO 98/26277; WO 99/49019; U.S. Pat. Nos. 5,292,658; 5,418,155; 5,683,888; 5,741,668; 5,777,079; 5,804,387; 5,874,304; 5,876,995; and 5,925,558).

Suitable labels also include radioactive labels (e.g., $^{125}I$, $^{35}S$, $^{32}P$, $^{18}F$, $^{14}C$, $^{3}H$, etc.), biological labels, including specific binding molecules (e.g., biotin, streptavidin, digoxin and antidigoxin, etc.), an enzyme, such as alkaline phosphatase, β-galactosidase (Nolan, et al., Proc Natl Acad Sci USA 85(8):2603-2607 (April 1988)), or horseradish peroxidase, and other labels. All of the above-cited references are expressly incorporated herein by reference.

Any method known in the art for incorporating the detectable moiety to or into the saxitoxin analogue, or for conjugating the saxitoxin analogue to the detectable moiety may be employed, including those methods described by Hunter et al., Nature, 144:945 (1962); David et al., Biochemistry, 13:1014 (1974); Pain et al., J. Immunol. Meth., 40:219 (1981); and Nygren, J. Histochem. and Cytochem., 30:407 (1982).

As used herein the term "antibody" is used in the broadest sense and includes, for example, polyclonal antibodies, monoclonal antibodies, antibody compositions with polyepitopic specificity, single chain, and fragments of antibodies. The term "monoclonal antibody" as used herein refers to an antibody obtained from a population of substantially homogeneous antibodies, i.e., the individual antibodies comprising the population are identical except for possible naturally-occurring mutations that may be present in minor amounts.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

As used herein, the terms "antibody fragment" and grammatical variants thereof refers to molecules that comprise a portion of an intact antibody, preferably the antigen binding or variable region of the intact antibody. Examples of antibody fragments include Fab, Fab', F(ab').sub.2, and Fv fragments; diabodies; linear antibodies (Zapata et al., Protein Eng. 8(10): 1057-1062 [1995]); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an $F(ab')_2$ fragment that has two antigen-combining sites and is still capable of cross-linking antigen.

As used herein, the term "Fv" refers to the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

As used herein, the term "Fab fragment" refers to an antibody fragment that contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

As used herein, the term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

A saxitoxin analogue compound as described herein may be linked to another molecule, which other molecule may serve as a label and/or may serve to direct the saxitoxin analogue to a particular location, organ, tissue, cell, or cellular compartment. For example, an antibody or antibody fragment may be linked to a saxitoxin analogue effective to direct the saxitoxin analogue to a specific voltage-gated sodium channel isoform or $Na_V$-expressing cell type. As used herein, the term "direct" as used in the phrase "to direct the saxitoxin analogue to . . . " is used to indicate that the saxitoxin analogue may bind to, or may be placed in the proximity of, a desired location, organ, tissue, cell, or cellular compartment.

As used herein, the term "imaging" refers to the production of a representation of a subject, or of a portion of a subject, using imaging devices and methods, such as X-ray imaging, computer assisted tomography (CAT) scan imaging, positron emission tomography (PET) scan imaging, magnetic resonance imaging (MRI), single photon emission computed tomography (SPECT) imaging, and the like.

For example, PET imaging involves the creation of tomographic images of positron emitting radionuclides in a subject of interest. A radionuclide-labeled pharmaceutical, i.e., a radiopharmaceutical, is administered to an imaging subject. The subject is positioned within a PET imaging system which includes a detector ring and detection electronics. As the radionuclides decay, positively charged photons known as "positrons" are emitted. For commonly used radiopharmaceuticals such as FDG, (i.e., $^{18}$F-fluorodeoxyglucose), these positrons travel only a few millimeters through the tissues of the subject before colliding with an electron, resulting in mutual annihilation. The positron/electron annihilation results in a pair of oppositely-directed gamma rays that are emitted with approximately 511 keV energy.

It is these gamma rays that are detected by the scintillator components of the detector ring. When struck by a gamma ray, the scintillating material in these components emits light, which is detected by a photodetector component, such as a photodiode or photomultiplier tube. The signals from the photodetectors are processed as incidences of gamma rays. When two gamma rays strike oppositely positioned scintillators at approximately the same time, a coincidence is registered. Data sorting units process the coincidences to determine which are true coincidence events and sort out data representing dead times and single gamma ray detections. The coincidence events are binned and integrated to form frames of PET data which may be reconstructed as images depicting the distribution of the radionuclide-labeled pharmaceutical in the subject.

MRI is a medical imaging modality that can create pictures of the inside of a human body without using x-rays or other ionizing radiation. MRI uses a powerful magnet to create a strong, uniform, static magnetic field (i.e., the "main magnetic field"). When a human body, or part of a human body, is placed in the main magnetic field, the nuclear spins that are associated with the hydrogen nuclei in tissue water become polarized. This means that the magnetic moments that are associated with these spins become preferentially aligned along the direction of the main magnetic field, resulting in a small net tissue magnetization along that axis (the "z axis", by convention). An MRI system also comprises components called gradient coils that produce smaller amplitude, spatially varying magnetic fields when current is applied to them. Typically, gradient coils are designed to produce a magnetic field component that is aligned along the z axis and that varies linearly in amplitude with position along one of the x, y or z axes. The effect of a gradient coil is to create a small ramp on the magnetic field strength and concomitantly on the resonant frequency of the nuclear spins, along a single axis. Three gradient coils with orthogonal axes are used to "spatially encode" the MR signal by creating a signature resonance frequency at each location in the body. Radio frequency (RF) coils are used to create pulses of RF energy at or near the resonance frequency of the hydrogen nuclei. These coils are used to add energy to the nuclear spin system in a controlled fashion. As the nuclear spins then relax back to their rest energy state, they give up energy in the form of an RF signal. This signal is detected by the MRI system, and combined with multiple additional such signals may be used to reconstruct an MR image using a computer and known algorithms Discussion Embodiments of the present disclosure provide for methods and compositions for studying, imaging, and treating pain. Embodiments of the present disclosure provide for methods of preparing saxitoxin analogue compounds (e.g., saxitoxin-type compounds, neosaxitoxin-type compounds, and gonyautoxin-type compounds) that can be used to study, treat, and image pain. In particular, embodiments of the present disclosure provide for saxitoxin analogue compounds that have in vivo potency as antagonists of sodium ion channel functions. Embodiments of the present disclosure provide for the preparing of saxitoxin analogue compounds through new and novel methods. Embodiments of the methods allow for the selective modification of the structures so that designed compounds can have improved receptor specificity and/or pharmacokinetic properties. In addition, embodiments of the present disclosure provide for methods to prepare fluorescent and/or radio-labeled forms of the saxitoxin analogue compounds so that saxitoxin analogues, including gonyautoxin-type compounds, can be used to image pain and determine the location and/or the source of the pain. Furthermore, embodiments of the saxitoxin analogue compounds can be designed to display inhibitory effects on specific sodium channel isoforms.

Structure A

Embodiments of the compound include structure A, an isomer thereof, a tautomer thereof, or a prodrug of any of these, or a pharmaceutically acceptable salt of any of these.

Structure A

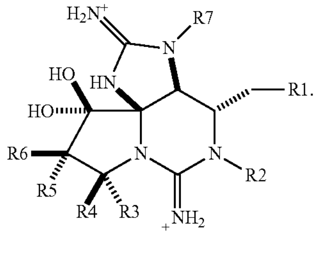

R1 can be a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl(alkyl), nitro, oxa, oxo, sulfonyl, sulfonamido, sulfone, $—OR_A$, $=O$, $—C(=O)R_A$, $—OC(=O)R_A$, $—OC(=O)OR_A$, $—OC(=O)N(R_A)_2$, $—CO_2R_A$, —CN, —SCN, $—SR_A$, $—SOR_A$, $—SO_2R_A$, $—NO_2$, $—N(R_A)_2$, $—NHC(O)R_A$, or $—C(R_A)_3$, wherein each occurrence of $R_A$ can be independently a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl (alkyl), nitro, oxa, oxo, sulfonyl, sulfonamido, or sulfone.

R2 can be a group such as hydrogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, heteroaryl(alkyl), oxa, oxo, sulfonyl, sulfonamido, sulfone, $—OR_A$, $—C(=O)R_A$, $—OC(=O)R_A$, $—OC(=O)OR_A$, $—OC(=O)N(R_A)_2$, $—CO_2R_A$, —CN, $—SO_2R_A$, $—NO_2$, —or $—C(R_A)_3$, wherein each occurrence of $R_A$ can be independently a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted) amino, protected (monosubstituted)amino, (disubstituted) amino, heteroaryl(alkyl), nitro, oxa, oxo, sulfonyl, sulfonamido, or sulfone.

R3 can be a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl(alkyl), oxa, oxo, sulfonyl, sulfonamido, sulfone, $—OR_A$, $=O$, $—C(=O)R_A$, $—OC(=O)R_A$, $—OC(=O)OR_A$, $—OC(=O)N(R_A)_2$, $—CO_2R_A$, —CN, —SCN, $—SR_A$, $—SOR_A$, $—SO_2R_A$, $—N(R_A)_2$, $—NHC(O)R_A$, or $—C(R_A)_3$, wherein each occurrence of $R_A$ can be independently a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl(alkyl), nitro, oxa, oxo, sulfonyl, sulfonamido, or sulfone.

R4 can be a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl(alkyl), oxa, oxo, sulfonyl, sulfonamido, sulfone, $—OR_A$, $=O$, $—C(=O)R_A$, $—OC(=O)R_A$, $—OC(=O)OR_A$, $—OC(=O)N(R_A)_2$, $—CO_2R_A$, —CN, —SCN, $—SR_A$, $—SOR_A$, $—SO_2R_A$, $—N(R_A)_2$, $—NHC(O)R_A$, or $—C(R_A)_3$, wherein each occurrence of $R_A$ can be independently a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl(alkyl), nitro, oxa, oxo, sulfonyl, sulfonamido, or sulfone.

R5 can be a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl(alkyl), nitro, oxa, oxo, sulfonyl, sulfate, sulfonamido, sulfone, —$OR_A$, ═O, —C(═O)$R_A$, —OC(═C)$R_A$, —OC(═O)$OR_A$, —OC(═O)$N(R_A)_2$, —$CO_2R_A$, —CN, —SCN, —$SR_A$, —$SOR_A$, —$SO_2R_A$, —$NO_2$, —$N(R_A)_2$, —NHC(O)$R_A$, or —$C(R_A)_3$, wherein each occurrence of $R_A$ can be independently a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl (alkyl), nitro, oxa, oxo, sulfonyl, sulfonamido, or sulfone.

R6 can be a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl(alkyl), nitro, oxa, oxo, sulfonyl, sulfate, sulfonamido, sulfone, —$OR_A$, ═O, —C(═O)$R_A$, —OC(═C)$R_A$, —OC(═O)$OR_A$, —OC(═O)$N(R_A)_2$, —$CO_2R_A$, —CN, —SCN, —$SR_A$, —$SOR_A$, —$SO_2R_A$, —$NO_2$, —$N(R_A)_2$, —NHC(O)$R_A$, or —$C(R_A)_3$, wherein each occurrence of $R_A$ can be independently a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl (alkyl), nitro, oxa, oxo, sulfonyl, sulfonamido, or sulfone.

R7 can be a group such as hydrogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, (substituted phenyl)alkyl, aryl, heteroaryl, heterocyclic, heterocyclo, alkanoyl, heteroaryl(alkyl), nitro, oxa, oxo, sulfonyl, sulfonamido, sulfone, —$OR_A$, ═O, —C(═O)$R_A$, —OC(═O)$R_A$, —OC(═O)$OR_A$, —OC(═O)$N(R_A)_2$, —$CO_2R_A$, —CN, —$SO_2R_A$, —$NO_2$, or —$C(R_A)_3$, wherein each occurrence of $R_A$ can be independently a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl (alkyl), nitro, oxa, oxo, sulfonyl, sulfonamido, or sulfone.

In an embodiment, R1 can be a group such as hydroxyl, alkoxyl, cyano, heteroaryl, (monosubstituted)amino, protected (monosubstituted)amino, (disubstituted)amino, —$OR_A$, ═O, —OC(═O)$R_A$, —OC(═O)$OR_A$, —OC(═O)$N(R_A)_2$, —CN, —SCN, —$SR_A$, —$SOR_A$, —$SO_2R_A$, —$NO_2$, —$N(R_A)_2$, or —NHC(O)$R_A$, wherein each occurrence of $R_A$ can be independently a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl(alkyl), nitro, oxa, oxo, sulfonyl, sulfonamido, or sulfone.

R2 can be hydrogen. R3 can be a hydrogen or n-propyl group. R4 can be a hydrogen or n-propyl group.

R5 can be a group such as hydrogen, sulfate, —$OR_A$, ═O, —OC(═O)$R_A$, —OC(═O)$OR_A$, —OC(═O)$N(R_A)_2$, wherein each occurrence of $R_A$ can be independently a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl(alkyl), nitro, oxa, oxo, sulfonyl, sulfonamido, or sulfone.

R6 can be a group such as hydrogen, sulfate, —$OR_A$, ═O, —OC(═O)$R_A$, —OC(═O)$OR_A$, —OC(═O)$N(R_A)_2$, wherein each occurrence of $R_A$ can be independently a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl(alkyl), nitro, oxa, oxo, sulfonyl, sulfonamido, or sulfone.

R7 can be a group such as hydrogen, alkoxy, alkanoyl, —$(CH_2)_2C$(═O)$R_A$, —$(CH_2)_2C$(═O)$N(R_A)_2$, wherein each occurrence of $R_A$ can be independently a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl (alkyl), nitro, oxa, oxo, sulfonyl, sulfonamido, or sulfone.

In an embodiment, R1 can be a group such as hydroxyl, —OC(═O)$NHR_A$, —OC(═O)$N(R_A)_2$ wherein each occurrence of $R_A$ can be independently a group such as hydrogen, methyl, i-propyl, tetradecyl or any of the following:

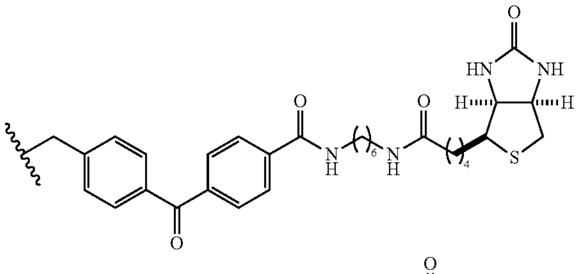

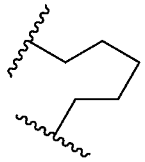

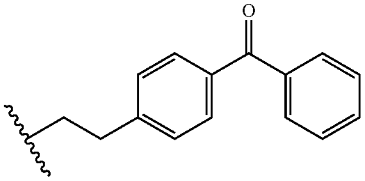

-continued
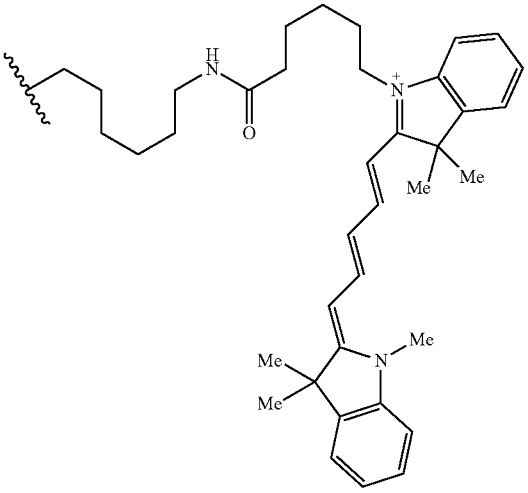
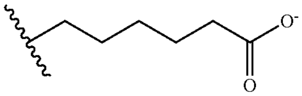
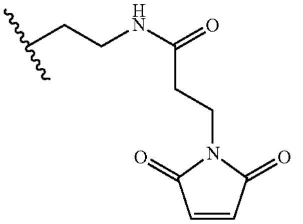
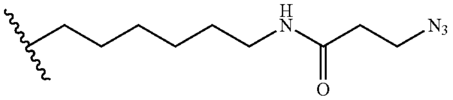
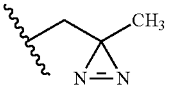
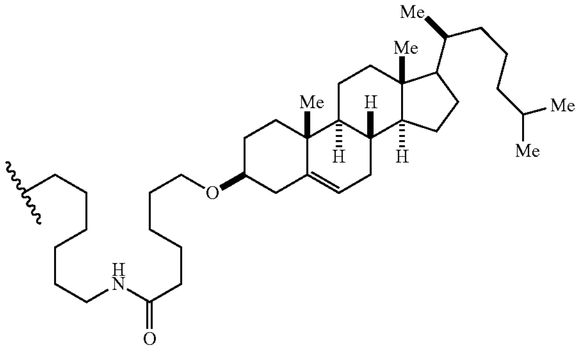
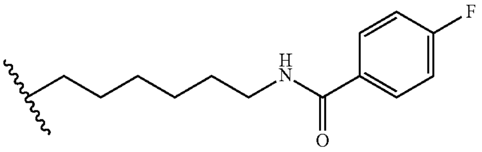
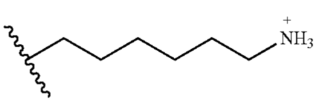
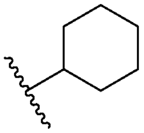
-continued
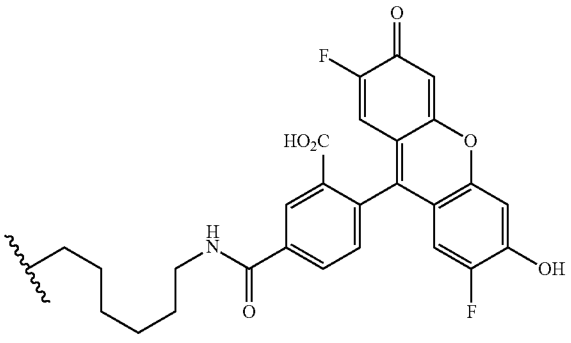
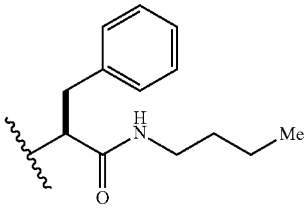
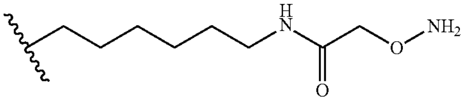
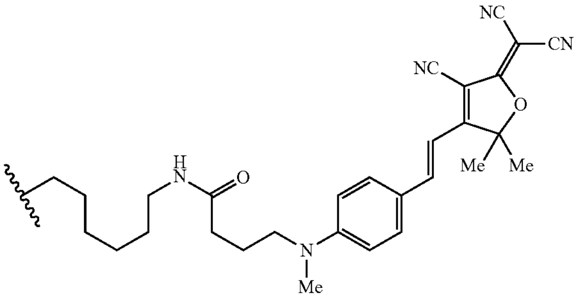
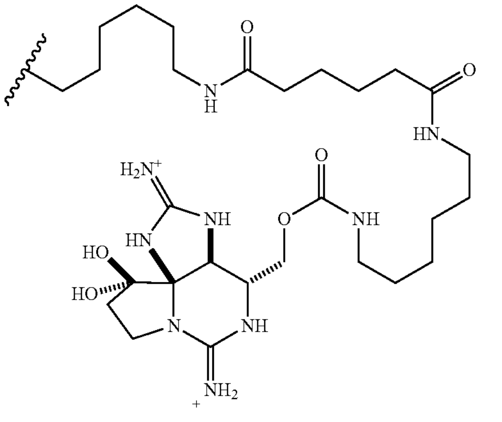

-continued

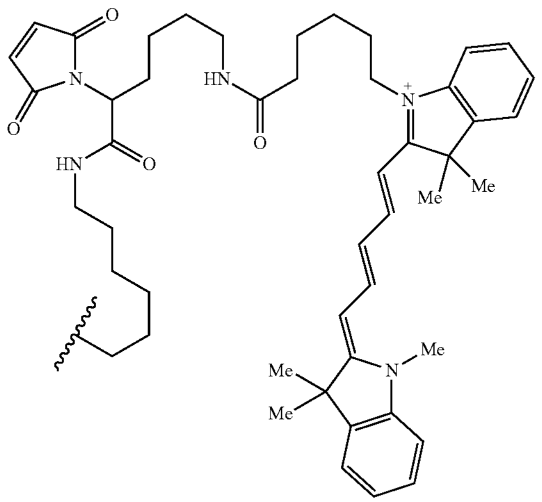

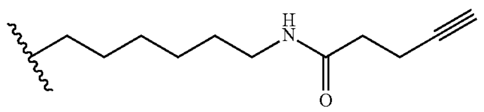

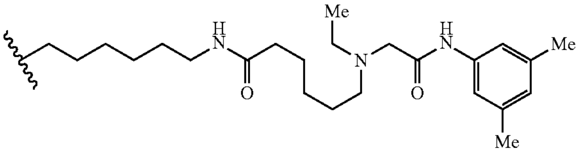

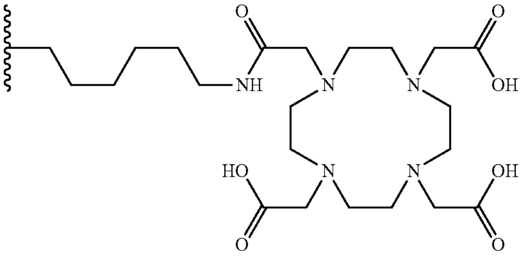

R2 is hydrogen. R3 can be a group such as hydrogen or propyl. R4 can be a group such as hydrogen or propyl. R5 can be a group such as hydrogen, sulfate, —OC(═O)$R_A$, wherein $R_A$ is n-propyl or phenyl. R6 can be a group such as hydrogen, sulfate, —OC(═O)$R_A$, wherein $R_A$ is n-propyl or phenyl. R7 can be a group such as hydrogen or —$(CH_2)_2$C(═O)N($R_A$). In each occurrence of $R_A$ in R2 to R7 can be independently a group such as hydrogen, hydroxyl or alkoxy.

Structure B

Embodiments of the compound include structure B, an isomer thereof, a tautomer thereof, or a prodrug of any of these, or a pharmaceutically acceptable salt of any of these. Structure B is a generic structure for gonyanutoxin 3. See also FIG. 1.

Structure B

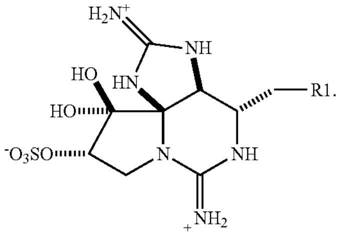

R1 can be a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl(alkyl), nitro, oxa, oxo, sulfonyl, sulfonamido, sulfone, —O$R_A$, ═O, —C(═O)$R_A$, —OC(═O)$R_A$, —OC(═O)O$R_A$, —OC(═O)N$(R_A)_2$, —$CO_2R_A$, —CN, —SCN, —S$R_A$, —SO$R_A$, —$SO_2R_A$, —$NO_2$, —N$(R_A)_2$, —NHC(O)$R_A$, or —C$(R_A)_3$, wherein each occurrence of $R_A$ can be independently a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl (alkyl), nitro, oxa, oxo, sulfonyl, sulfonamido, or sulfone.

In an embodiment, R1 can be a group such as hydroxyl, alkoxyl, cyano, heteroaryl, (monosubstituted)amino, protected (monosubstituted)amino, (disubstituted)amino, —O$R_A$, ═O, —OC(═O)$R_A$, —OC(═O)O$R_A$, —OC(═O)N$(R_A)_2$, —CN, —S$R_A$, —SO$R_A$, —$SO_2R_A$, —$NO_2$, —N$(R_A)_2$, or —NHC(O)$R_A$, wherein each occurrence of $R_A$ can be independently a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl(alkyl), nitro, oxa, oxo, sulfonyl, sulfonamido, or sulfone.

In an embodiment, R1 can be a group such as hydroxyl, —OC(═O)NH$R_A$, OC(═O)N($R_A$), wherein each occurrence of $R_A$ can be independently a group such as hydrogen, methyl, or tetradecyl.

Structure C

Embodiments of the compound include structure C (FIG. 1), an isomer thereof, a tautomer thereof, or a prodrug of any of these, or a pharmaceutically acceptable salt of any of these. Structure C is a generic structure for gonyanutoxin 2. See also FIG. 1.

Structure C

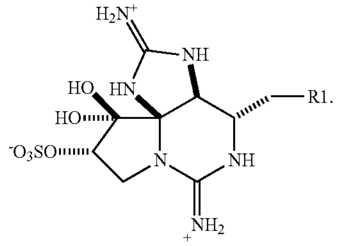

R1 can be a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl(alkyl), nitro, oxa, oxo, sulfonyl, sulfonamido, sulfone, —$OR_A$, =O, —C(=O)$R_A$, —OC(=O)$R_A$, —OC(=O)$OR_A$, —OC(=O)N$(R_A)_2$, —$CO_2R_A$, —CN, —SCN, —$SR_A$, —$SOR_A$, —$SO_2R_A$, —$NO_2$, —N$(R_A)_2$, —NHC(O)$R_A$, or —C$(R_A)_3$, wherein each occurrence of $R_A$ can be independently a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl (alkyl), nitro, oxa, oxo, sulfonyl, sulfonamido, or sulfone.

In an embodiment, R1 can be a group such as hydroxyl, alkoxyl, cyano, heteroaryl, (monosubstituted)amino, protected (monosubstituted)amino, (disubstituted)amino, —$OR_A$, =O, —OC(=O)$R_A$, —OC(=O)$OR_A$, —OC(=O)N$(R_A)_2$, —CN, —$SR_A$, —$SOR_A$, —$SO_2R_A$, —$NO_2$, —N$(R_A)_2$, or —NHC(O)$R_A$, wherein each occurrence of $R_A$ can be independently a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl(alkyl), nitro, oxa, oxo, sulfonyl, sulfonamido, or sulfone.

In an embodiment, R1 can be a group such as hydroxyl, —OC(=O)NH$R_A$, —OC(=O)N($R_A$) wherein each occurrence of $R_A$ can be independently a group such as hydrogen, methyl, or tetradecyl.

Structure D

Embodiments of the compound include structure D (FIG. 1), an isomer thereof, a tautomer thereof, or a prodrug of any of these, or a pharmaceutically acceptable salt of any of these. Structure D is a generic structure for saxitoxin. See also FIG. 1.

Structure D

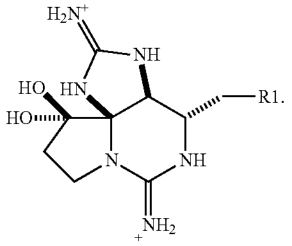

R1 can be a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl(alkyl), nitro, oxa, oxo, sulfonyl, sulfonamido, sulfone, —$OR_A$, =O, —C(=O)$R_A$, —OC(=O)$R_A$, —OC(=O)$OR_A$, —OC(=O)N$(R_A)_2$, —$CO_2R_A$, —CN, —SCN, —$SR_A$, —$SOR_A$, —$SO_2R_A$, —$NO_2$, —N$(R_A)_2$, —NHC(O)$R_A$, or —C$(R_A)_3$, wherein each occurrence of $R_A$ can be independently a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl (alkyl), nitro, oxa, oxo, sulfonyl, sulfonamido, or sulfone.

In an embodiment, R1 can be a group such as hydroxyl, alkoxyl, cyano, heteroaryl, (monosubstituted)amino, protected (monosubstituted)amino, (disubstituted)amino, —$OR_A$, =O, —OC(=O)$R_A$, —OC(=O)$OR_A$, —OC(=O)N$(R_A)_2$, —CN, —SCN, —$SR_A$, —$SOR_A$, —$SO_2R_A$, —$NO_2$, —N$(R_A)_2$, or —NHC(O)$R_A$, wherein each occurrence of $R_A$ can be independently a group such as hydrogen, halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl(alkyl), nitro, oxa, oxo, sulfonyl, sulfonamido, or sulfone.

In an embodiment, R1 can be a group such as hydroxyl, —OC(=O)NH$R_A$, —OC(=O)N($R_A$) wherein each occurrence of $R_A$ can be independently a group such as hydrogen, methyl, i-propyl, tetradecyl or any of the following:

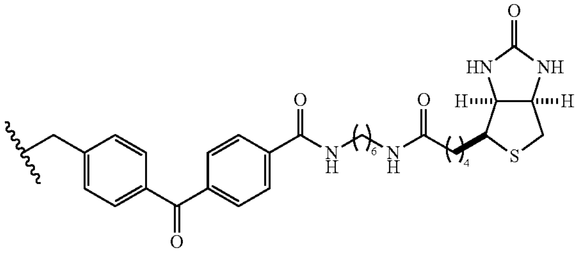

-continued
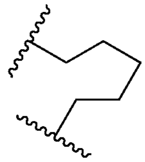
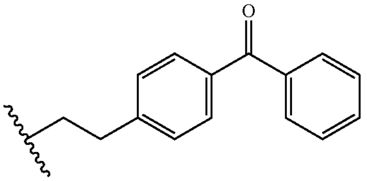
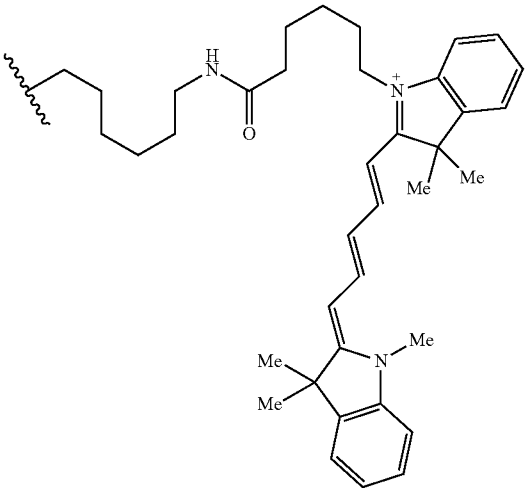
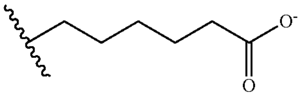
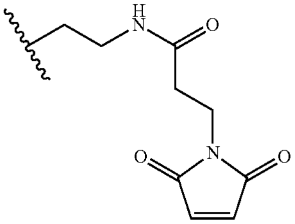
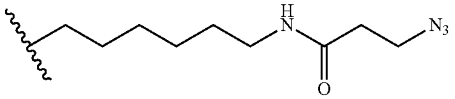
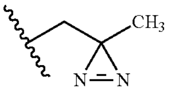
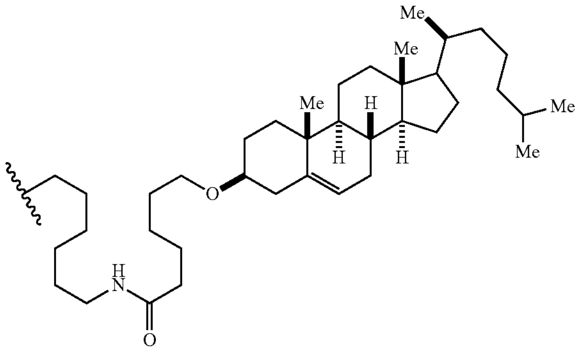
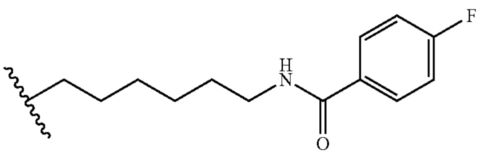
-continued
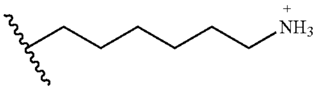
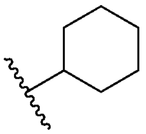
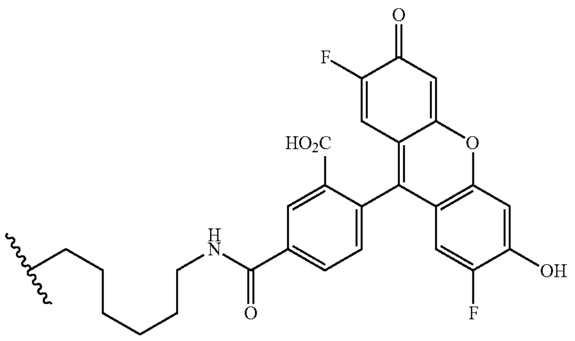
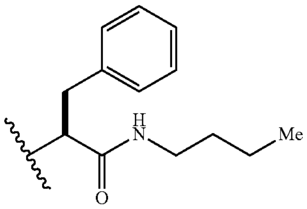
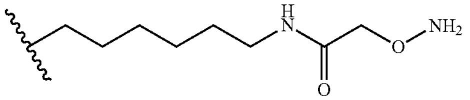
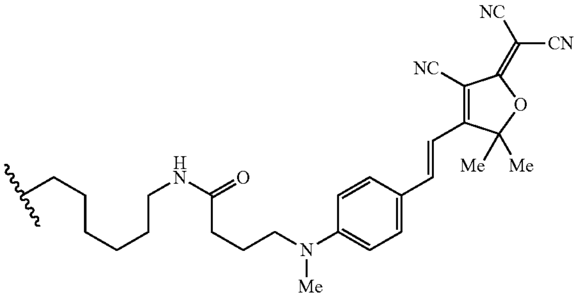
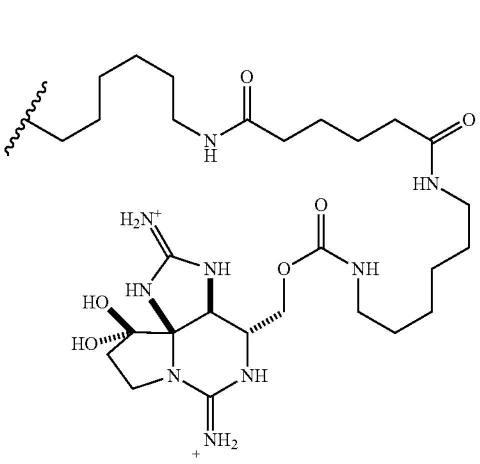

-continued

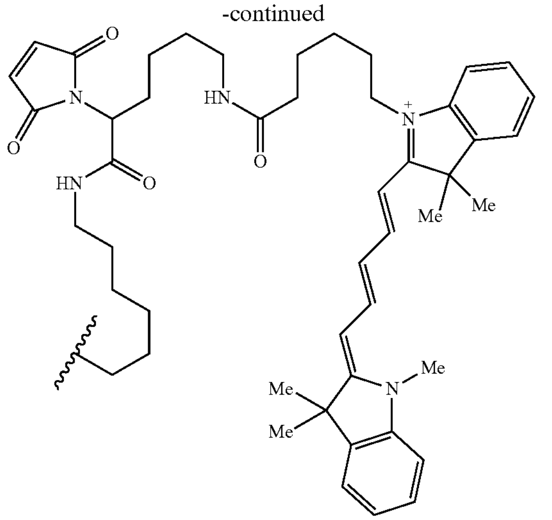

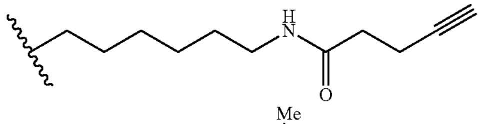

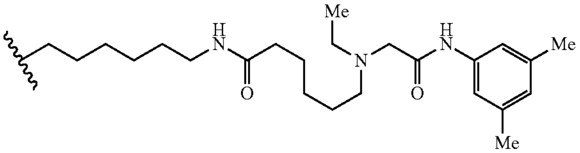

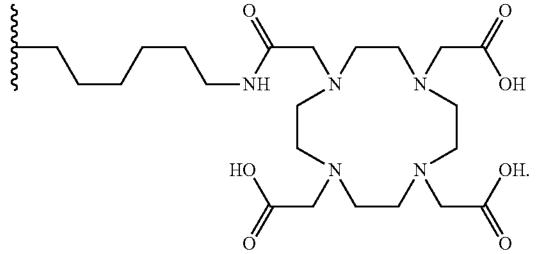

In an embodiment of any one of Structure A, Structure B, Structure C, and Structure D, the groups (e.g., R1 to R7 groups as is appropriate for each structure) are not selected to produce a compound having the structure of saxitoxin, neosaxitoxin, gonyautoxin, or zetekitoxin AB. In other words, compositions, pharmaceutical compositions, methods of treatment, and the like, can include one or more of Structure A, Structure B, Structure C, or Structure D with the proviso that the R groups are not selected to produce any one of saxitoxin, neosaxitoxin, gonyautoxin, or zetekitoxin AB. In an embodiment, the selection of the R groups for each of Structure A, Structure B, Structure C, and Structure D are conducted to exclude the structures that correspond to saxitoxin, neosaxitoxin, gonyautoxin, or zetekitoxin AB. See FIG. 1 for these structures which are not selected to produce a novel compound as disclosed herein.

The subject treatment methods can also employ prodrugs of each of the embodiments of the compounds described in the discussion of structures A-D and the associated discussion herein. Exemplary prodrugs can be activated by liver enzymes (e.g., cyclic-1,3-propanyl esters substituted with groups that promote an oxidative cleavage reaction by CYP3A, etc.). These modifications can render compositions of the present disclosure inactive or less active until it reaches the liver (see, Current Opinion in Investigational Drugs 2006 Vol 7 No 2, 109-117; *J. Med. Chem.* 2008, 51, 2328-2345; and Nucleosides, Nucleotides, and Nucleic Acids, 24 (5-7):375-381, (2005) each of which is incorporated herein by reference for the corresponding discussion).

Methods of Synthesis

In general, embodiments of the compounds provided herein including each of the embodiments of the compounds described in the discussion of structures A-D in FIG. 1 and the associated discussion herein can be made according to organic synthesis techniques known to those skilled in this art and/or according to the synthesis schemes provided herein. In particular, the Examples provided herein provide some specifics and guidance for preparing compounds of the present disclosure.

Where desired, synthesis of the subject compound begins with commercially available chemicals and/or from compounds described in the chemical literature. "Commercially available chemicals" may be obtained from standard commercial sources including Acros Organics (Pittsburgh, Pa.), Aldrich Chemical (Milwaukee, Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire UK), Frontier Scientific (Logan UT), ICN Biomedicals, Inc. (Costa Mesa, Calif.), Key Organics (Cornwall U.K.), Lancaster Synthesis (Windham, N.H.), Maybridge Chemical Co. Ltd. (Cornwall U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

In addition, methods known to one of ordinary skill in the art may be identified through various reference books and databases. Suitable reference books and treatise that detail the synthesis of reactants useful in the preparation of the compounds of the present disclosure described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992

Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes. Unless specified to the contrary, the reactions described herein take place at atmospheric pressure, generally within a temperature range from −78° C. to 200° C. Further, except as otherwise specified, reaction times and conditions are intended to be approximate, e.g., taking place at about atmospheric pressure within a temperature range of about −78° C. to about 110° C. over a period of about 1 to about 24 hours; reactions left to run overnight average a period of about 16 hours.

Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein. However, other equivalent separation or isolation procedures can also be used.

It will be understood that chemical synthesis may be asymmetric. When desired, the (R)- and (S)-isomers of the compounds of the present disclosure, if present, may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

Embodiments of the compounds described herein can be optionally contacted with a pharmaceutically acceptable acid to form the corresponding acid addition salts.

Many of the optionally substituted starting compounds and other reactants may be commercially available, e.g., from Aldrich Chemical Company (Milwaukee, Wis.) or can be readily prepared by those skilled in the art using commonly employed synthetic methodology.

The compounds of the present disclosure can be synthesized by an appropriate combination of known synthetic methods in the art and the instant disclosure. The discussion below is offered to illustrate certain of the diverse methods available for use in making the compounds of the present disclosure and is not intended to limit the scope of reactions or reaction sequences that can be used in preparing the compounds of the present disclosure.

The examples describe synthesis of Structures A-D, as well as the synthesis of radiolabeled and fluorescent saxitoxin and gonyautoxin derivatives.

Methods of Use

Also disclosed herein are uses for the saxitoxin analogues, including the following.

The use of a saxitoxin analogue in the preparation of a medicament for the treatment of a subject in need of treatment, said medicament comprising a saxitoxin analogue as disclosed herein, including an isomer thereof, a tautomer thereof, or a prodrug of any of these, or a pharmaceutically acceptable salt of any of these. The amount of said saxitoxin analogue in said medicament is preferably an effective amount.

The use of a saxitoxin analogue in the preparation of a medicament for reducing neuronal activity or effecting muscular relaxation in a subject, said medicament comprising a saxiroxin analogue compound as disclosed herein, or an isomer thereof, a tautomer thereof, or a prodrug of any of these, or a pharmaceutically acceptable salt of any of these. The amount of said saxitoxin analogue in said medicament is preferably an amount that is effective to reduce neuronal activity in the subject or to bring about muscular relaxation in a subject.

The use of a saxitoxin analogue in the preparation of a medicament for reducing neuronal activity or effecting muscular relaxation in a subject, said medicament comprising a saxiroxin analogue compound as disclosed herein, or an isomer thereof, a tautomer thereof, or a prodrug of any of these, or a pharmaceutically acceptable salt of any of these, wherein the subject suffers from a voltage-gated sodium channel-enhanced ailment. In embodiments, a voltage-gated sodium channel-enhanced ailment is selected from the group consisting of acute pain, anal fissures, arthritis, back pain, chronic pain, dental pain, fibromyalgia, joint pain, migraine headaches, neck pain, neuropathic pain, obstetric pain, post-herpetic neuralgia, post-operative pain, shingles, tension headaches or trigeminal neuralgia, blepharospasm, cancer, cardiac arrythmia, epilepsy, focal dystonia, hyperhidrosis, muscle spasms, and urinary bladder relaxation.

The use of a saxitoxin analogue in the preparation of a medicament for the treatment of a subject in need of treatment for pain, said medicament comprising a saxitoxin analogue as disclosed herein, including an isomer thereof, a tautomer thereof, or a prodrug of any of these, or a pharmaceutically acceptable salt of any of these. The amount of said saxitoxin analogue in said medicament is preferably an effective amount.

The use of a saxitoxin analogue in the preparation of a medicament for the treatment of a subject in need of treatment for pain, wherein the pain is selected from the group consisting of acute pain, anal fissure pain, arthritis pain, back pain, blepharospasm pain, cancer pain, chronic pain, dental pain, fibromyalgia pain, joint pain, migraine headache pain, neck pain, visceral pain, neuropathic pain, obstetric pain, post-herpetic neuralgia pain, post-operative pain, sympathetically maintained pain, shingles pain, tension headache pain, trigeminal neuralgia pain, myositis pain, musculoskeletal pain; lower back pain, pain from sprains and strains; pain associated with functional bowel disorders such as non-ulcer dyspepsia, non-cardiac chest pain and irritable bowel syndrome; pain associated with myocardial ischemia; toothache pain; and pain from dysmenorrhea.

The use of a saxitoxin analogue in the preparation of a composition for the diagnosis of a disorder in a subject, the use comprising preparing a composition comprising a saxitoxin analogue compound as disclosed herein, including an isomer thereof, a tautomer thereof, or a prodrug of any of these, or a pharmaceutically acceptable salt of any of these. In embodiments, the amount of the saxitoxin analogue compound is an amount that is effective to localize a voltage-gated sodium channel-enhanced ailment to a specific area in the subject's body.

The use of a saxitoxin analogue in the preparation of a composition for imaging a subject, the use comprising preparing a composition comprising a saxitoxin analogue compound as disclosed herein, including an isomer thereof, a tautomer thereof, or a prodrug of any of these, or a pharmaceutically acceptable salt of any of these. In embodiments, the amount of the saxitoxin analogue compound is an amount that is effective to detect the localization of said compound within said subject during an imaging procedure.

The use of a saxitoxin analogue in the preparation of a medicament for the treatment of wrinkles, said medicament comprising a saxitoxin analogue as disclosed herein, including an isomer thereof, a tautomer thereof, or a prodrug of any of these, or a pharmaceutically acceptable salt of any of these. In embodiments, the amount of the saxitoxin analogue compound is an amount that is effective to reduce or eliminate wrinkles.

Pharmaceutical Formulations and Routes of Administration

Embodiments of the present disclosure provide for pharmaceutical compositions comprising one or more of the embodiments of the compounds described in the discussion of structures A-D and the associated discussion herein with or without pharmaceutically acceptable excipients, diluents, carriers and/or adjuvants. In some embodiments, the compound-containing pharmaceutical compositions are formulated to be substantially free of excipients. In other embodiments, the compound or composition can be formulated with one or more pharmaceutically acceptable auxiliary substances.

In an embodiment, the compound can be combined with another agent to prepare a composition of the present disclosure, and the composition can include one or more pharmaceutically acceptable excipients, diluents, carriers and/or adjuvants.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the present disclosure, the compound or composition is administered to the host using any means capable of resulting in the desired effect (e.g., treating pain, reduction in pain, and the like). Thus, embodiments of the compound or composition can be incorporated into a variety of formulations for therapeutic administration. For example, the compound or composition can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In embodiments, the compound or composition may be formulated for topical administration, as a liquid, gel, salve, cream, ointment, unguent, oil, paste, powder, or other formulation suitable for topical administration. Such compound and compositions may be formulated for direct application to the skin, or to a tissue, or external or internal surface or portion of a patient, or may be formulated for integration into a dressing, bandage, patch, tape, staple, catheter, needle, depot delivery system, or other device or implement useful for administration of a compound or composition having features of the present disclosure. Dosage forms for topical or transdermal administration of a compound of the present disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of the present disclosure. Additionally, the present disclosure contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In pharmaceutical dosage forms, the compound or composition may be administered in the form of its pharmaceutically acceptable salts, or a subject active agent may be used alone or in appropriate association, as well as in combination, with other pharmaceutically active compounds. The following methods and excipients are merely exemplary and are in no way limiting.

For oral preparations, the compound or composition can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Embodiments of the compound or composition can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Embodiments of the compound or composition can be utilized in aerosol formulation to be administered via inhalation. Embodiments of the compound or composition can be formulated into pressurized acceptable propellants such as dichlorodifluoromethane, propane, nitrogen and the like.

Furthermore, embodiments of the compound or composition can be made into suppositories by mixing with a variety of bases such as emulsifying bases or water-soluble bases. Embodiments of the compound or composition can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compounds of the present disclosure. Similarly, unit dosage forms for injection or intravenous administration may comprise the compound in a composition as a solution in sterile water, normal saline or another pharmaceutically acceptable carrier.

Embodiments of the compound or composition can be formulated in an injectable composition in accordance with the present disclosure. Typically, injectable compositions are prepared as liquid solutions or suspensions; solid forms suitable for solution in, or suspension in, liquid vehicles prior to injection may also be prepared. The preparation may also be emulsified or the active ingredient (compound) encapsulated in liposome vehicles in accordance with the present disclosure.

In an embodiment, the compound or composition is formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of the compound can be accomplished using any of a variety of refillable, pump systems. Pumps provide consistent, controlled release over time. In some embodiments, the compound is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, the compound or composition is delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present disclosure is the Synchromed infusion pump (Medtronic).

Suitable excipient vehicles for the compound or composition are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the compound or composition adequate to achieve the desired state in the subject being treated.

Compositions of the present disclosure include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix. Similarly, the sustained release formulations of embodiments of the present disclosure can help maintain viral-inhibiting concentrations over a longer time interval.

In another embodiment, the pharmaceutical composition of the present disclosure (as well as combination compositions) can be delivered in a controlled release system. For example, the compound may be administered using intravenous infusion, an implantable osmotic pump, a transdermal patch, liposomes, or other modes of administration. In one embodiment, a pump may be used (Sefton (1987). *CRC Crit. Ref Biomed. Eng.* 14:201; Buchwald et al. (1980). *Surgery* 88:507; Saudek et al. (1989). *N. Engl. J. Med.* 321:574). In another embodiment, polymeric materials are used. In yet another embodiment, a controlled release system is placed in proximity to the therapeutic target, i.e., the liver, thus requiring only a fraction of the systemic dose. In yet another embodiment, a controlled release system is placed in proximity to the therapeutic target, thus requiring only a fraction of the systemic dose. Other controlled release systems are discussed in the review by Langer (1990). *Science* 249:1527-1533.

In another embodiment, the compositions of the present disclosure (as well as combination compositions separately or together) include those formed by impregnation of a compound described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

Embodiments of the compounds disclosed herein can be formulated in a pharmaceutical composition comprising an effective amount of the compound for its intended use. For example, compounds of the present disclosure can be formulated in a unit dose form between about 1 μg to 10 mg for treating pain. In some embodiments, compounds or compositions of the present disclosure can be formulated in a unit dose of about 1 μg to 20 μg, of about 20 μg to 1 mg, of about 1 mg to 10 mg, of about 10 mg to 100 mg, and of about 50 mg to 500 mg. In particular, an embodiment including a compound can be formulated in 0.1 μg, 0.2 μg, 0.5 μg, 1 μg, 20 μg, 50 μg, 100 μg, 200 μg, 500 μg, 1 mg, 2 mg, 5 mg, 10 mg, 20 mg, 50 mg, 100 mg, 200 mg, and 500 mg unit dose form. In one embodiment, the unit dose form is a tablet; in another, the unit dose form is a capsule. The tablet can be formulated as immediate release dose form or as sustained release form. In yet another embodiment, the unit dose form is a liquid.

Uses of the Compounds and Pharmaceutical Compositions

The subject compounds and pharmaceutical compositions thereof are particularly useful for studying, imaging, treating pain or conditions related to pain. The methods of the present disclosure also provide the ability to target, diagnose, and/or research various disorders associated with pain. This includes atypical pain syndromes such as, but not limited to, fibromyalgia, chronic fatigue syndrome, reflex sympathetic dystrophy, and peripheral nerve entrapment syndrome.

The ability to image pain provides objective indicia of those conditions, as well as the possibility of determining the degree and/or intensity of the pain and/or stress. For pain, it also may allow the location of the source or origin of the pain, if not apparent from examining the subject.

The treatment methods typically comprise administering to a subject needing treatment for pain a therapeutically effective amount of any one of the embodiments of the structures A-D and the associated discussion in one or more doses. For subjects already having pain, the method of the present disclosure is generally effective in treating (e.g., reducing or altering the pain) over a period of a few days, a few weeks or a few months.

Embodiments of the present disclosure also provide methods of prophylactically treating pain comprising administering an effective amount of any one of the embodiments of the structures A-D and the associated discussion described herein to a subject in need thereof. The administration of compounds or compositions of the present disclosure may also be advantageous for patients who cannot tolerate other pain medication or if other pain medications are not helpful in treating pain.

The compounds of the present disclosure and pharmaceutical composition comprising the same can be administered to a subject in one or more doses. In an embodiment, the compound or composition can be administered in an amount of about 1 μg to 10 mg per dose, e.g., about 1 μg to 5 μg, about 5 μg to 10 μg, about 10 μg to 50 μg, about 50 μg mg to 100 μg, about 100 μg to 200 μg, about 200 μg to 400 μg, about 400 μg to 800 μg, about 800 μg to 1 mg, about 1 mg to 2 mg, about 2 mg to 3 mg, about 3 mg to 4 mg, about 4 mg to 5 mg, about 5 mg to 6 mg, about 6 mg to 7 mg, about 7 mg to 8 mg, about 8 mg to 9 mg, or about 9 mg to 10 mg per dose.

In an embodiment, the amount of the compound or composition per dose is determined on a per body weight basis. For example, the amount of the compound or composition per dose, as determined on a per body weight basis, may be, for example, about 10 ng/kg, about 15 ng/kg, about 20 ng/kg, about 50 ng/kg, about 100 ng/kg, about 200 ng/kg, about 500 ng/kg, about 1 μg/kg, about 2 μg/kg, about 5 μg/kg, about 10 μg/kg, about 20 μg/kg, about 50 mg/kg, about 100 mg/kg, about 200 μg/kg, about 500 μg/kg, about 1 mg/kg, about 2 mg/kg, and about 5 mg/kg.

For example, in an embodiment, the compound or composition can be administered in an amount of about 15 ng/kg to 150 μg/kg, e.g., about 15 ng/kg to 30 ng/kg, about 30 ng/kg to 60 ng/kg, about 60 mg/kg to 120 ng/kg, about 120 ng/kg to 240 ng/kg, about 240 ng/kg to 480 ng/kg, about 480 ng/kg to 700 ng/kg, about 700 mg/kg to 1 μg/kg, about 1 μg/kg to 2 μg/kg, about 2 μg/kg to 4 μg/kg, about 4 μg/kg to 8 μg/kg, about 8 μg/kg to 15 μg/kg, about 15 μg/kg to 20 μg/kg, about 20 μg/kg to 30 μg/kg, about 30 μg/kg to 40 μg/kg, about 40 μg/kg to 60 μg/kg, about 60 μg/kg to 90 μg/kg, or about 90 μg/kg to 120 mg/kg, or more than about 120 μg/kg.

Those of skill will readily appreciate that dose levels can vary as a function of the specific compound or composition administered, the severity of the symptoms and the susceptibility of the subject to side effects. Preferred dosages for a given compound are readily determinable by those of skill in the art by a variety of means.

In an embodiment, multiple doses of the compound or composition are administered. The frequency of administration of the compound or composition can vary depending on any of a variety of factors, e.g., severity of the symptoms, and the like. For example, in an embodiment, the compound or composition is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid). As discussed above, in an embodiment, the compound or composition is administered continuously.

The duration of administration of the compound or composition, e.g., the period of time over which the compound or composition is administered, can vary, depending on any of a variety of factors, e.g., patient response, etc. For example, the compound or composition can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

The practice of a method of the present disclosure typically involves administering an effective amount of the compound, composition, or a pharmaceutical composition comprising such a compound. The specific dose will vary depending on the particular compounds chosen, the dosing regimen to be followed, whether it is administered in combination with other compounds, timing of administration, the tissue to which it is administered, and the physical delivery system in which it is carried.

Embodiments of the compounds, compositions, and pharmaceutical compositions thereof can be administered to a subject using any available method and route suitable for drug delivery, including in vivo and ex vivo methods, as well as systemic and localized routes of administration.

Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. Embodiments of the compound or composition can be administered in a single dose or in multiple doses.

Embodiments of the present disclosure can be administered to a host using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the compound or composition. Where systemic delivery is desired, administration typically involves invasive or systemically absorbed topical or mucosal administration of pharmaceutical preparations.

The compound or composition can also be delivered to the subject by enteral administration. Enteral routes of administration include, but are not limited to, oral and rectal (e.g., using a suppository) delivery.

Methods of administration of the compound or composition through the skin or mucosa include, but are not limited to, topical application of a suitable pharmaceutical preparation, transdermal transmission, injection and epidermal administration. For transdermal transmission, absorption promoters or iontophoresis are suitable methods. In embodiments, mere contact between the skin, mucosa, or other body tissue with the compound is effective to administer the compound. In addition, carriers, enhancers, and other compounds may be used to speed or enhance the administration of the compound. Iontophoretic transmission may be accomplished using commercially available "patches" that deliver their product continuously via electric pulses through unbroken skin for periods of several days or more. In some embodiments, compositions of the present disclosure are administered by oral, intravenous, transdermal, sublingual, intramuscular, or rectal route.

EXAMPLES

The following examples are put forth so as to provide those of ordinary skill in the art with a complete disclosure and description of how to make and use the present disclosure, and are not intended to limit the scope of what the inventors regard as their disclosure nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Voltage-gated sodium ion channels ($Na_V$) serve an obligatory role in the generation of bioelectricity and are essential for all of life's processes. (see, e.g., Hille, B. *Ion Channels of Excitable Membranes,* 3$^{rd}$ Ed., Sinauer: Sunderland, Mass., 2001.) Genes that encode for ten unique Na channel isoforms ($Na_V$1.1-1.9, $Na_X$) have been identified in mammalian cells. (see, (a) Catterall, W. A.; Yu, F. H. *Genome Biology* 2003, 4, 207. (b) Catterall, W. A.; Goldin, A. L.; Waxman, S. G. *Pharm. Rev.* 2005, 57, 397.) Differences in the biophysical properties between these protein subtypes, their membrane concentrations and spatial distribution define the signaling characteristics of a neuron. (see, e.g., (a) Novakovic, S. D.; Eglen, R. M.; Hunter, J. C. *Trends in Neurosci.* 2001, 24, 473. (b) Lai, H. C.; Jan, L. Y.; *Nat. Rev. Neurosci.* 2006, 7, 548. (c) Rush, A. M.; Cummins, T. R.; Waxman, S. G. *J. Physiol.* 2007, 579, 1.) Aberrant $Na_V$ function and/or expression is thought to be associated with numerous disease states, including arrhythmia, epilepsy, neuropathic pain, and congenital analgesia. (see, e.g., (a) Keating, M T.; Sanguinetti, M. C. *Cell* 2001, 104, 569. (b) Lossin, C.; Wang, D. W.; Rhodes, T. H.; Vanoye, C. G.; George, A. L. Jr. *Neuron,* 2002, 34, 877. (c) Rogers, M.; Tang, L.; Madge, D. J.; Stevens, E. B. Semin *Cell. Dev. Biol.* 2006, 17, 571. (d) Cox, J. J.; Reimann, F.; Nicholas, A. K.; Thornton, G.; Roberts, E.; Springell, K.; Karbani, G.; Jafri, H.; Mannan, J.; Raashid, Y.; Al-Gazali, L.; Hamamy, H.; Valente, E. M.; Gorman, S.; Williams, R.; McHale, D. P.; Wood, J. N.; Gribble, F. M.; Woods, C. G. *Nature* 2006, 444, 894.) Accordingly, chemical tools for exploring protein structure, for modulating the activity of specific $Na_V$ isoforms, and for tracking dynamic events associated with $Na_V$ regulation and expression are sought to further understand the pathophysiologies associated with channel function. (see, e.g., (a) Anger, T.; Madge, D. J.; Mulla, M.; Ridall, D. *J. Med. Chem.* 2001, 44, 115. (b) Priest, B. T.; Kaczorowski, G. J. *PNAS* 2007, 104, 8205.) Herein, we describe our development of such agents, for which the shellfish poison (+)-saxitoxin 1 (STX)—a single digit nanomolar inhibitor of certain $Na_V$ subtypes—provides the molecular blueprint (FIG. 2A and FIG. 2B). Our studies thus far have revealed discrepancies with available models of the binding pose of STX in the channel mouth. In addition, we establish a means for accessing carbamate-modified forms of the toxin and show that such structural changes do not greatly diminish substrate-receptor binding affinity.

The fully functional voltage-gated $Na^+$ channel consists of a large heteromeric α-subunit (~260 kDa) and one or two auxiliary β-subunits (33-36 kDa). (see, (a) Catterall, W. A.; Yu, F. H. *Genome Biology* 2003, 4, 207. (b) Catterall, W. A.; Goldin, A. L.; Waxman, S. G. *Pharm. Rev.* 2005, 57, 397.) In the absence of protein crystallographic data, small molecule pharmacological probes together with protein mutagenesis and electrophysiology have provided much of the structural insights that currently exist for this family of macromolecules. (see, e.g., Choudhary, G.; Shang, L.; Li, X. F.; Dudley, S. C. *Biophys. J.* 2002, 83, 912.) These data together with X-ray structures of associated $K^+$ ion channels, Kcsa and MthK, have made possible the construction of homology models of the $Na_V$ α-subunit. (see, e.g., (a) Lipkind, G. M.; Fozzard, H. A. *Biochemistry* 2000, 39, 8161. (b) Tikhonov, D. B.; Zhorov, B. S. *Biophys. J.* 2005, 88, 184.) The outer mouth of the channel, so-called Site I, includes the ion selectivity filter and is considered to be the receptor site for STX and related guanidinium poisons (FIG. 2A and FIG. 2B). (see, Llewellyn, L. E. *Nat. Prod. Rep.* 2006, 23, 200.) Five carboxylate residues line this pore region (D400, E755, E403, E758, D1532, $Na_V$1.4 numbering); their presence is critical for high affinity STX binding, as shown by site-directed mutagenesis studies. (see, (a) Terlau, H.; Heinemann, S. H.; Stühmer, W.; Pusch, M.; Conti, F.; Imoto, K.; Numa, S. *Febs Lett,* 1991, 293, 93. (b) Heinemann, S. H.; Terlau, H.; Stühmer, W.; Imoto, K.; Numa, S. *Nature* 1992, 356, 441. (c) Schlief, T.; Schönherr, R.; Imoto, K.; Heinemann, S. H. *Eur. Biophys. J.* 1996, 25, 75. (d) Chiamvimonvat, N.; Pérez-Garcia, M. T.; Tomaselli, G. F.; Marban, E. *J. Physiol.* 1996, 491, 51. (e) Chiamvimonvat, N.; Pérez-Garcia, M. T.; Ranjan, R.; marban, E.; Tomaselli, G. F. *Neuron* 1996, 16, 1037. (f) Hui, L.; McIntyre, D.; French, R. J. *J. Gen. Physiol.* 2003, 122, 63.) Computational models by Lipkind and Fozzard, Dudley, and Zhorov all posit that the 7,8,9-guanidine of STX points towards the ring of four amino acids that comprise the selectivity filter (also known as the DEKA loop). (see, (a) Lipkind, G. M.; Fozzard, H. A. *Biochemistry* 2000, 39, 8161. (b) Tikhonov, D. B.; Zhorov, B. S. *Biophys. J.* 2005, 88, 184. (c) Llewellyn, L. E. *Nat. Prod. Rep.* 2006, 23, 200.) Specific contacts between the C13-carbamate unit, the C12-hydrated ketone, and the 1,2,3-guanidinium moiety and the carboxylate residues of the outervestibule loop are also highlighted.

As a starting point for the investigation, we chose to examine first the contribution of the primary carbamate as a hydrogen-bond donor to the overall binding affinity of the toxin. Naturally occurring decarbamoyl STX (dc-STX) displays a 20-40% reduction in potency relative to STX. (see, (a) Koehn, F. E.; Schnoes, H. K.; Kao, C. Y. *Biochim. Biophys. Acta: Biomembranes* 1983, 734, 129. (b) Strichartz, G. R.; Hall, S.; Magnani, B.; Hong, C. Y.; Kishi, Y.; Debin, J. A. *Toxicon* 1995, 33, 723.) Previous efforts to alter this functional group through semi-synthetic modification of dc-STX have been limited to a single succinate derivative. (see, (a) Schlager, J. J.; Williams, K. C.; Hornyak, M. J.; Courtney, B. C.; Smith, J. R. *Medical Defense Bioscience Review, Proceedings*, Baltimore, May 12-16, 1996. (b) Robillot, C.; Kineavy, D.; Burnell, J.; Llewellyn, L. E. *Toxicon* 2009, 53, 460.) With the availability of a de novo synthesis to STX, it is possible for us to change at will this C13-side element. Accordingly, N,N-dimethyl-STX 2 has been prepared and evaluated for its ability to block $Na^+$ current. Electrophysiology measurements are performed in a whole cell voltage-clamp format against the heterologously expressed α-subunit of the rat skeletal channel, $Na_V$1.4 (CHO cell). (see, e.g., Moran, O.; Picollo, A.; Conti, F. *Biophys. J.* 2003, 84, 2999.) FIG. 3A and FIG. 3B show current recordings following a 10 ms depolarizing pulse of 100 mV amplitude from a holding potential of −100 mV. Increasing concentrations of 2 were perfused into the external solution, resulting in decreased peak current. These data were fit to a Langmuir isotherm to give an $IC_{50}$ of 2.1±0.1 nM for 2, a value nearly equal to the $IC_{50}$ recorded for our synthetic (+)-STX. This result seems to indicate that the role of the primary carbamate in the natural product is not as a hydrogen-bond donor. (see, for background, Tikhonov, D. B.; Zhorov, B. S. *Biophys. J.* 2005, 88, 184.) Such a finding also provides the motivation for exploring further the steric environment of the protein pore in the vicinity of the C13 carbamoyl residue.

A strategic modification to one of our previously published routes to (+)-STX has been devised in order to prepare alternate C13 carbamate forms (FIG. 4). (see, Fleming, J. J.; McReynolds, M. D.; Du Bois, J. *J. Am. Chem. Soc.* 2007, 129, 9964.) The tricyclic oxazolidinone 4 represents a base of our new synthetic plan, our assumption being that nucleophilic amines would open selectively this strained heterocycle. This structure can be fashioned in just three steps from the 9-membered ring guanidine 3, a material that is now routinely synthesized in our lab on >5 g scales. To access 4, sequential formation of the C13-Troc carbonate and ring closure proved necessary; the use of other carbonylating agents (i.e., phosgene, carbonyldiimidazole) led almost exclusively to the C4-C13 alkene. Oxazolidinone ring opening does indeed occur smoothly with primary amines to furnish the corresponding secondary carbamates. Two subsequent transformations, which include Lewis acid-mediated guanidine ring closure and deprotection and C12 oxidation, complete the assembly of the tailored saxitoxins.

Saxitoxin C13-derivatives 8-12 have been evaluated for potency against $rNa_V$1.4 (as described in FIG. 5). The incorporation of a linear N-hexyl moiety as in 8 leads to only a slight reduction in $IC_{50}$ relative to the natural product. This result contrasts measurements with the branched N-isopropyl structure 9, which exhibits a rather marked loss in binding affinity. Without being held to a particular theory, it appears that the carbamate moiety rests in a rather narrow canyon that may extend into extracellular space. (see, Sato, C.; Ueno, Y.; Asai, K.; Takahashi, K.; Sato, Masahiko, S.; Engel, A.; Fujiyoshi, Y. *Nature* 2001, 409, 1047.) Other data, namely results from voltage-clamp recordings with 10 and 12, supports this conclusion. It is interesting to note, however, that the incorporation of a carboxylate reside distal to the saxitoxin core (i.e., 11) reduces drug potency. The benzophenone-labeled toxin 12 is intended to provide direct experimental evidence for nearest neighbor amino acid contacts in the vicinity of the C13 unit. To our knowledge, this compound represents the first of any such photonaffinity-STX conjugate. (Tetrodotoxin-based photoaffinity probes have been prepared, see: (a) Guillory, R. J.; Rayner, M. D.; D'Arrigo, J. S. *Science* 1977, 196, 883. (b) Uehara, S.; Uyemura, K. *Neurochem. Res.* 1985, 10, 1119. (c) Yoshida, E.; Nakayama, H.; Hatanaka, Y.; Kanaoka, Y. *Chem. Pharm. Bull.* (Tokyo) 1990, 38, 982. (d) Nakayama, H.; Hatanaka, Y.; Yoshida, E.; Oka, K.; Takanohashi, M.; Amano, Y.; Kanaoka, Y. *Biochem. Biophys. Res. Commun.* 1992, 184, 900.)

Figure 8:
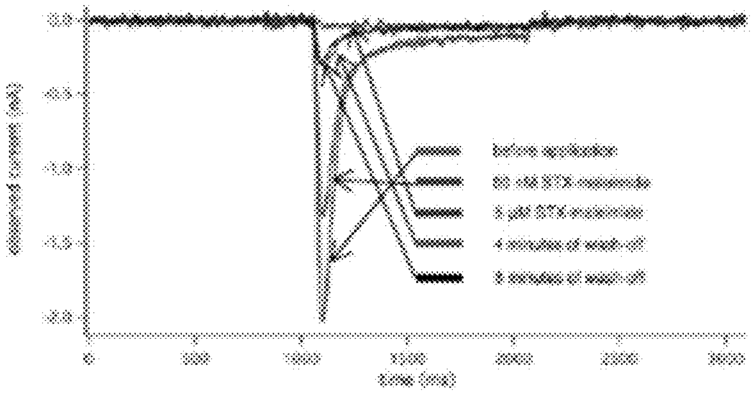
FIG. 8 shows sodium currents in the absence and in the presence of various concentrations of labeled saxitoxin analogue STX-maleimide (compound 19 shown in FIG. 7).

As a final display of the power of de novo synthesis to provide novel forms of STX, we have exploited compounds such as 10 for "post-synthetic" modification (FIG. 6). The presence of two guanidinium groups notwithstanding 10 undergoes selective coupling with an N-hydroxysuccimide (NHS) benzoate ester to give the desired amide 13. This final-step coupling reaction makes possible the attachment of structurally complex payloads to the STX core (i.e., fluorogenic groups, biomarkers), side chain elements that otherwise would be incompatible with the chemistries employed for guandine deprotection and/or C12 oxidation (see FIG. 4). To date we have attached structurally diverse fluorophores (14, 15, 16 in FIG. 7), a biotin tag (17), a diazirine species for photoaffinity labeling (18), cysteine-reactive functional groups (19), and lipophilic steroids such as cholesterol (20) to STX through coupling reactions performed on 10. The maleimide-containing compound 19 is a particularly interesting species, as it appears to irreversibly inhibit the voltage-gated sodium channel (see FIG. 8).

Access to (+)-STX through asymmetric total synthesis has empowered the development of unnatural analogues of this unique natural product. New saxitoxin analogues have been evaluated for their efficacy in blocking $Na_V$ function using whole cell, voltage-clamp techniques. These findings have revealed opportunities for re-engineering the C13-carbamoyl unit of STX with any one of a number of different structural groups. Studies of this type together with the tools of molecular biology allow researchers to map in greater detail the three-dimensional structure of the channel pore. We view these studies as a necessary step in a larger plan to utilize designed chemical tools to interrogate dynamic processes associated with $Na_V$ function.

Materials and Methods.

All reagents were obtained commercially unless otherwise noted. Reactions were performed using oven-dried glassware under an atmosphere of nitrogen. Air- and moisture sensitive liquids and solutions were transferred via syringe or stainless steel cannula. Organic solutions were concentrated under reduced pressure (ca. 15 Torr) by rotary evaporation. Dichloromethane, tetrahydrofuran (THF) and acetonitrile (MeCN) and N,N-dimethylformamide were passed through two columns of activated alumina immediately prior to use. Pyridine was distilled from calcium hydride. N-Boc-L-Serine methyl ester was prepared according to the procedure of Dondone. (see, Dondoni, A.; Perrone, D. Synthesis of 1,1-Dimethylethyl (s)-4-Formyl-2,2-Dimethyl-3-Oxazolidinecarboxylate by Oxidation of the Alcohol. *Org. Syn.* 2004, 10, 64-70.) N-(p-Methoxybenzyl)hydroxylamine was prepared in two steps according to the procedures of Quan and Baldwin. (see, (a) Quan, C.; Kurth, M. Solid-Phase Synthesis of 5-Isoxazol-4-yl-[1,2,4]oxaciazoles. *J. Org. Chem.* 2004, 69, 1470-1474. (b) Baldwin, J. E.; Cah, J. K.; Kruse, L. I. Total Synthesis of Antitumor Agent AT-125, (aS,5S)-a-Amino-3-Chloro-4,5-Dihydro-5-Isoxazolieacetic Acid. *Tetrahedron* 1985, 41, 5241-5260.) β-Saxitoxinol and saxitoxin were prepared according to the procedure of Fleming (see, Fleming, J. J.; Du Bois, J. A synthesis of (+)-saxitoxin. *J. Am. Chem. Soc.* 2006, 128, 3926-3927.) t-Butyl-6-aminohexylcarbamate was prepared according to the procedure of Phanstiel. (see, Gardner, R. A.; Ghobrial, G.; Nasser, S. A.; Phanstiel, O., IV Synthesis and Biological Evaluation of New Acinetoferrin Homologues for Use as Iron Transport Probes in Mycobacteria. *J. Med. Chem.* 2004, 47, 4933.) t-Butyl-2-aminoethylcarbamate was prepared according to the procedure of Dijkgraaf. (Dijkgraaf, I.; Rijnders, A. Y.; Soede, A.; Dechesne, A. C.; van Esse, G. W.; Brouwer, A. J.; Corstens, F. H.; Boerman, O. C.; Rijkers, D. T.; Liskamp, R. M. Synthesis of DOTA-Conjugated Multivalent Cyclic-RGD Peptide Dendrimers via 1,3-Dipolar Cycloaddition and their Biological Evaluation: Implications for Tumor Targeting and Tumor Imaging Purposes. *Org. Biomolec. Chem.* 2007, 5, 935-944.) Boron tris(trifluoroacetate) was prepared as described by Bauer as a 0.5 M solution in trifluoroacetic acid and stored in a Schlenk flask at −5° C. (see, e.g., Pless, J.; Bauer, W. Boron Tris(Trifluoroacetate) for Removal of Protecting Groups in Peptide Chemistry. *Angew. Chem., Int. Ed.* 1973, 12, 147-148.) Chromatographic purification of products was accomplished using forced flow chromatography on Silicycle ultrapure silica gel (40-63 μm). Semi-preparative high performance liquid chromatography (HPLC) was performed on a Varian ProStar model 320. Thin layer chromatography was performed on EM Science silica gel 60 F254 plates (250 μm). Visualization of the developed chromatogram was accomplished by fluorescence quenching and by staining with aqueous ceric ammonium molybdate (CAM) solution.

Nuclear magnetic resonance (NMR) spectra were acquired on a Varian Mercury spectrometer operating at 400 and 100 MHz for $^1$H and $^{13}$C, respectively, or on a Varian Inova spectrometer operating at 500 and 125 MHz for $^1$H and $^{13}$C, respectively, and are referenced internally according to residual solvent signals. Data for $^1$H NMR are recorded as follows: chemical shift (δ, ppm), multiplicity (s, singlet; d, doublet; t, triplet; q, quartet; quint, quintet; m, multiplet; br, broad), integration, coupling constant (Hz). Data for $^{13}$C NMR are reported in terms of chemical shift (δ, ppm). Infrared (IR) spectra were recorded as thin films using NaCl plates on a Thermo-Nicolet 300 FT-IR spectrometer and are reported in frequency of absorption. Optical rotation data were obtained from samples loaded into a 50 mm cell on a Jasco DIP-1000 digital polarimeter operating at the Na D-line. High-resolution mass spectra were obtained from the Vincent Coates Foundation Mass Spectrometry Laboratory at Stanford University.

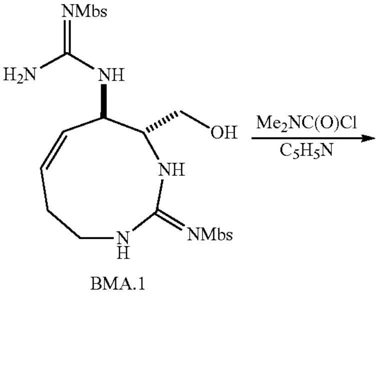

BMA.1

-continued

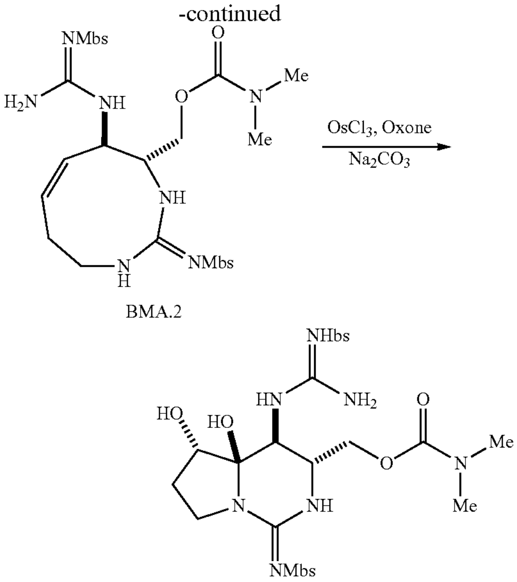

BMA.2

BMA.3

BMA.3:

To a solution of alcohol BMA.1 (155 mg, 0.27 mmol) in 5.0 mL of pyridine was added dimethylcarbamoyl chloride (555 μL, 6.0 mmol, 22 equiv). The flask was equipped with a reflux condenser and the mixture was heated to 90° C. After stirring for 12 h at this temperature, the reaction mixture was cooled to room temperature and concentrated under reduced pressure. Purification of the oily residue by chromatography on silica gel (gradient elution 96:4 $CH_2Cl_2$/MeOH→93:7 $CH_2Cl_2$/MeOH) gave the desired product BMA.2 as a white solid (65 mg, 37%). TLC $R_f$=0.55 (92:8 $CH_2Cl_2$/MeOH); $^1H$ NMR ($CD_3CN$, 400 MHz, 65° C.) δ 7.78-7.70 (m, 4H), 7.05-6.96 (m, 4H), 6.28-6.20 (m, 2H), 5.85 (br d, 1H, J=8.2 Hz), 4.82-4.74 (m, 2H), 4.67-4.63 (m, 1H), 4.20 (dd, 1H, J=11.4, 3.2 Hz), 4.11 (dd, 1H, J=11.4, 5.5 Hz), 3.92-3.87 (m, 1H), 3.88 (s, 3H), 3.86 (s, 3H), 3.49-3.36 (m, 2H), 2.89 (s, 3H), 2.84 (s, 3H), 2.69-2.61 (m, 1H), 2.20-2.10 (m, 1H) ppm. The isolated material BMA.2 (17 mg, 0.027 mmol) was dissolved in 680 μL of 11:2 MeCN/$H_2O$ to which a solution of $OsCl_3$ (36 mM in $H_2O$, 74 μL, 3.0 μmol, 0.1 equiv) was then added. To the resulting brown solution was then added 570 μL of EtOAc, a single portion of $Na_2CO_3$ (28 mg, 0.027 mmol, 10.0 equiv), and a single portion of Oxone (125 mg, 0.20 mmol, 7.6 equiv). Mild gas evolution was observed and the resulting pale yellow suspension was stirred vigorously for 60 h. The reaction was quenched by the addition of 1 mL of saturated aqueous $Na_2S_2O_3$, stirred for 5 min, and transferred to a separatory funnel containing 10 mL of EtOAc. The organic layer was collected and the aqueous layer was extracted with 10 mL of EtOAc. The organic layers were combined and washed with 5 mL of saturated aqueous NaCl, dried over $MgSO_4$, and concentrated under reduced pressure. Purification of the white residue by chromatography on silica gel (94:6 $CH_2Cl_2$/MeOH) gave BMA.3 as a white solid (4 mg, 24%) and recovered BMA.2 (10 mg, 57%). The product was obtained as a 9:1 mixture (as determined by HPLC) with the isomeric 5/6 bicycle. Additional purification of the sample was possible by reverse phase HPLC (NovaPak C18, using 30:70 MeCN/0.1% aqueous $CF_3CO_2H$ as eluent at a flow rate of 4 mL/min) Under these conditions BMA.3 eluted with a retention time of 10.1 min TLC $R_f$=0.37 (92:8

$CH_2Cl_2$/MeOH); $^1H$ NMR ($CD_3CN$, 500 MHz) δ 7.75 (s, 1H), 7.74-7.69 (m, 4H), 6.99-6.94 (m, 4H), 6.57 (br s, 2H), 6.38 (br d, 1H, J=8.9 Hz), 4.26 (br d, 1H, J=10.9 Hz), 4.02-3.99 (m, 1H), 3.91 (d, 1H, J=3.8 Hz), 3.84 (s, 6H), 3.72 (dd, 1H, J=11.1, 6.8 Hz), 3.68 (ddd, 1H, J=10.8, 6.7, 2.4 Hz), 3.57-3.47 (m, 2H), 2.85 (br s, 3H), 2.73 (br s, 3H), 2.20-2.15 (m, 1H), 1.81 (dd, 1H, J=13.4, 6.6 Hz) ppm; IR (thin film) ν 3333, 1686, 1578, 1536, 1499, 1259, 1202, 1133, 1081, 853 $cm^{-1}$; HRMS ($ES^+$) calcd for $C_{26}H_{35}N_7O_{10}S_2$ 669.1887 found 692.1783 ($MNa^+$).

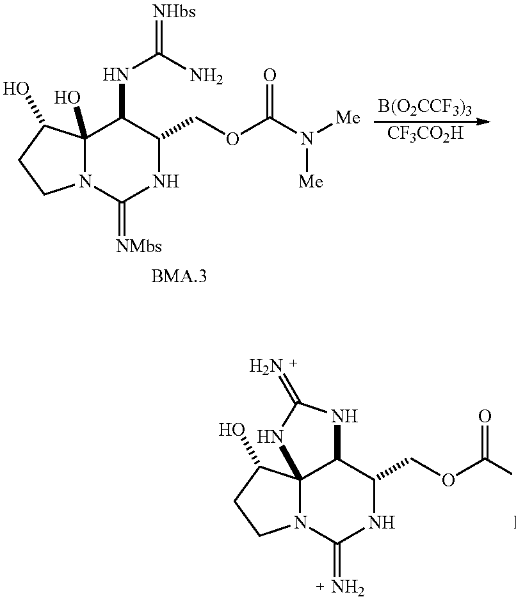

BMA.3

BMA.4
β-$NMe_2$-saxitoxinol

BMA.4:

A 0.5 M $CF_3CO_2H$ solution of $B(O_2CCF_3)_3$ (400 μL, 30 equiv) was added dropwise to a flask containing BMA.3 (4.5 mg, 6.7 μmol) that had been placed in an ice-$H_2O$ bath. The light brown mixture was stirred vigorously as the contents warmed slowly over a 5 h period to 20° C. After stirring for 14 h at this temperature, the solution was cooled to −78° C., and the reaction was quenched by the dropwise addition of 1 mL of MeOH. The solution was concentrated under reduced pressure to a solid residue, which was re-dissolved in 1 mL of MeOH. The solution was concentrated a second time. This process was repeated once. The isolated material was then dissolved in 0.5 mL of $H_2O$ and passed through a 20×100 mm column of ion-exchange resin (Dowex 1×8-200 $^-$OH form) using $H_2O$ as eluent. Fractions containing product, as determined by pH (~7.5-8.0), were collected and acidified to a pH of 2 with 20 μL of 1.0 M aqueous HCl. The solution was lyophilized to give BMA.4 as a white powder (2.0 mg, 75%). $^1H$ NMR ($D_2O$, 500 MHz) δ 4.76 (d, 1H, J=1.4 Hz), 4.31 (d, 1H, J=4.0 Hz), 4.26 (dd, 1H, J=11.5, 9.0 Hz), 4.04 (dd, 1H, J=11.5, 5.5, Hz), 3.83 (ddd, 1H, J=9.0, 5.4, 1.5 Hz), 3.74 (ddd, 1H, J=10.2, 10.2, 2.1 Hz), 3.66 (ddd, 1H, J=9.8, 9.8, 8.4 Hz), 2.91 (s, 3H), 2.86 (s, 3H), 2.39 (dddd, 1H, J=14.7, 10.2, 10.2, 4.4 Hz), 2.21 (ddd, 1H, J=15.0, 8.2, 1.5 Hz); HRMS ($ES^+$) calcd for $C_{12}H_{21}N_7O_3$ 311.1706 found 312.1782 ($MH^+$).

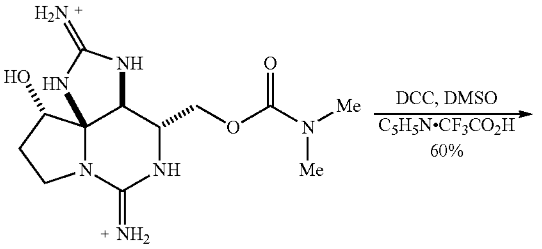

BMA.4
β-$NMe_2$-saxitoxinol

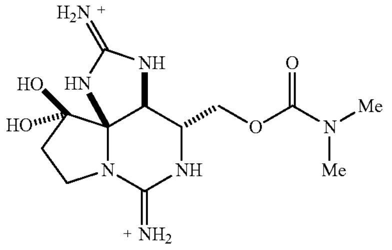

BMA.5
$NMe_2$-saxitoxin

BMA.5:

β-DMC-STX BMA.4 (2.0 mg, 5.2 μmol) and powdered 3 Å molecular sieves were combined in 500 μL of DMSO and stirred for 30 min. To this mixture were added dicyclohexylcarbodiimide (13 mg, 63 μmol, 12.1 equiv) and pyridinium trifluoroacetate (8.2 mg, 42 μmol, 8.1 equiv). A dense precipitate formed immediately, and the resulting turbid suspension was stirred vigorously for 17 h. Lyophylization of the reaction mixture furnished a solid product that was suspended in 1 mL of $H_2O$ and filtered. An additional 1 mL of $H_2O$ was used to ensure quantitative transfer of the material. The combined filtrates were lyophylized, and the isolated solid product was purified by reverse-phase HPLC (Altima C18, 10 μm, 10×250 mm column, eluting with a gradient flow over 30 min of 10:90 MeCN/10 mM aqueous $C_3F_7CO_2H$→25:75 MeCN/10 mM aqueous $C_3F_7CO_2H$, 214 nm UV detection). At a flow rate of 6 mL/min, dimethylcarbamoyl saxitoxin.2 $C_3F_7CO_2H$ had a retention time of 20.8 min and was isolated as a white, hygroscopic solid (1.2 mg, 60%). $^1H$ NMR ($D_2O$, 500 MHz) δ 4.73 (d, 1H, J=1.0 Hz), 4.29 (dd, 1H, J=11.6, 9.5 Hz), 4.03 (dd, 1H, J=11.6, 5.3 Hz), 3.84 (ddd, 1H, J=9.3, 5.2, 0.9 Hz), 3.78 (ddd, 1H, J=9.7, 9.7, 1.7 Hz), 3.55 (ddd, 1H, J=9.7, 9.7, 8.2 Hz), 2.91 (s, 3H), 2.86 (s, 3H), 2.40 (ddd, 1H, J=13.6, 7.8, 1.7 Hz), 2.32 (ddd, 1H, J=13.7, 9.7, 9.7 Hz) ppm; HRMS ($ES^+$) calcd for $C_{12}H_{19}N_7O_3$ 309.1549 found 310.1633 ($MH^+$).

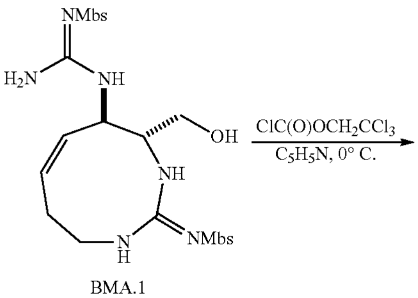

BMA.1

-continued

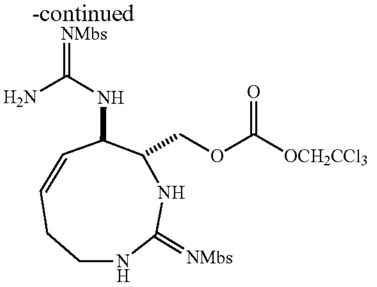

BMA.6

BMA.6:

Trichloroethylchloroformate (49 mL, 0.35 mmol) was added dropwise to an ice-cold solution of BMA.1 (200 mg, 0.35 mmol) in 3.5 mL of pyridine. A gummy solid formed immediately which slowly dissolved. After stirring the mixture for 10 min, a second portion of trichloroethylchloroformate (49 mL, 0.35 mmol, 1.0 equiv) was added. The mixture was stirred for an additional 20 min at 0° C. The reaction was then quenched by the addition of 10 mL of saturated aqueous $NaHCO_3$. The mixture was transferred to a separatory funnel with 10 mL of $CH_2Cl_2$. The organic phase was collected and the aqueous layer was extracted with 3×10 mL of $CH_2Cl_2$. The combined organic fractions were dried over $MgSO_4$, filtered, and concentrated under reduced pressure to a white solid. Purification of this material by chromatography on silica gel (94:6 $CH_2Cl_2$/MeOH) furnished BMA.6 as a white solid (244 mg, 93%). TLC $R_f$=0.34 (9:1 $CH_2Cl_2$/MeOH); $^1H$ NMR ($CD_3CN$, 500 MHz, 70° C.) δ 7.76-7.70 (m, 4H), 7.02-6.94 (m, 4H), 6.78 (br s, 1H), 6.16 (s, 2H), 5.62 (d, 1H, J=7.0 Hz), 4.87 (d, 1H, J=12.0 Hz), 4.82 (d, 1H, J=12.0 Hz), 4.82-4.76 (m, 1H), 4.64 (br s, 1H), 4.61 (dd, 1H, J=7.5, 7.5 Hz), 4.31 (dd, 1H, J=18.0, 11.0 Hz), 4.28 (ddd, 1H, J=11.5, 11.5, 3.5 Hz), 4.00-3.92 (m, 1H), 3.85 (s, 3H), 3.84 (s, 3H), 3.48-3.34 (m, 2H), 2.74-2.64 (m, 1H), 2.19-2.12 (m, 1H) ppm; IR (thin film) ν 3333, 1764, 1597, 1531, 1499, 1255, 1131, 1081 $cm^{-1}$; HRMS ($ES^+$) calcd for $C_{26}H_{31}N_6O_9S_2$ 740.0481 found 763.0546 ($MNa^+$).

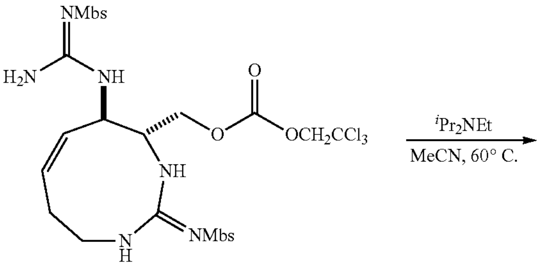

BMA.6

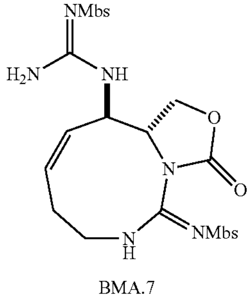

BMA.7

BMA.7:

Diisopropylethylamine (535 mL, 3.1 mmol, 10.0 equiv) was added to a suspension of BMA.6 (228 mg, 0.31 mmol) in 6.0 mL of MeCN and the mixture was stirred at 60° C. for 12 h, during which time the solid material dissolved. The reaction was cooled to room temperature and the solution was concentrated under reduced pressure to give an off-white solid. The unpurified material was triturated with 5 mL of $Et_2O$; the off-white solids were collected upon filtration and washed with 5 mL of ice cold $Et_2O$ to furnish 2.54 (156 mg, 86%). TLC $R_f$=0.34 (9:1 $CH_2Cl_2$/MeOH); $^1H$ NMR ($CD_3CN$, 500 MHz) δ 7.80 (dd, 2H, J=7.0, 2.0 Hz), 7.70 (dd, 2H, J=7.0, 2.0 Hz), 7.04 (dd, 2H, J=7.0, 2.0 Hz), 6.95 (dd, 2H, J=7.0, 2.0 Hz), 6.25 (br s, 2H), 5.66 (br s, 1H), 4.73 (ddd, 1H, J=14.5, 11.0, 5.0 Hz), 4.66 (br s, 1H), 4.61 (dd, 1H, J=11.0, 7.5 Hz), 4.38 (dd, 1H, J=8.0, 8.0 Hz), 4.22 (ddd, 1H, J=10.0, 10.0, 1.5 Hz), 4.14 (dd, 1H, J=9.0, 2.5 Hz), 3.85 (s, 3H), 3.82 (s, 3H), 3.61 (ddd, 1H, J=14.5, 7.5, 3.0 Hz), 3.40 (m, 1H), 2.55-2.46 (m, 1H), 2.23-2.17 (m, 1H) ppm; IR (thin film) ν 3326, 3307, 1776, 1596, 1533, 1499, 1398, 1259, 1138, 1084 $cm^{-1}$; HRMS ($ES^+$) calcd for $C_{24}H_{28}N_6O_8S_2$ 592.1410 found 615.1308 ($MNa^+$).

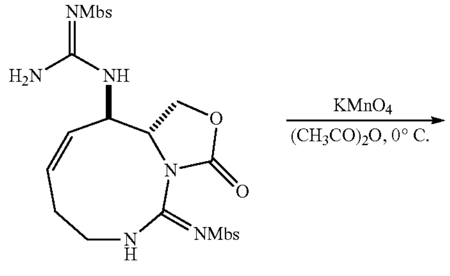

BMA.7

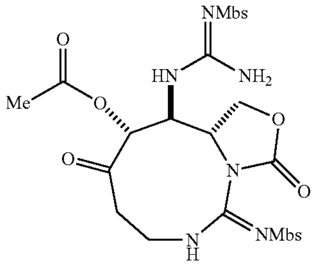

BMA.8

BMA.8:

To an ice-cold solution of BMA.7 (20 mg, 0.034 mmol) in 1 mL of acetic anhydride was added solid $KMnO_4$ (11 mg, 0.067 mmol, 2.0 equiv). The bright purple solution was stirred for 4 h at 0° C. The reaction was then quenched by addition of 2 mL of saturated aqueous $Na_2S_2O_3$ and diluted with 5 mL of EtOAc and 5 mL of $H_2O$. The mixture was transferred to a separatory funnel and the organic layer was collected. The aqueous layer was extracted with 3×5 mL EtOAc. The combined organic layers were washed with 10 mL of saturated aqueous NaCl, dried over $MgSO_4$, filtered, and concentrated under reduced pressure to an oily residue. Purification of this material by chromatography on silica gel (95:5 $CH_2Cl_2$/MeOH) furnished acetate BMA.8 as a white solid (12 mg, 53%). TLC $R_f$=0.40 (9:1 $CH_2Cl_2$/MeOH); $^1H$ NMR ($CD_3CN$, 400 MHz) δ 8.23 (br s, 1H), 7.84-7.80 (m, 2H), 7.75-7.71 (m, 2H), 7.06-7.03 (m, 2H), 6.98-6.94 (m, 2H), 6.48 (br s, 2H), 6.04 (d, 1H, J=6.0 Hz), 5.18 (d, 1H, J=4.0 Hz), 4.65 (ddd, 1H, J=8.8, 7.2, 2.4 Hz), 4.48 (s, 1H), 4.46 (d, 1H, J=1.2 Hz), 4.35 (ddd, 1H, J=6.4, 4.0, 2.8 Hz), 3.85 (s, 3H), 3.83-3.78 (m, 1H), 3.82 (s, 3H), 3.56-3.50 (m, 1H), 2.66 (dd, 2H, J=6.8, 5.2 Hz), 2.07 (s, 3H) ppm; IR (thin film) ν 3447, 3356, 1783, 1720, 1621, 1597, 1525, 1500, 1399, 1260, 1138, 1082, 836 $cm^{-1}$; HRMS ($ES^+$) calcd for $C_{25}H_{28}N_6O_{12}S_2$ 668.1207 found 689.1312 ($MNa^+$).

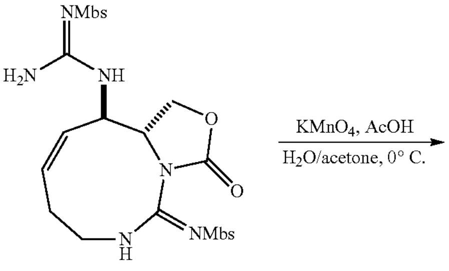

BMA.7

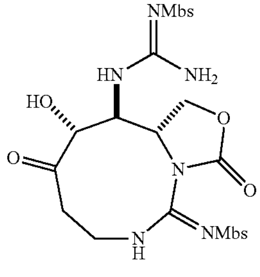

BMA.9

BMA.9:

To an ice-cold solution of BMA.7 (20 mg, 34.0 μmol) in 976 μL of a 50:10:1 acetone/$H_2O$/AcOH solution was added $KMnO_4$ (11 mg, 67.0 μmol, 2.0 equiv). After stirring at 0° C. for 2.5 h, the reaction was quenched by the addition of 2 mL of saturated aqueous $Na_2S_2O_3$. The mixture was diluted with 5 mL of EtOAc and 5 mL of $H_2O$ and transferred to a separatory funnel. The organic layer was collected and the aqueous layer was extracted with 3×5 mL of EtOAc. The combined organic layers were washed with 3×10 mL of saturated aqueous $NaHCO_3$, 1×10 mL of saturated aqueous NaCl, dried over $MgSO_4$, and concentrated under reduced pressure. Purification of the isolated material by chromatography on silica gel furnished ketoalcohol BMA.9 as a white solid (11 mg, 54%). TLC $R_f$=0.36 (9:1 $CH_2Cl_2$/MeOH); $^1H$ NMR ($CD_3CN$, 500 MHz) δ 8.18 (br s, 1H), 7.81-7.78 (m, 2H), 7.76-7.73 (m, 2H), 6.43 (br s, 2H), 6.03 (d, 1H, J=6.0 Hz), 4.57 (dd, 1H, J=6.0, 6.0 Hz), 4.50 (ddd, 1H, J=6.0, 6.0, 2.0 Hz), 4.47-4.42 (m, 1H), 4.32-4.29 (m, 1H), 4.24 (ddd, 1H, J=6.5, 5.0, 1.5 Hz), 3.90 (ddd, 1H, J=14.5, 9.0, 3.0 Hz), 3.85 (s, 3H), 3.82 (s, 3H), 3.57 (ddd, 1H, J=15.0, 6.5, 4.5 Hz), 2.89 (ddd, 1H, J=14.0, 6.0, 3.0 Hz), 2.59 (ddd, 1H, J=14.0, 9.5, 4.0 Hz) ppm; IR (thin film) ν 3363, 1784, 1691, 1614, 1539, 1403, 1262, 1135, 1075, 833, 763 $cm^{-1}$.

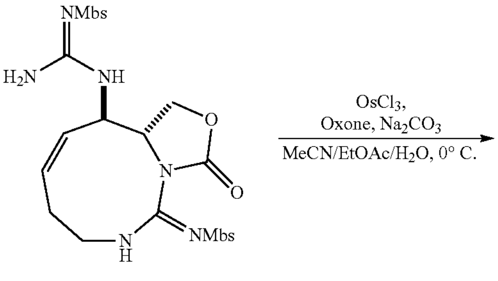

BMA.9

-continued

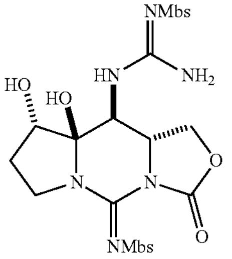

BMA.10

BMA.10:

Oxone (436 mg, 0.71 mmol, 7.0 equiv) was added in a single portion to a mixture of $OsCl_3$ (36 mM solution in $H_2O$, 282 mL, 0.010 mmol, 0.10 equiv) and $Na_2CO_3$ (107 mg, 1.0 mmol, 10 equiv) in 4.3 mL of a 3:3:1 mixture of EtOAc/MeCN/$H_2O$. Mild gas evolution was observed and the resulting off-white mixture suspension was stirred for 2 min before oxazolidinone BMA.9 (60 mg, 0.10 mmol) was added. The contents were stirred vigorously for 48 h. The reaction was then quenched by the addition of 5 mL of saturated $Na_2S_2O_3$ and the mixture was transferred to a separatory funnel containing 10 mL of $H_2O$ and 20 mL of EtOAc. The organic layer was collected and the aqueous phase was extracted with 3×15 mL of EtOAc. The combined organic extracts were washed with 10 mL of saturated aqueous NaCl, dried over $MgSO_4$, and concentrated under reduced pressure. The solid residue was purified by chromatography on silica gel (92:8 $CH_2Cl_2$/MeOH) to give BMA.10 as a white solid (28 mg, 44%). TLC $R_f$=0.21 (9:1 $CH_2Cl_2$/MeOH); $^1H$ NMR ($CD_3CN$, 500 MHz) δ 7.80-7.76 (m, 4H), 7.01-6.95 (m, 4H), 6.51 (br s, 2H), 6.07 (br s, 1H), 4.83 (br s, 1H), 4.46-4.40 (m, 2H), 4.32 (br s, 1H), 4.12 (d, 1H, J=6.0 Hz), 3.92 (d, 1H, J=3.5 Hz), 3.83 (s, 3H), 3.81 (s, 3H), 3.81-3.75 (m, 1H), 3.44 (ddd, 1H, J=12.0, 12.0, 2.0 Hz), 2.25 ($^1H$, signal obscured by DHO), 1.84 (dd, 1H, J=12.5, 7.5 Hz) ppm; IR (thin film) ν 3326, 3307, 1776, 1596, 1533, 1499, 1398, 1259, 1138, 1084 $cm^{-1}$; HRMS ($ES^+$) calcd for $C_{24}H_{28}N_6O_{10}S_2$ 624.1308 found 625.1359 ($MH^+$).

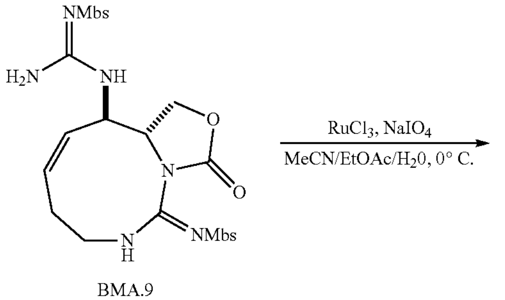

BMA.9

-continued

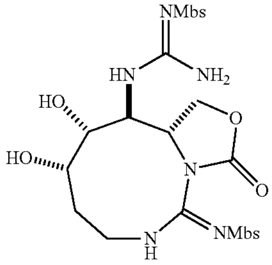

BMA.11

BMA.11:

To an ice-cold solution of BMA.9 (30 mg, 51.0 μmol) in 2.5 mL of a 2:2:1 EtOAc/MeCN/$H_2O$ solution was added $RuCl_3$ (0.53 mg, 2.5 μmol, 0.05 equiv) followed by solid $NaIO_4$ (13.1 mg, 61.2 mmol, 1.2 equiv). The reaction was stirred for 45 min at 0° C., then quenched by addition of 2 mL of saturated aqueous $Na_2S_2O_3$. The reaction was diluted with 5 mL of EtOAc and 5 mL of $H_2O$ and transferred to a separatory funnel. The organic layer was collected and the aqueous layer was extracted with 3×5 mL of EtOAc. The combined organic fractions were washed with 10 mL of saturated aqueous NaCl, dried over $MgSO_4$, filtered and concentrated under reduced pressure. Purification of the isolated material by chromatography on silica furnished diol BMA.11 as a white solid (23 mg, 72%). TLC $R_f$=0.30 (9:1 $CH_2Cl_2$/MeOH); $^1H$ NMR ($CD_3CN$, 400 MHz) δ 7.90 (br s, 1H), 7.82-7.79 (m, 2H), 7.76-7.73 (m, 2H), 7.06-7.02 (m, 2H), 7.00-6.96 (m, 2H), 6.36 (br s, 2H), 5.67 (br d, 1H, J=3.6 Hz), 4.57-4.52 (m, 1H), 4.31 (dd, 1H, J=11.2, 5.6 Hz), 4.30-4.27 (m, 1H), 3.88-3.79 (m, 1H), 3.84 (s, 3H), 3.82 (s, 3H), 3.73-3.64 (m, 2H), 3.45-3.37 (m, 1H), 3.32-3.17 (m, 2H), 1.91-1.81 (m, 1H), 1.70-1.61 (m, 1H) ppm; IR (thin film) ν 3325, 1767, 1618, 1596, 1534, 1499, 1400, 1260, 1134, 1083 $cm^{-1}$.

A general three-step protocol was used to transform oxazolidinone BMA.10 into STX derivatives BMA.14-BMA.18. Experimental details for the conversion of BMA.10 to BMA.14 are representative.

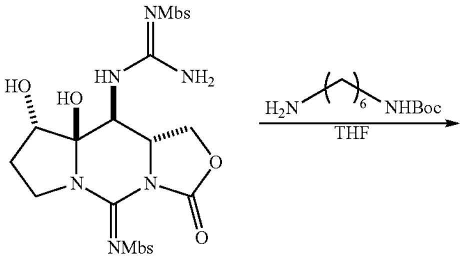

BMA.10

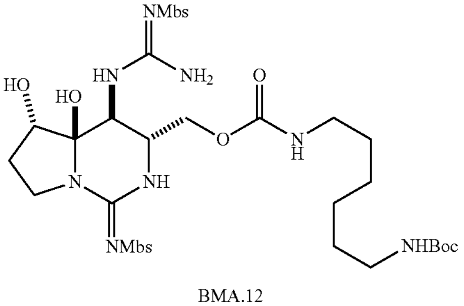

BMA.12

BMA.12:

t-Butyl-6-aminohexylcarbamate (28 mg, 0.13 mmol, 5.0 equiv) was added to a solution of BMA.10 (16 mg, 26.0 μmol) in 1.3 mL of THF. The mixture was stirred for 4 h, concentrated under reduced pressure, and the isolated material was purified by chromatography on silica gel (94:6 $CH_2Cl_2$/MeOH) to give BMA.12 as a colorless oil (22 mg, 99%). TLC $R_f$=0.30 (9:1 $CH_2Cl_2$/MeOH); $^1H$ NMR ($CD_3CN$, 500 MHz, 60° C.) δ 7.75 (dd, 4H, J=9.0, 1.5 Hz), 6.98 (dd, 4H, J=9.0, 2.5 Hz), 6.37 (br s, 2H), 5.81 (br s, 1H), 5.53 (br s, 1H), 5.11 (br s, 1H), 4.81 (br s, 1H), 4.29 (br d, 1H, J=11.5 Hz), 4.13 (s, 1H), 4.03 (br t, 1H, J=8.0 Hz), 3.94 (t, 1H, J=3.5 Hz), 3.85 (s, 6H), 3.75 (dd, 1H, J=12.0, 4.5 Hz), 3.67-3.63 (m, 1H), 3.58-3.50 (m, 2H), 3.07 (br s, 2H), 2.99 (ddd, 2H, J=6.5, 6.5, 6.5 Hz), 2.23-2.16 (m, 1H), 1.85-1.81 (m, 1H), 1.51-1.40 (m, 4H), 1.42 (s, 9H), 1.34-1.25 (m, 4H) ppm; IR (thin film) ν 3330, 2932, 1701, 1578, 1535, 1499, 1256, 1132, 1082 $cm^{-1}$; HRMS ($ES^+$) calcd for $C_{35}H_{52}N_8O_{12}S_2$ 840.3146 found 863.3033 ($MNa^+$).

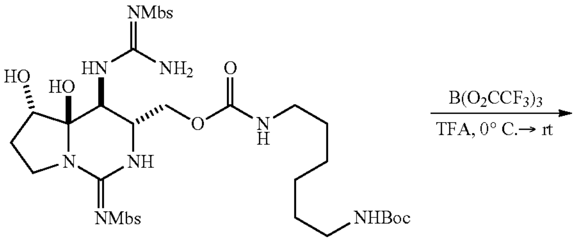

BMA.12

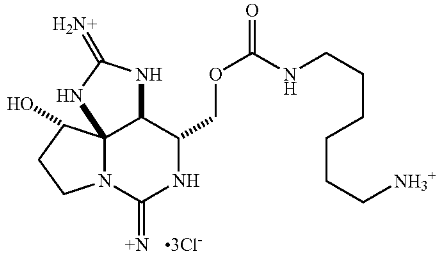

BMA.13

BMA.13:

A 10 mL round bottom flask containing BMA.12 (23 mg, 0.027 mmol) was placed in an ice bath, and to it was slowly added $B(O_2CCF_3)_3$ (0.5 M solution in $CF_3CO_2H$, 1.64 mL, 0.82 mmol, 30 equiv). The resulting light brown solution was stirred and slowly warmed to room temperature over 5 h. After stirring for an additional 14 h at this temperature, the solution was cooled to 0° C., and the reaction quenched by the dropwise addition of 1.0 mL of MeOH. The mixture was concentrated under reduced pressure to an oily residue. The unpurified product was re-dissolved in ~2 mL of MeOH and the solution was concentrated. This process was repeated once. The isolated material was then dissolved in 1 mL of $H_2O$ and passed through a 2×10 cm column of Dowex 1×8-200 ($^-$OH form). The fractions containing product, as determined by pH (>7.5), were collected and acidified with 100 mL of 1.0 M aqueous HCl. The solution was lyophilized to give BMA.13 as a white powder (12 mg, 92%). $^1H$ NMR ($D_2O$, 400 MHz) δ 4.77 (d, 1H, J=1.2 Hz), 4.33 (d, 1H, J=3.6 Hz), 4.26 (dd, 1H, J=11.6, 9.2 Hz), 4.01 (dd, 1H, J=11.6, 5.6 Hz), 3.81 (dd, 1H, J=9.2, 5.6 Hz), 3.77 (ddd, 1H, J=10.0, 10.0, 2.0 Hz), 3.67 (ddd, 1H, J=18.8, 8.8, 1.6 Hz), 3.15-3.05 (m, 2H), 2.97 (dd, 2H, J=7.6, 7.6 Hz), 2.46-2.36, (m, 1H), 2.23 (ddd, 1H, J=14.8, 8.4, 1.6 Hz), 1.68-1.61 (m, 2H), 1.52-1.45 (m, 2H), 1.41-1.31 (m, 4H) ppm; HRMS ($ES^+$) calcd for $C_{16}H_{30}N_8O_3$ 382.2441 found 383.2514 ($MH^+$).

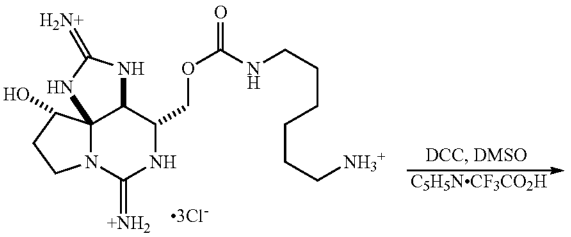

BMA.13

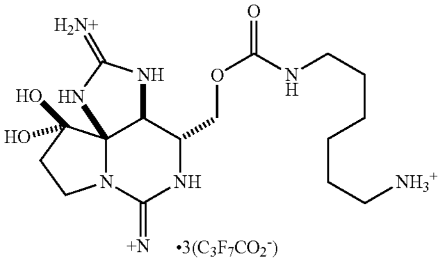

BMA.14

BMA.14:

To a solution of BMA.13 (9 mg, 0.018 mmol) in 1.4 mL of DMSO was added powdered 3 Å molecular sieves. The suspension was stirred for 20 min prior to the addition of dicyclohexylcarbodiimide (45 mg, 0.22 mmol, 12 equiv) and pyridinium trifluoroacetate (27 mg, 0.14 mmol, 7.5 equiv). A white precipitate formed immediately; the slurry was stirred vigorously for 17 h. Lyophylization of the reaction mixture furnished a solid product that was suspended in 1 mL of $H_2O$ and filtered through a short pad of Celite. An additional 2×1 mL of $H_2O$ was used to ensure quantitative transfer of the material. The combined filtrates were lyophilized and the isolated solid was purified by reverse phase HPLC (Altima C18, 10 μm, 10×250 mm column, eluting with a gradient flow over 14 min of 20:80 MeCN/10 mM aqueous $C_3F_7CO_2H$→27:73 MeCN/10 mM aqueous $C_3F_7CO_2H$, 214 nm UV detection). At a flow rate of 6 mL/min, BMA.14 had a retention time of 7.1 min, and was isolated following lyophylization as a white powder (12 mg, 63%). $^1H$ NMR ($D_2O$, 500 MHz) δ 4.68 (s, 1H), 4.23 (dd, 1H, J=11.5, 9.5 Hz), 3.97 (dd, 1H J=11.5, 5.5 Hz), 3.78-3.74 (m, 2H), 3.52 (ddd, 1H, J=18.5, 8.5, 1.5 Hz), 3.09-3.01 (m, 2H), 2.93 (dd, 2H, J=6.4, 6.4 Hz), 2.38 (ddd, 1H, J=14.0, 8.0, 2.0 Hz), 2.33-2.26 (m, 1H), 1.63-1.57 (m, 2H), 1.48-1.42 (m, 2H), 1.35-1.28 (m, 4H) ppm; HRMS ($ES^+$) calcd for $C_{16}H_{30}N_8O_4$ 398.2390 found 399.2472 ($MH^+$).

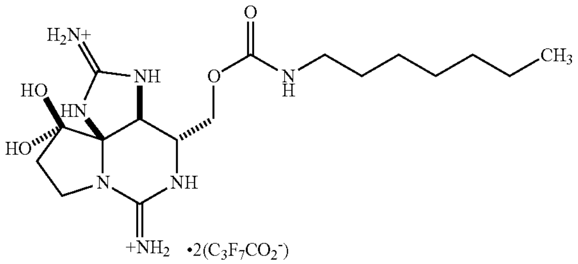

BMA.15

BMA.15:

$^1H$ NMR ($D_2O$, 400 MHz) δ 4.70 (s, 1H), 4.27 (dd, 1H, J=11.6, 8.8 Hz), 3.99 (dd, 1H, J=11.6, 5.2 Hz), 3.80-3.76 (m,

2H), 3.54 (dd, 1H, J=7.6, 7.6 Hz), 3.11-3.04 (m, 2H), 2.39-2.30 (m, 2H), 1.45 (dd, 2H, J=6.8, 6.8 Hz), 1.26-1.21 (m, 8H), 0.83 (t, 3H, J=6.8 Hz) ppm; HRMS ($ES^+$) calcd for $C_{17}H_{31}N_7O_4$ 397.2438 found 398.2505 ($MH^+$).

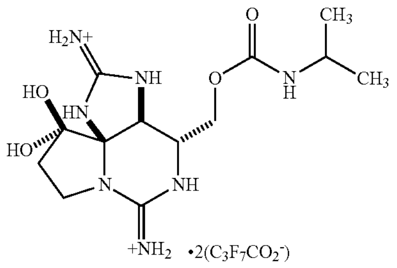

BMA.16

BMA.16:

$^1$H NMR ($D_2O$, 500 MHz) δ 4.70 (s, 1H), 4.26 (dd, 1H, J=11.5, 9.0 Hz), 3.99-3.95 (m, 1H), 3.80-3.75 (m, 2H), 3.66-3.60 (m, 1H), 3.54 (ddd, 1H, J=18.0, 10.0, 1.5 Hz), 2.40 (ddd, 1H, J=14.0, 8.0, 1.5 Hz), 2.34-2.28 (m, 1H), 1.09 (d, 6H, J=7.0 Hz) ppm; HRMS ($ES^+$) calcd for $C_{13}H_{23}N_7O_4$ 341.1812 found 342.1890 ($MH^+$).

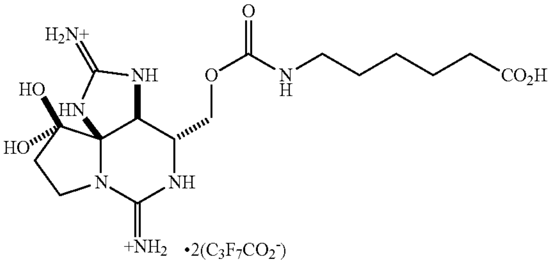

BMA.17

BMA.17:

$^1$H NMR ($D_2O$, 500 MHz) δ 4.69 (d, 1H, J=1.5 Hz), 4.27 (dd, 1H, J=12.0, 9.5 Hz), 3.97 (dd, 1H, J=11.5, 5.0 Hz), 3.78-3.71 (m, 2H), 3.52 (dd, 1H, J=9.0, 9.0 Hz), 3.08 (dd, 2H, J=6.5, 6.5 Hz), 2.15 (t, 2H, J=7.0 Hz), 1.55-1.49 (m, 2H), 1.49-1.43 (m, 2H), 1.31-1.23 (m, 2H) ppm (note: $^1$H signals for C11 methylene are absent due to exchange with $D_2O$); HRMS ($ES^+$) calcd for $C_{16}H_{27}N_7O_6$ 413.2023 found 414.2122 ($MH^+$).

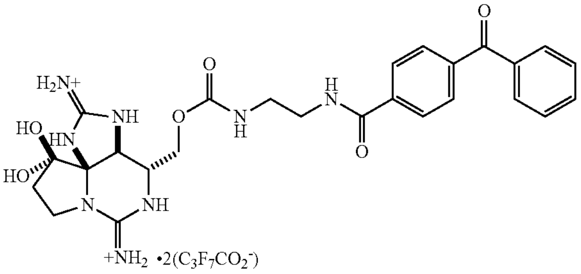

BMA.18

BMA.18:

$^1$H NMR ($D_2O$, 400 MHz) δ 7.87 (d, 2H, J=9.2 Hz), 7.85 (d, 2H, J=9.2 Hz), 7.81 (dd, 2H, J=8.0, 1.2 Hz), 7.73 (tt, 1H, J=7.6, 1.6 Hz), 7.57 (t, 2H, J=8.0 Hz), 4.64 (d, 1H, J=1.2 Hz), 4.17 (dd, 1H, J=11.6, 9.6 Hz), 3.96 (dd, 1H, J=11.6, 4.8 Hz), 3.74-3.69 (m, 2H), 3.53 (dd, 2H, J=5.2, 5.2 Hz), 3.41-3.34 (m, 3H), 2.34-2.26 (m, 2H) ppm; HRMS ($ES^+$) calcd for $C_{26}H_{30}N_8O_6$ 550.2288 found 551.2388 ($MH^+$).

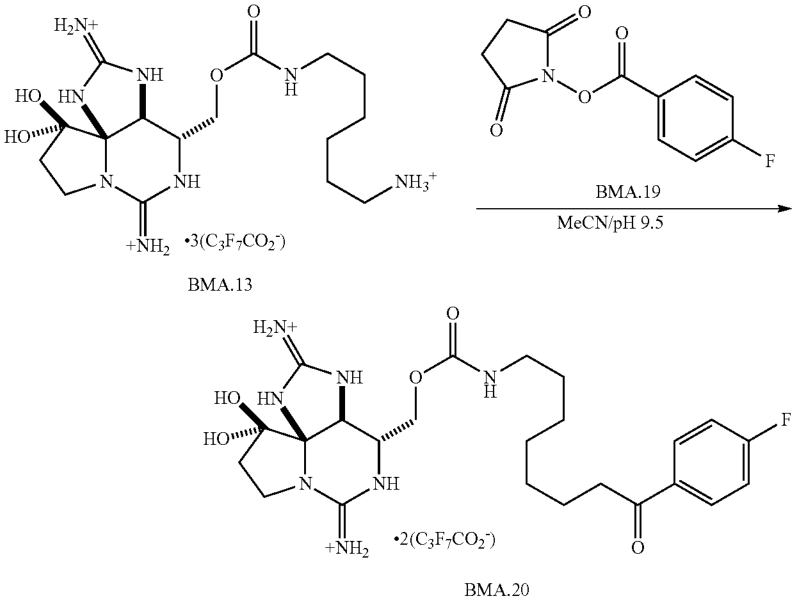

BMA.13 BMA.19

BMA.20

BMA.20:

To a solution of BMA.13 (2.5 mg, 2.4 mmol) in 240 μL of a 1:3 mixture of pH 9.5 buffer (0.1 M $NaHCO_3/Na_2CO_3$) and DMF was added 4-fluorobenzoic acid N-hydroxysuccinimide ester (1.6 mg, 7.2 mmol, 3.0 equiv). The solution was stirred for 5 h at room temperature, then acidified with 30 mL of 1.0 M aqueous HCl. The mixture was lyophilized to give a solid material that was purified by reverse phase HPLC (Altima C18, 10 μm, 10×250 mm column, eluting with a gradient flow over 30 min of 10:90 MeCN/10 mM aqueous $C_3F_7CO_2H$→40:60 MeCN/10 mM aqueous $C_3F_7CO_2H$, 254 nm UV detection). At a flow rate of 6 mL/min, BMA.20 had a retention time of 16.2 min and was isolated following lyophylization as a white powder (2.2 mg, 96%). $^1$H NMR ($D_2O$, 500 MHz) δ 7.75-7.72 (m, 2H), 7.21-7.18 (m, 2H), 4.68 (s, 1H), 4.21 (dd, 1H, J=12.0, 9.5 Hz), 3.84 (dd, 1H, J=12.0, 5.5 Hz), 3.78-3.74 (m, 2H), 3.54-3.49 (m, 1H), 3.34 (dd, 2H, J=7.0, 7.0 Hz), 3.10-3.03 (m, 2H), 2.40-2.26 (m, 2H), 1.61-1.55 (m, 2H), 1.48-1.43 (m, 2H), 1.38-1.28 (m, 4H) ppm; HRMS ($ES^+$) calcd for $C_{23}H_{33}FN_8O_5$ 520.2558 found 521.2639 ($MH^+$).

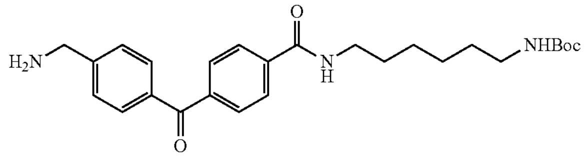

BMA.21

TLC $R_f$=0.08 (9:1 $CH_2Cl_2$/MeOH); $^1$H NMR ($CDCl_3$, 400 MHz) δ 7.91 (d, 2H, J=8.0 Hz), 7.81-7.75 (m, 4H), 7.43 (d, 2H, J=8.4 Hz), 6.78 (br s, 1H), 4.63 (br s, 1H), 3.96 (s, 2H), 3.45 (q, 2H, J=6.8 Hz), 3.11 (q, 2H, J=6.4 Hz), 1.66-1.57 (m, 4H), 1.51-1.32 (m, 4H) ppm; IR (thin film) ν 3361, 3305, 2931, 2859, 1686, 1648, 1523, 1280, 1174, 932 $cm^{-1}$.

BMA.23:

To a stirred solution of BMA.22 (4.0 mg, 4.1 μmol) in 200 μL of a 1:1 mixture of MeCN and pH 9.5 buffer ($NaHCO_3/Na_2CO_3$) was added biotin NHS ester (2.1 mg, 6.2 μmol, 1.5 equiv). The mixture was stirred for 6 h, after which time the reaction was quenched with 21 μL of 1.0 M aqueous HCl and the solvent was removed under reduced pressure. Purification of this isolated material by reverse phase HPLC (Altima C18, 10 μm, 10×250 mm column, eluting with a gradient flow over 30 min of 20:80 MeCN/$H_2O$ containing 0.1% aqueous $CF_3CO_2H$→80:20 MeCN/$H_2O$ containing 0.1% aqueous $CF_3CO_2H$, 254 nm UV detection). At a flow rate of 6 mL/min, BMA.23 had a retention time of 89 min and was isolated following lyophylization as a white powder (0.71 mg, 20%): $^1$H NMR ($D_2O$, 400 MHz) δ 7.84 (s, 4H), 7.79 (d, 2H, J=8.0 Hz), 7.46 (d, 2H, J=7.6 Hz), 4.72 (s, 1H), 4.47 (dd, 1H, J=7.6, 5.2 Hz), 4.40 (d, 2H, J=6.0 Hz), 4.31-4.27 (m, 2H), 4.05 (dd, 1H, J=12.0, 5.2 Hz), 3.83-3.74 (m, 2H), 3.56-3.49 (m, 1H), 3.39 (t, 2H, J=6.8 Hz), 3.21-3.13 (m, 3H), 2.85 (dd, 1H, J=12.8, 4.8 Hz), 2.63 (d, 1H, J=13.2 Hz), 2.42-2.26 (m, 2H), 2.14 (t, 2H, J=7.2 Hz), 1.65-1.57 (m, 4H), 1.55-1.44 (m, 4H), 1.39-1.26 (m, 6H) ppm.

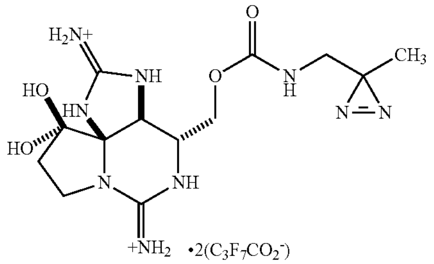

BMA.24

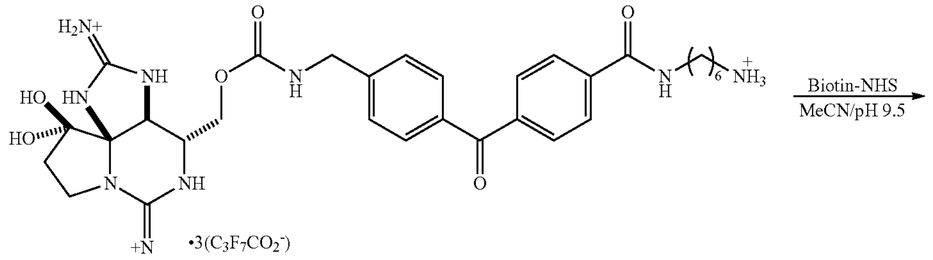

BMA.22

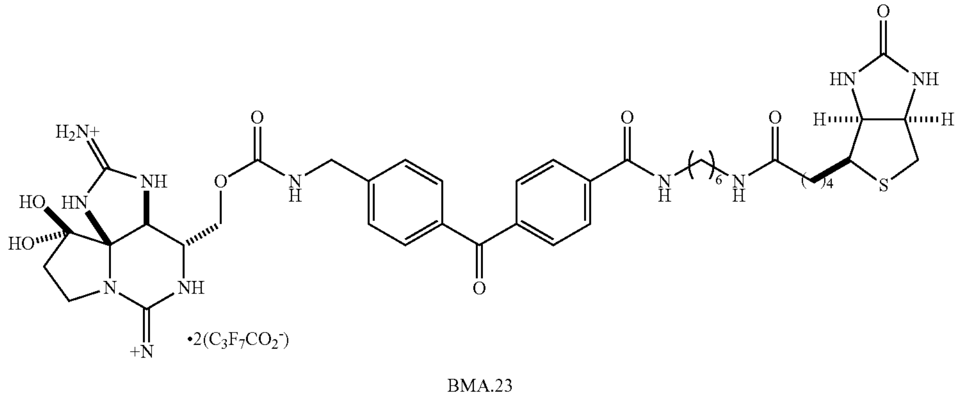

BMA.23

$^1$H NMR ($D_2O$, 400 MHz) δ 4.68 (s, 1H), 4.28 (dd, 1H, J=11.6, 9.6 Hz), 3.96 (dd, 1H, J=12.0, 5.2 Hz), 3.78 (ddd, 1H, J=10.0, 10.0, 2.0 Hz), 3.77-3.74 (m, 1H), 3.54 (ddd, 1H, J=18.4, 10.4, 2.8 Hz), 3.15 (s, 2H), 2.39 ddd, 1H, J=14.4, 8.4, 2.0 Hz), 2.30 (ddd, 1H, J=14.4, 10.0, 10.0 Hz), 1.00 (s, 3H) ppm; HRMS ($ES^+$) calculated for $C_{13}H_{21}N_9O_4$ 367.1717, found 368.1789 ($MH^+$).

mL/min BMA.25 had a retention time of 28.5 min and was isolated following lyophylization as an orange solid (0.37 mg, 19%): $^1$H NMR ($D_2O$, 400 MHz) δ 8.47 (d, 1H, J=1.6 Hz), 8.10 (dd, 1H, J=8.0, 1.6 Hz), 7.44 (d, 1H, J=8.0 Hz), 7.00 (s, 1H), 6.99 (s, 1H), 6.91 (s, 1H), 6.88 (s, 1H), 4.66 (s, 1H), 4.19 (dd, 1H, J=11.6, 9.2 Hz), 3.95 (dd, 1H, J=11.6, 5.2

BMA.13

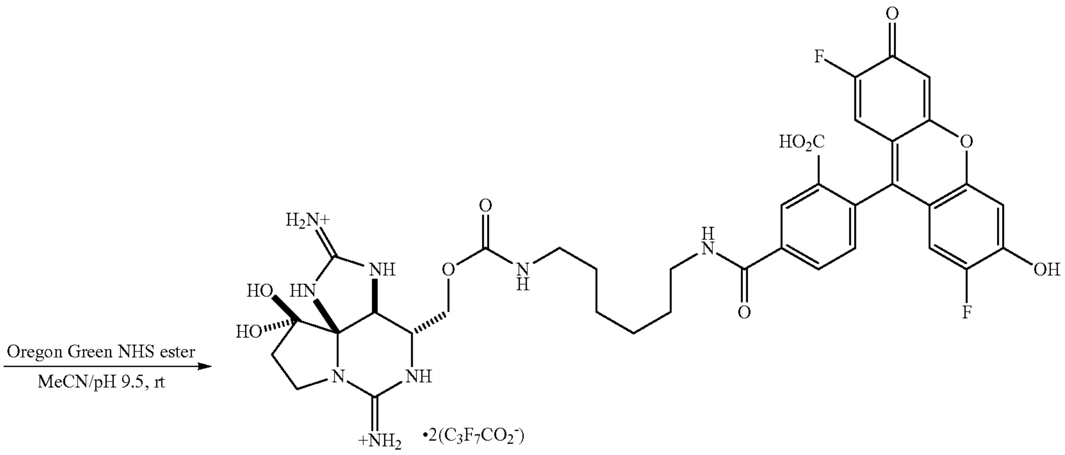

BMA.25

BMA.25:

To a stirred solution of BMA.13 (2.6 mg, 2.5 μmol) in 125 μL of pH 9.5 buffer (0.1 M aqueous $NaHCO_3/Na_2CO_3$) was added a solution of Oregon Green NHS ester (4.0 mg, 7.8 μmol, 3 equiv) in 125 μL of MeCN. The mixture was stirred at room temperature for 4 h, then acidified with 37.5 μL of Hz), 3.78-3.71 (m, 2H), 3.50 (dd, 1H, J=18.4, 10.0 Hz), 3.43 (t, 2H, J=6.8 Hz), 3.11-3.03 (m, 2H), 2.36 (ddd, 1H, J=14.0, 8.4, 1.6 Hz), 2.28 (ddd, 1H, J=14.0, 9.6, 9.6 Hz), 1.68-1.61 (m, 2H), 1.51-1.44 (m, 2H), 1.41-1.34 (m, 4H) ppm; HRMS ($ES^+$) calculated for $C_{37}H_{38}F_2N_8O_{10}$ 792.2679 found 793.2753 ($MH^+$).

BMA.13

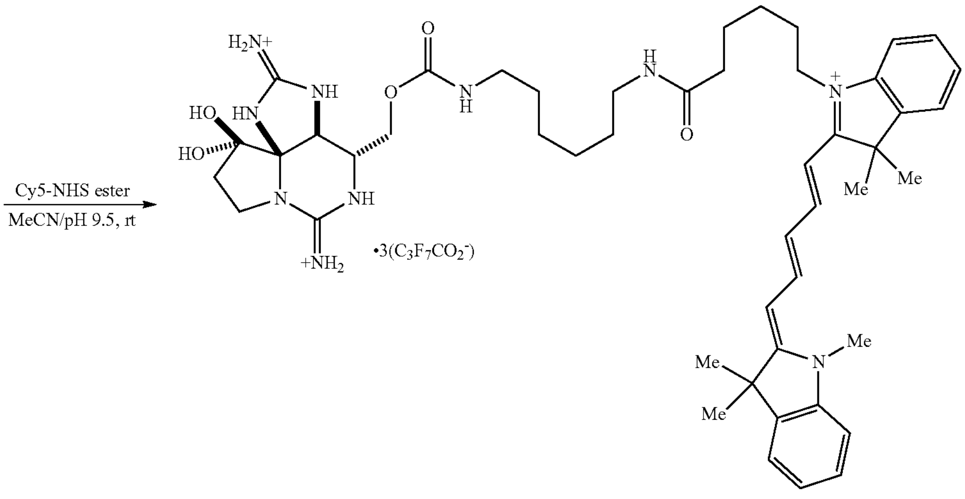

BMA.26

1.0 M aqueous HCl. After concentrating this solution under reduced pressure, the solid material was purified by reverse phase HPLC (Altima C18, 10 μm, 10×250 mm column, eluting with a gradient flow over 30 min of 10:90 MeCN/10 mM aqueous $C_3F_7CO_2H$→40:60 MeCN/10 mM aqueous $C_3F_7CO_2H$, 254 nm UV detection). At a flow rate of 6

BMA.26:

To a stirred solution of BMA.13 (7.0 mg, 6.7 μmol) in 340 μL of a 1:1 mixture of MeCN/pH 9.5 buffer (0.1 M aqueous $NaHCO_3/Na_2CO_3$) was added Cy5-NHS ester (6.2 mg, 10 μmol, 1.5 equiv). The mixture was stirred at room temperature for 4 h, then acidified with 68 μL of 1.0 M aqueous HCl.

After concentrating this solution under reduced pressure, the solid material was purified by reverse phase HPLC (Altima C18, 10 μm, 10×250 mm column, eluting with a gradient flow over 30 min of 20:80 $MeCN/H_2O$ with 0.1% $CF_3CO_2H$→50:50 $MeCN/H_2O$ with 0.1% $CF_3CO_2H$, 254 nm UV detection). At a flow rate of 6 mL/min. BMA.26 had a retention time of 26.0 min and was isolated following lyophylization as a dark blue solid (1.03 mg, 18%): $^1H$ NMR ($D_2O$, 400 MHz) δ 8.01-7.94 (m, 2H), 7.50-7.47 (m, 2H), 7.41-7.37 (m, 2H), 7.24 (t, 4H, J=7.6 Hz), 6.51 (t, 1H, J=12.8 Hz), 6.23 (d, 1H, J=2.4. hz), 6.20 (d, 1H, J=2.4 Hz), 4.64 (d, 1H, J=1.2 Hz), 4.10 (dd, 1H, J=11.6, 9.2 Hz), 4.97 (t, 2H, J=6.4 Hz), 3.81 (dd, 1H, J=11.6, 5.6 Hz), 3.75 (ddd, 1H, J=10.0, 10.0, 2.4 Hz), 3.69 (dd, 1H, J=9.2, 6.0 Hz), 3.54 (s, 3H), 3.48 (dd, 1H, J=18.0, 10.0 Hz), 3.00-2.93 (m, 4H), 2.37 (ddd, 1H, J=14.0, 8.4, 2.4 Hz), 2.29 (ddd, 1H, J=13.6, 10.4, 10.4 Hz), 2.15 (t, 2H, J=6.4 Hz), 1.85-1.78 (m, 2H), 1.62 (s, 6H), 1.62 (s, 6H), 1.61-1.54 (m, 2H), 1.37-1.24 (m, 6H), 1.20-1.16 (m, 2H) ppm; HRMS ($ES^+$) calculated for $C_{48}H_{67}N_{10}O_5^+$ 863.5290 found 430.7580 ($MH^+/2$).

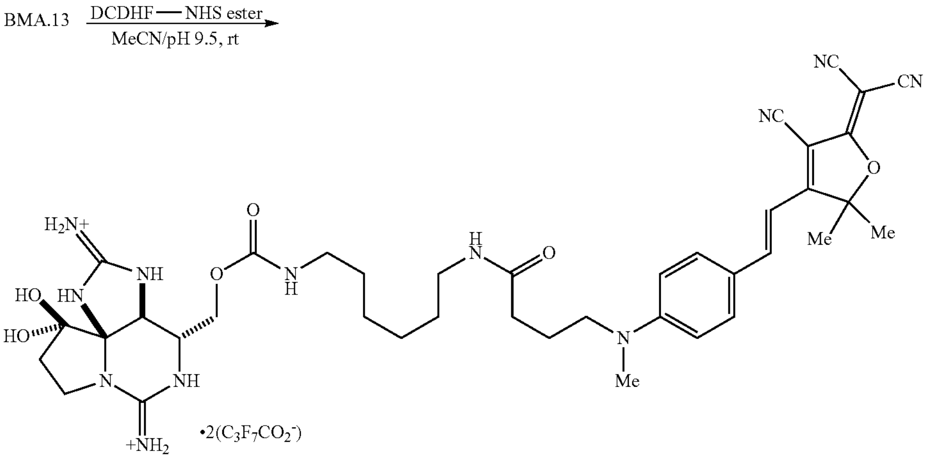

BMA.27

BMA.27:

To a stirred solution of BMA.13 in a 1:1 mixture of MeCN/pH 9.5 buffer (0.1 M aqueous $NaHCO_3/Na_2CO_3$) was added DCDHF-NHS ester. The reaction was stirred at room temperature for 3 h, then acidified with 40 μL of 1.0 M aqueous HCl. After concentrating this solution under reduced pressure, the solid material was purified by reverse phase HPLC (Altima C18, 10 μm, 10×250 mm column, eluting with a gradient flow over 30 min of 20:80 MeCN/$H_2O$ with 0.1% $CF_3CO_2H$→80:20 $MeCN/H_2O$ with 0.1% $CF_3CO_2H$, 254 nm UV detection). At a flow rate of 6 mL/min. BMA.27 had a retention time of 14.6 min and was isolated following lyophylization a dark purple solid (1.3 mg, 44%): $^1H$ NMR ($D_2O$, 500 MHz) δ 7.73 (d, 1H, J=16.5 Hz), 7.55 (d, 2H, J=8.0 Hz), 6.82 (d, 2H, J=8.5 Hz), 6.57 (d, 1H, J=15.5 Hz), 4.68 (s, 1H), 4.20 (dd, 1H, J=11.0, 11.0 Hz), 3.96 (dd, 1H, J=10.5, 4.5 Hz), 3.78-3.73 (m, 2H), 3.53-3.48 (m, 3H), 3.08 (s, 3H), 3.01-2.99 (m, 4H), 2.38 (dd, 1H, J=14.0, 5.6 Hz), 2.33-2.25 (m, 3H), 1.97-1.92 (m, 2H), 1.41-1.36 (m, 2H), 1.33-1.28 (m, 2H), 1.22-1.17 (m, 4H) ppm.

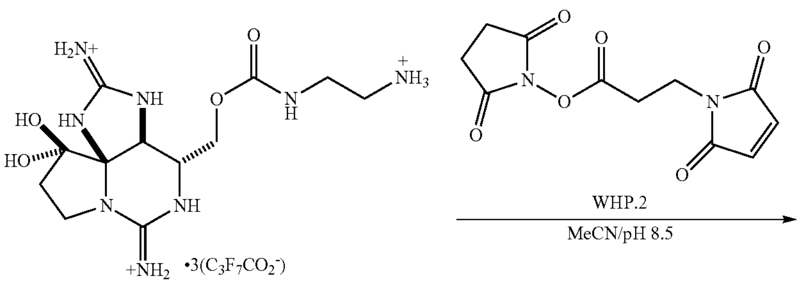

WHP.1

-continued

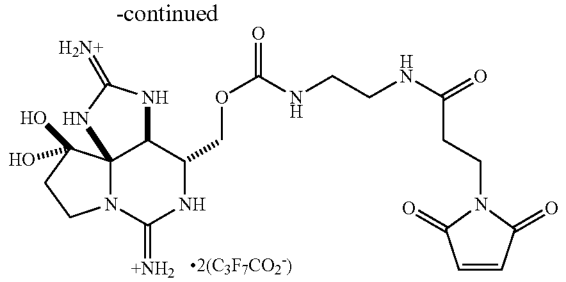

WHP.3

WHP.3:

To a solution of WHP.1 (1.5 mg, 0.0015 mmol) in 700 μL of a 2:1 mixture of MeCN and pH 8.5 buffer (0.1 M $NaH_2PO_4/Na_2HPO_4$) was added 3-maleimidopropionic acid N-hydroxysuccinimide ester (2.1 mg, 0.0077 mmol, 5.0 equiv). The solution was stirred for 4 h at room temperature, then acidified with 50 μL of 1.0 M aqueous HCl. The mixture was lyophilized to give a solid material that was purified by reverse phase HPLC (Altima C18, 10 μm, 10×250 mm column, eluting with a gradient flow over 14 min of 20:80 MeCN/10 mM aqueous $C_3F_7CO_2H$→27:73 MeCN/10 mM aqueous $C_3F_7CO_2H$, 214 nm UV detection). At a flow rate of 6 mL/min, WHP.3 had a retention time of 7.1 mom and was isolated following lyophylization as a white powder (0.38 mg, 28%). $^1H$ NMR ($D_2O$, 500 MHz) δ 6.81 (s, 2H), 4.60 (s, 1H), 4.31 (dd, 1H, J=11.3, 9.5 Hz), 3.96 (dd, 1H, J=12.0, 5.0 Hz), 3.81-3.76 (m, 2H), 3.75 (t, 2H, J=6.0 Hz), 3.58-3.54 (m, 1H), 3.31-3.20 (m, 2H), 3.14 (t, 2H, J=10.5 Hz), 2.47 (t, 2H, J=6.5 Hz), 2.41-2.29 (m, 2H) ppm; LRMS ($ES^+$) calcd for $C_{19}H_{27}N_9O_7$ 493.47 found 494.59 ($MH^+$).

Example 2

Figure 9:
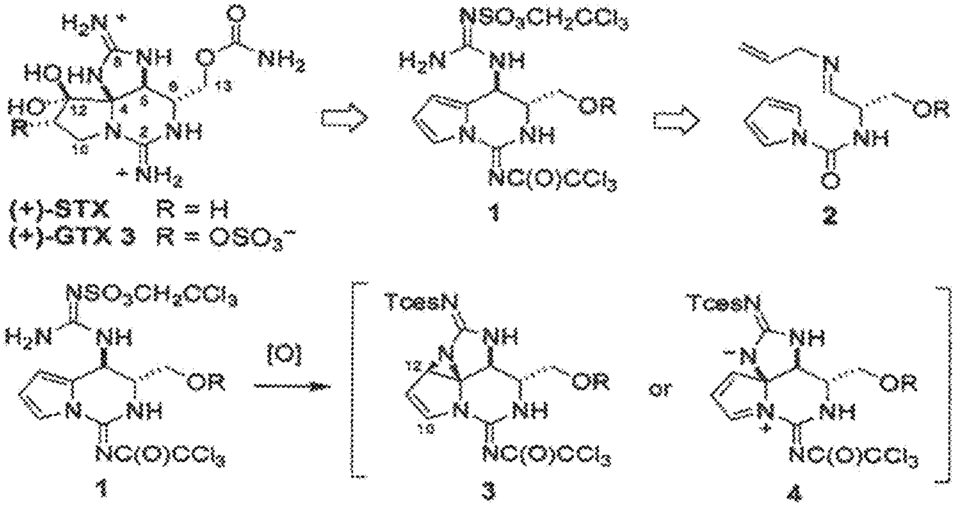
FIG. 9 illustrates an example of a synthetic approach for the synthesis of saxitoxin analogue gonyautoxin 3 (GTX 3).

This example provides a synthetic pathway for saxitoxin analogues and related molecules, as exemplified by the synthesis of gonyautoxin 3 (GTX 3), a paralytic shellfish toxin having a small molecule, bis-guanidinium structure similar to the structures of other saxitoxin analogues such as, e.g., saxitoxin, neosaxitoxin, and other gonyautoxins. Thus, the first synthetic path to any member of the more than 20 known sulfated poisons, gonyautoxin 3 (GTX 3), is described in the following (FIG. 9). (see, (a) Shimizu, Y.; Buckley, L. J.; Alam, M.; Oshima, Y.; Fallon, W. E.; Kasai, H.; Miura, I.; Gullo, V. P.; Nakanishi, K. *J. Am. Chem. Soc.* 1976, 98, 5414-5416. (b) Boyer, G. L.; Schantz, E. J.; Schnoes, H. K. *J. Chem. Soc., Chem. Comm.* 1978, 889-890. (c) Onodera, H.; Satake, M.; Oshima, Y.; Yasumoto, T.; Carmichael, W. W. *Natural Toxins* 1997, 5, 146-151. An incomplete approach to GTX 2 and 3 has been described, see: Hannick, S. M.; Kishi, Y. *J. Org. Chem.* 1983, 48, 3833-3835.)

The five-membered cyclic guanidine in GTX 3 became the focal point of our synthetic analysis following our recent disclosure of an oxidative method for 2-aminoimidazoline formation. (see, Kim, M.; Mulcahy, J. V.; Espino, C. G., Du Bois, *J. Org. Lett.* 2006, 8, 1073-1076.) This transformation is thought to proceed through the intermediacy of a Rh-bound guanidine nitrene, a reactive species capable of modifying both C—H and π-bonds. For the purpose of crafting GTX 3, amination of a pyrrole nucleus by the guanidine nitrenoid presented a novel application of this technology (FIG. 9). FIG. 9 illustrates the pyrrole oxidation and highlights the synthetic approach to GTX 3. Such a reaction could occur through either a strained aziridine 3 or dipolar species 4, attack of which by a nucleophile at either C10 or C12 would generate the desired tricyclic core. (Analogous oxidation reactions with indole derivatives give evidence for a zwitterionic intermediate, see: Padwa, A.; Flick, A. C.; Leverett, C. A.; Stengel, T. *J. Org. Chem.* 2004, 69, 6377-6386.) This regiochemical issue notwithstanding, such a strategy simplifies the GTX problem to a rather unassuming bicyclic intermediate 1. Pursuant to this approach, a route to bis-guanidine 1 was formulated that would exploit an intramolecular addition of a pyrrole to an activated imine. Although limited in precedent, this type of Pictet-Spengler reaction could be quickly evaluated, as the necessary precursor 2 is easily accessed from serine.

Figure 10:
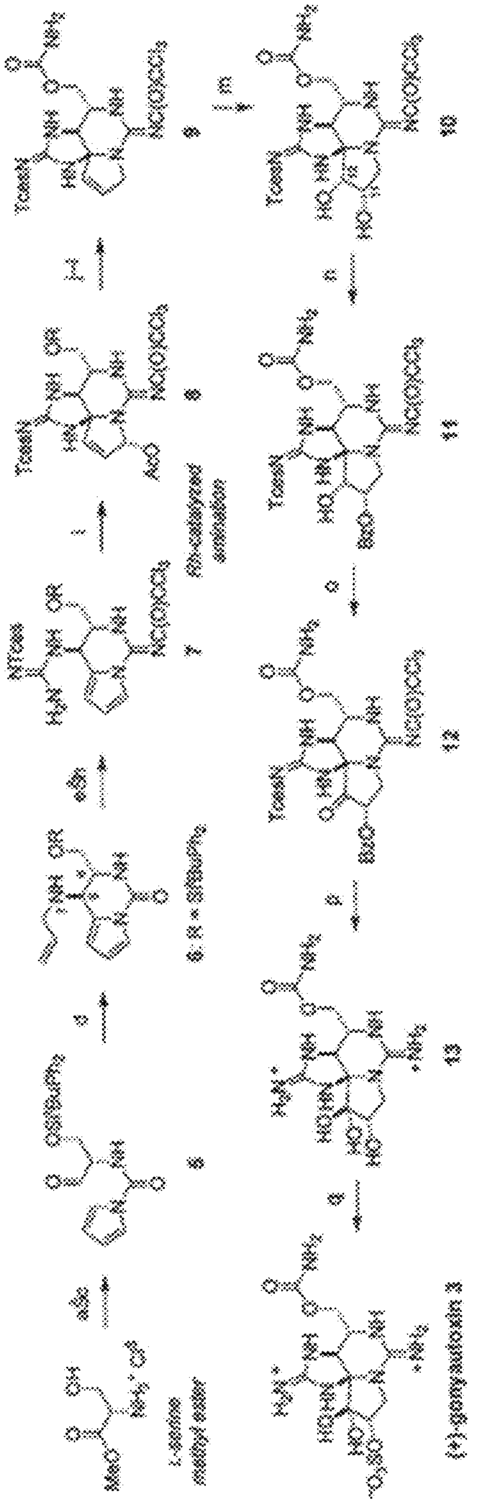
FIG. 10 provides further illustration of an example of a synthetic approach for the synthesis of saxitoxin analogue GTX 3. Conditions: (a) pyrrole-1-carboxylic acid, DCC, $Et_3N$, $CH_2Cl_2$, 65%; (b) $^tBuPh_2SiCl$, imidazole, DMF, 97%; (c) $^iBu_2AlH$, $CH_2Cl_2$, −90° C.; (d) allylamine, $BF_3OEt_2$, $CH_2Cl_2$, 56% (2 steps, >20:1 trans/cis); (e) $Pd(PPh_3)_4$, 1,3-dimethylbarbituric acid, $CH_2Cl_2$; then $Na_2CO_3$, TcesN=(SMe)Cl, 94%; (f) $EtOSO_2CF_3$, 2,4,6-tri-t-butylpyrimidine, $CH_2Cl_2$, 47° C., 78%; (g) $NH_3$, $NH_4OAc$, MeOH, 60° C., 82%; (h) $CCl_3C(O)Cl$, $^iPr_2NEt$, $CH_2Cl_2$, −20° C., 87%; (i) 5 mol % $Rh_2(esp)_2$, $PhI(OAc)_2$, MgO, $CH_2Cl_2$, 42° C., 61%; (j) $Et_3SiH$, $BF_3OEt_2$, $CH_2Cl_2$, 81%; (k) $^nBu4NF$, THF; (1) $Cl_3CC(O)NCO$, $CH_2Cl_2$, −20° C.; then MeOH, 76% (2 steps); (m) 2 mol % $OsO_4$, NMO, $THF/H_2O$, 81%; (n) PhC(O)CN, DMAP, $CH_2Cl_2$/MeCN, −78° C., 67%; (o) Dess-Martin periodinane, $CH_2Cl_2$, 79%; (p) $H_2$, Pd/C, $CF_3CO_2H$, MeOH; then $NH_3$, MeOH, 83%; (q) $DMFSO_3$, 2,6-di-t-butyl-4-methylpyridine.

The synthesis of GTX 3 commences with a three-step sequence that transforms 1-serine methyl ester to aldehyde 5 (FIG. 10). (see, Boger, D. L.; Patel, M. *J. Org. Chem.* 1987, 52, 2319-2323.) Condensation of this aldehyde with allylamine is followed by treatment with $BF_3.OEt_2$, which effects the desired ring closure to furnish the trans-substituted urea 6 with >20:1 diastereoselectivity. (An X-ray crystal structure of a modified form of this intermediate confirms the trans stereochemical assignment.) Assuming the C5/C6 stereochemistry (GTX numbering) in this product is established under kinetic control, a conformation that minimizes allylic strain between the substituents on C6 and N7 could account for the observed diastereoselectivity. Forwarding 6 to the requisite amination precursor 7 was efficiently achieved through a sequence of four transformations; of note is the development of a single step process for sequential allyl deprotection and isothiourea formation (cf., step e, 6→7, Tces=$SO_3CH_2CCl_3$).

Successful application of the Rh-catalyzed amination reaction with guanidine 7 assembles the tricyclic frame of GTX 3 in a singular, defining event. The reaction is chemoselective, as C—H insertion into the proximal C6 center does not appear to compete with pyrrole modification. Acetic acid, produced as a byproduct in this transformation, adds regio- and stereoselectively to the putative aziridine, affording N,O-acetal 8 as the only product based on $^1H$ NMR analysis of the reaction mixture. (The instability of this material on $SiO_2$ is likely responsible for the reduced isolated yields. The choice of solvent has a rather substantial influence on the performance of this step, $CH_2Cl_2$ being the only medium in which complete consumption of the starting guanidine 7 is observed.) In spite of the fact that acetate attack occurs exclusively at C10 instead of C12, the isolated tricycle 8 is suitably disposed for completion of the GTX 3 synthesis.

The stability of 8 towards handling and purification proved somewhat capricious, thus prompting a decision to reduce the presumably labile N,O-acetal unit. This transformation is smoothly performed with $Et_3SiH$ and $BF_3.OEt_2$, giving the C11-C12 alkene in 81% yield. None of the transposed olefin product is detected under these conditions. Installation of the primary carbamate is then made possible using $Cl_3CC(O)NCO$. (see, e.g. Kocovsky, P. *Tetrahedron Lett.* 1986, 27, 5521-5524.) Intermediate 9 contains all of the necessary carbon centers found in the natural product.

Alternative approaches for transforming alkene 9 to the corresponding α-ketol have been examined Regioselective ketohydroxylation would provide the most expeditious route to the desired target; such conditions have not yet been identified. (for ketohydroxylation precedent, see Fleming, J. J.; McReynolds, M. D.; Du Bois, J. *J. Am. Chem. Soc.* 2007, 129, 9964-9975.) By contrast, olefin dihydroxylation using 2 mol % $OsO_4$ and N-methylmorpholine-N-oxide is quite effective and affords diol 10 as a single stereoisomer. Analysis of molecular models indicates that the β-face of the alkene in 9 is more exposed, consistent with the observed selectivity. Protection of C11-OH is accomplished under highly optimized conditions that employ benzoyl cyanide and DMAP. Other, more standard acylating agents (e.g., PhC(O)Cl) in combination with 3° amine or pyridine bases produce inseparable mixtures of isomeric, benzoylated materials. While it is possible to install other blocking groups such as $^tBuMe_2Si$— at C11, their larger steric volume prevents subsequent oxidation of the C12 alcohol. With 11, ketone formation at C12 is enabled using Dess-Martin periodinane. (Hexavalent chromium, TEMPO and DMSO-based oxidation protocols universally consumed starting material without generating ketone 12.)

Removal of all three protecting groups in 12 through a single operation affords 11β-hydroxysaxitoxin, which is isolated as the bis-$C_3F_7CO_2$ salt. Analytical data for this material ($^1H$ NMR, HRMS) matches that found in the literature. (see, (a) Wichmann, C. F.; Boyer, G. L.; Divan, C. L.; Schantz, E. J.; Schnoes, H. K. *Tetrahedron Lett.* 1981, 22, 1941-1944. (b) Shimizu, Y.; Kobayashi, M.; Genenah, A.; Oshima, Y. *Tetrahedron* 1984, 40, 539-544.)

Figure 11:
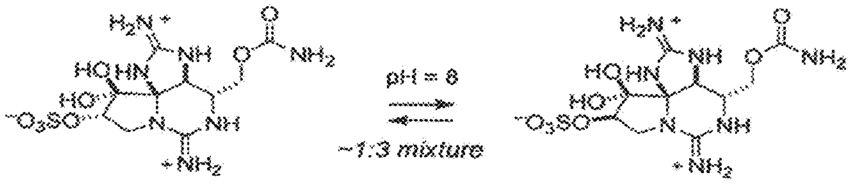
FIG. 11 illustrates the structures and relationships between saxitoxin analogues GTX 3 and gonyautoxin 2 (GTX 2).

To complete the synthesis of GTX 3, selective sulfation of the C11 alcohol is achieved using $DMF.SO_3$ in combination with 2,6-di-t-butyl-4-methylpyridine as an acid scavenger. The pure toxin is obtained as the $C_3F_7CO_2^-$ adduct following reverse-phase HPLC. This material matches the reported physical properties of natural GTX 3 in all respects, and blocks electrical transmission in heterologously expressed $Na_V1.4$ ion channels with an $IC_{50}$ value of ~20 nM (reported $IC_{50}$=13.2-33.5 nM). (see, (a) Choudhary, G.; Shang, L.; Li, X.; Dudley, Jr., S. C. *Biophys. J.* 2002, 83, 912-919. (b) Kao, C. Y.; Kao, P. N.; James-Kracke, M. R.; Koehn, F. E.; Wichmann, C. F.; Schnoes, H. K. *Toxicon* 1985, 23, 647-655.) Upon standing GTX 3 in aqueous solution at pH=8, epimerization at C11 occurs to give GTX 2, also in agreement with published observations (FIG. 11). (see, e.g., (a) Shimizu, Y.; Buckley, L. J.; Alam, M.; Oshima, Y.; Fallon, W. E.; Kasai, H.; Miura, I.; Gullo, V. P.; Nakanishi, K. *J. Am. Chem. Soc.* 1976, 98, 5414-5416. (b) Wichmann, C. F.; Boyer, G. L.; Divan, C. L.; Schantz, E. J.; Schnoes, H. K. *Tetrahedron Lett.* 1981, 22, 1941-1944.) FIG. 11 illustrates the epimerization at C11 that occurs upon standing.

The completed synthesis of GTX 3 offers a unique strategic approach for preparing this family of saxitoxin analogues and related structures, while underscoring the power of Rh-catalyzed amination for heterocycle assembly. (An attempt to utilize guanidine C—H insertion for assembling bromopyrrole-derived natural products has been described, see: Wang, S.; Romo, D. *Angew. Chem. Int. Ed.* 2008, 47, 1284-1286. For a recent review of this family of molecules, see: Köck, M.; Grube, A.; Seiple, I. B.; Baran, P. S. *Angew. Chem. Int. Ed.* 2007, 46, 6586-6594.)

Materials and Methods.

All reagents were obtained commercially unless otherwise noted. Reactions were performed using oven dried glassware under an atmosphere of dry nitrogen. Air- and moisture sensitive liquids and solutions were transferred via syringe or stainless steel cannula. Organic solutions were concentrated under reduced pressure (~20 Torr) by rotary evaporation. Dichloromethane ($CH_2Cl_2$), tetrahydrofuran (THF), acetonitrile (MeCN), N,N-dimethylformamide (DMF), toluene (PhMe), and benzene were passed through columns of activated alumina immediately prior to use. Chromatographic purification of products was accomplished using forced flow chromatography on Silicycle silica gel 60 (40-63 μM). Thin layer chromatography was performed on EM Science silica gel 60 $F_{254}$ plates (250 mm) Visualization of the developed chromatogram was accomplished by fluorescence quenching and by staining with ethanolic anisaldehyde, aqueous potassium permanganate, or aqueous ceric ammonium molybdate (CAM) solution. High Pressure Liquid Chromatography (HPLC) purification was performed using a Varian instrument with an Alltima C18, 10×250 mm, 10 μm column using $MeCN/H_2O$ as eluent with 0.1% $CF_3CO_2H$ buffer or 10 mM $C_3F_7COOH$ (as indicated).

Nuclear magnetic resonance (NMR) spectra were acquired on a Varian Inova spectrometer operating at 400, 500 or 600 and 100, 125 or 150 MHz for $^1H$ and $^{13}C$, respectively, and are referenced internally according to residual solvent signals. Data for $^1H$ NMR are recorded as follows: chemical shift (δ, ppm), multiplicity (s, singlet; d, doublet, t, triplet; q, quartet; quint, quintet; sept, septet; m, multiplet; br, broad), integration, coupling constant (Hz). Data for $^{13}C$ are reported in terms of chemical shift (δ, ppm). Infrared spectra were recorded as thin films using NaCl salt plates on a Thermo-Nicolet 300 FT-IR spectrometer and are reported in frequency of absorption. Optical rotation data were obtained from samples loaded into a 50 mm cell on a Jasco DIP-1000 digital polarimeter operating at the Na D-line. High-resolution mass spectra were obtained from the Vincent Coates Foundation Mass Spectrometry Laboratory at Stanford University.

Experimental Protocols and Characterization Data:

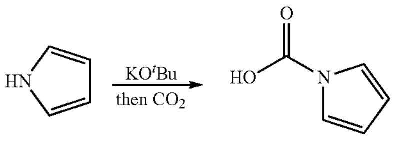 [SMILES: c1cc[nH]c1 ; O=C(O)n1cccc1 ; "KOtBu"]

To an ice-cold solution of KO$^t$Bu (46.0 g, 409.9 mmol, 1.1 equiv) in 1.2 L of 1:1 $Et_2O$/THF was slowly added pyrrole (26.0 mL, 372.0 mmol). The reaction mixture was warmed to room temperature and stirred for 30 min. Following this time, excess solid $CO_2$ (~200 g) was slowly added through the top of the flask causing vigorous bubbling and a drop in the reaction temperature. The reaction vessel was placed in a room temperature water bath and allowed to stand until no solid $CO_2$ remained at the bottom of the flask. 300 mL of $H_2O$ was added and the contents were transferred to a separatory funnel. The aqueous layer was collected and the organic phase was washed with 300 mL of $H_2O$. The combined aqueous extracts were acidified to pH<1 with 1.0 M aqueous HCl. To this aqueous solution was then added 400 mL of $Et_2O$ and the contents were transferred again to a separatory funnel. The organic phase was collected and the aqueous phase was extracted with 2×400 mL of $Et_2O$. The combined organic extracts were dried over $Na_2SO_4$, filtered, and concentrated under reduced pressure to afford pyrrole-1-carboxylic acid as a white solid (35.6 g, 86%). mp 114-116° C.; $^1H$ NMR ($CDCl_3$, 400 MHz) 8.54 (br s, 1H), 7.31 (t, 2H, J=2.4 Hz), 6.31 (t, 2H, J=2.4 Hz) ppm., which matched data reported in the literature. (see, Boger, D. L.; Patel, M. "Activation and coupling of pyrrole-1-carboxylic acid in the formation of pyrrole N-carbonyl compounds—pyrrole-1-carboxylic acid anhydride." *Journal of Organic Chemistry* 1987, 52, 2319-2323.)

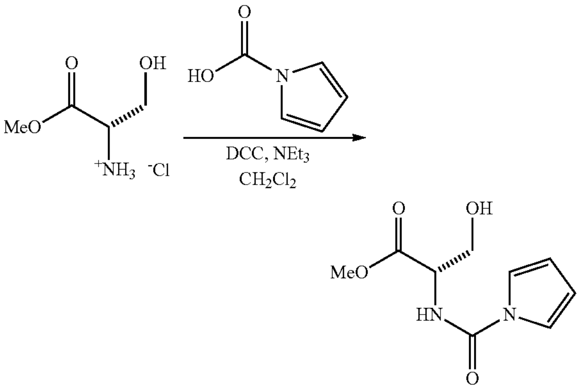

JVM.1

To a solution of pyrrole carboxylic acid (35.6 g, 323.3 mmol, 2.0 equiv) in 1.25 L of $CH_2Cl_2$ was added solid dicyclohexylcarbodiimide (68.3 g, 331.1 mmol, 2.05 equiv) in a single portion. After stirring the mixture vigorously for 20 min, a suspension of finely ground L-serine methyl ester hydrochloride salt (25.2 g, 161.7 mmol) and triethylamine (36.7 mL, 242.2 mmol, 1.5 equiv) in 550 mL of $CH_2Cl_2$ was added in one portion. The mixture was stirred for an additional 22 h then filtered through a pad of Celite. The flask and filter cake were rinsed with cold $CH_2Cl_2$ and the combined filtrates were concentrated under reduced pressure. Purification of the isolated material by chromatography on silica gel (gradient elution: 7:1→1:1 hexanes/EtOAc) afforded urea JVM.1 as a pale yellow oil (22.9 g, 67%). TLC $R_f$=0.24 (1:1 hexanes/EtOAc); $^1H$ NMR ($CDCl_3$, 400 MHz) δ 7.30-7.26 (m, 2H), 7.11-7.05 (m, 1H), 7.24-7.21 (m, 2H), 4.67-4.64 (m, 1H), 4.03 (dd, 1H, J=11.2, 4.0 Hz), 3.92 (dd, 1H, J=11.6, 3.6 Hz), 3.73 (s, 3H) ppm; $^{13}C$ NMR ($CDCl_3$, 100 MHz) δ 171.4, 151.5, 119.0, 112.4, 62.7, 56.1, 53.1 ppm; IR (thin film) ν 3371, 2953, 1741, 1685, 1548, 1529, 1475, 1357, 1306, 1216, 1076, 740 $cm^{-1}$.

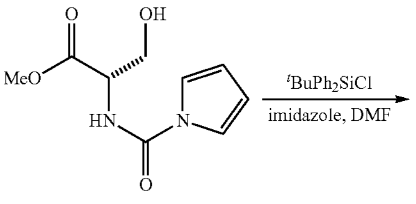

JVM.1

-continued

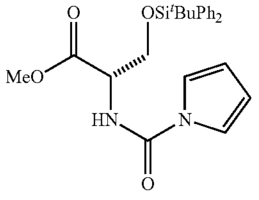

JVM.2

To a solution of alcohol JVM.1 (16.3 g, 76.8 mmol) in 110 mL of DMF were added sequentially imidazole (6.80 g, 99.9 mmol, 1.3 equiv) and t-$BuPh_2SiCl$ (20.6 ml, 80.7 mmol, 1.05 equiv). The reaction mixture was stirred for 14 h, diluted with 300 mL of $Et_2O$ and then quenched with 250 mL of $H_2O$. The contents were transferred to a separatory funnel, and the organic phase was collected and washed with 2×250 mL of $H_2O$ and 1×250 mL of saturated aqueous NaCl. The ethereal extract was dried over $MgSO_4$ and concentrated under reduced pressure. Purification of the oily residue by chromatography on silica gel (gradient elution: 1:0→4:1 hexanes/EtOAc) afforded the silyl ether JVM.2 as a pale yellow oil (32.1 g, 93%). TLC $R_f$=0.51 (3:1 hexanes/EtOAc); $^1H$ NMR ($CDCl_3$, 400 MHz) δ 7.60-7.57 (m, 4H), 7.46-7.30 (m, 6H), 7.16 (dd, 2H, J=2.4, 2.4 Hz), 6.41 (d, 1H, J=8.0 Hz), 6.29 (dd, 2H, J=2.4, 2.4 Hz), 4.70 (ddd, 1H, J=8.0, 2.4, 2.4 Hz), 4.20 (dd, 1H, J=10.4, 2.4 Hz), 4.01 (dd, 1H, J=10.4, 3.2 Hz), 3.79 (s, 3H), 1.05 (s, 9H) ppm; $^{13}C$ NMR ($CDCl_3$, 100 MHz) δ 170.5, 150.2, 135.4, 135.3, 132.6, 132.4, 130.00, 129.98, 127.85, 127.82, 118.4, 112.1, 64.2, 55.4, 52.7, 26.7, 19.2 ppm; IR (thin film) ν 3361, 2954, 2858, 1748, 1711, 1508, 1473, 1357, 1113, 736, 703 $cm^{-1}$; HRMS ($ES^+$) calcd for $C_{25}H_{30}N_2O_4Si$ 450.1975 found 473.1869 ($MNa^+$).

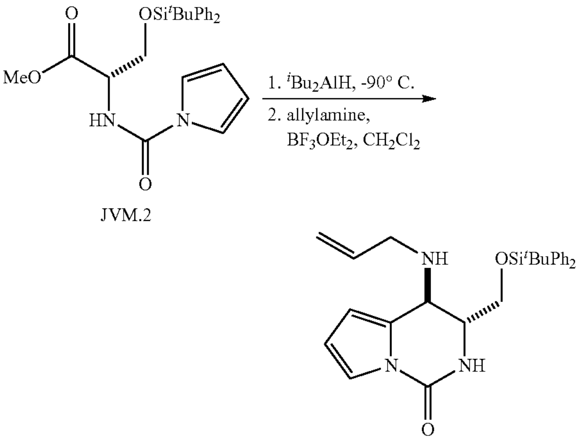

JVM.2

JVM.3

To a solution of methyl ester JVM.2 (10.3 g, 22.9 mmol) in 230 mL of $CH_2Cl_2$ cooled to −91° C. was added $^iBu_2AlH$ (22.9 mL of a 1.50 M solution in PhMe, 34.3 mmol, 1.5 equiv) dropwise over 15 min. The mixture was stirred at −91° C. for 4 h and then a second portion of $^iBu_2AlH$ (7.6 mL of a 1.50 M solution in PhMe, 11.4 mmol, 0.5 equiv) was added. The reaction was stirred for an additional 1.5 h and then quenched at this temperature by the slow addition of 30 mL of EtOAc. The contents were poured into an Erlenmeyer flask containing 220 mL of 1.0 M aqueous sodium potassium tartrate and 440 mL of EtOAc, and stirred vigorously for 3.5 h. Following this time, the contents were transferred to a separatory funnel. The organic phase was collected, dried over $MgSO_4$ and concentrated under reduced pressure to a pale yellow oil. This material was used immediately without purification to minimize loss of optical purity. A sample of the pure aldehyde was obtained by chromatography on silica gel (9:1→3:1 hexanes/EtOAc). TLC $R_f$=0.51 (3:1 hexanes/EtOAc); $^1$H NMR ($CDCl_3$, 400 MHz) δ 9.72 (s, 1H), 7.63-7.57 (m, 4H), 7.52-7.36 (m, 6H), 7.21 (dd, 2H, J=2.4, 2.4 Hz), 6.49 (br d, 1H, J=6.4 Hz), 6.35 (dd, 2H, J=2.4, 2.4 Hz), 4.72-4.68 (m, 1H), 4.40 (dd, 1H, J=11.2, 2.8 Hz), 4.12 (dd, 1H, J=10.8, 3.6 Hz), 1.12 (s, 9H) ppm.

To a solution of the unpurified aldehyde (22.9 mmol, based on the assumption of 100% yield) in 220 mL of $CH_2Cl_2$ cooled to 0° C. was added allyl amine (1.71 mL, 22.9 mmol). The mixture was warmed to room temperature over 20 min and then cooled to −78° C. $BF_3$.$OEt_2$ (10.2 mL, 80.0 mmol, 3.5 equiv) was added dropwise over 10 min to this solution. Following this process, the contents were warmed to 23° C. The reaction was stirred for 1 h and then quenched by the addition of 220 mL of saturated aqueous $NaHCO_3$. The contents were stirred vigorously for 20 min, diluted with 440 mL of EtOAc and then transferred to a separatory funnel. The organic phase was collected and the aqueous phase was extracted with 2×140 mL of EtOAc. The combined organic extracts were dried over $MgSO_4$ and concentrated under reduced pressure. Purification of the oily residue by chromatography on silica gel (gradient elution: 4:1→1:1 hexanes/EtOAc) afforded amine JVM.3 as a pale yellow foam (5.9 g, 56% over 2 steps). TLC $R_f$=0.21 (1:1 hexanes/EtOAc); $[\alpha]_{Na}$−93.7° (c=4.11, $CDCl_3$); $^1$H NMR ($CDCl_3$, 400 MHz) δ 7.61-7.55 (m, 4H), 7.43-7.31 (m, 6H), 7.28 (dd, 1H, J=3.2, 1.6 Hz), 6.17 (dd, 1H, J=3.2, 3.2 Hz), 6.11-6.09 (m, 1H), 5.88-5.78 (m, 2H), 5.18 (dd, 1H, J=17.2, 1.6 Hz), 5.10 (dd, 1H, J=10.4, 1.6 Hz), 3.96 (d, 1H, J=3.2), 3.73 (ddd, 1H, J=10.4, 6.8, 3.6 Hz), 3.60-3.52 (m, 2H), 3.30-3.17 (m, 2H), 1.02 (s, 9H) ppm; $^{13}$C NMR ($CDCl_3$, 100 MHz) δ 149.6, 136.2, 135.41, 135.38, 132.7, 132.6, 129.80, 129.77, 128.8, 127.73, 127.69, 117.9, 116.5, 110.6, 110.4, 64.2, 58.2, 49.13, 49.07, 26.6, 19.0 ppm; IR (thin film) ν 3247, 2931, 2858, 1716, 1428, 1113, 733, 703 $cm^{-1}$; HRMS ($ES^+$) calcd for $C_{27}H_{33}N_3O_2Si$ 459.2342 found 482.2235 ($MNa^+$).

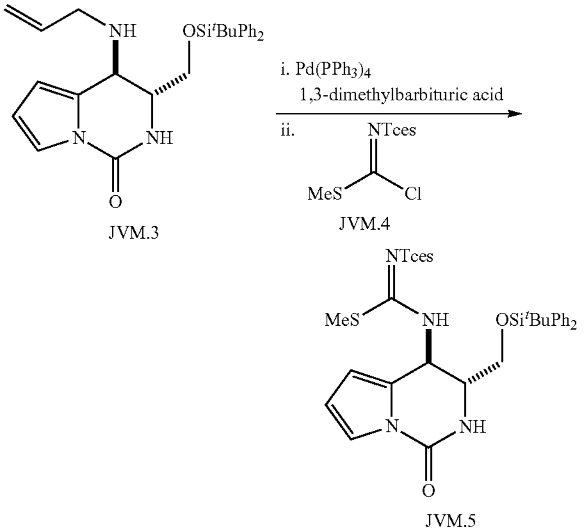

JVM.3

JVM.4

JVM.5

Amine JVM.3 (5.50 g, 12.0 mmol), 1,3-dimethylbarbituric acid (5.61 g, 35.9 mmol, 3.0 equiv) and $Pd(PPh_3)_4$ (277 mg, 0.24 mmol, 0.02 equiv) were combined and the flask swept with $N_2$ for several minutes. To the reaction vessel was added 120 mL of deoxygenated $CH_2Cl_2$ (3× freeze/pump/thaw cycle). The reaction mixture was stirred for 8 h, following which time 125 mL of a 1.0 M aqueous solution of $Na_2CO_3$ and imidate JVM.4 (3.84 g, 12.0 mmol) were added sequentially. The biphasic mixture was stirred for 20 min, then diluted with 240 mL of EtOAc and transferred to a separatory funnel. The organic phase was collected and the aqueous layer was extracted with 1×120 mL of EtOAc. The combined organic extracts were dried over $MgSO_4$ and concentrated under reduced pressure. Purification of the oily residue by chromatography on silica gel (gradient elution: 9:1→2:1 hexanes/EtOAc) afforded isothiourea JVM.5 as a yellow foam (8.1 g, 96%). TLC $R_f$=0.45 (3:2 hexanes/EtOAc); $[\alpha]_{Na}$−83.2° (c=1.0, MeOH); $^1$H NMR ($C_6D_6$, 400 MHz) δ 8.35 (br d, 1H, J=8.0 Hz), 7.64-7.56 (m, 4H), 7.41 (dd, 1H, J=3.2, 1.6 Hz), 7.26-7.20 (m, 6H), 6.14 (br s, 1H), 5.95 (dd, 1H, J=3.2, 3.2 Hz), 5.31 (br s, 1H), 5.02 (br s, 1H), 4.50 (br s, 2H), 3.33-3.24 (m, 2H), 2.83 (br s, 1H), 1.82 (br s, 3H), 1.09 (s, 9H) ppm; $^{13}$C NMR ($CDCl_3$, 100 MHz) δ 170.5, 148.9, 135.50, 135.47, 132.3, 132.1, 130.3, 130.1, 128.0(2), 124.5, 119.3, 112.4, 111.6, 93.6, 78.6, 63.1, 57.7, 47.5, 26.8, 19.2, 14.7 ppm; IR (thin film) ν 3287, 2931, 2858, 1717, 1428, 1349, 1164, 1113, 738, 703 $cm^{-1}$; HRMS ($ES^+$) calcd for $C_{28}H_{33}Cl_3N_4O_5S_2Si$ 702.0727 found 725.0629 ($MNa^+$).

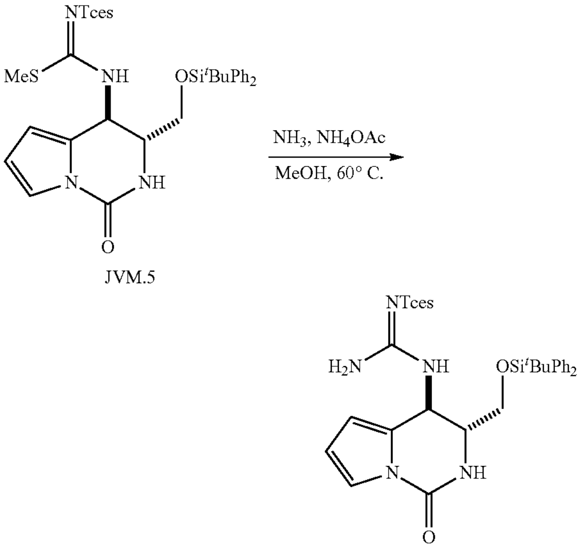

JVM.5

JVM.6

A 100 mL thick-walled tube containing a magnetic stir bar was charged with isothiourea JVM.5 (1.95 g, 2.76 mmol), $NH_4OAc$ (1.1 g, 13.8 mmol, 5.0 equiv), and $NH_3$ (27 mL of a 2.0 M solution in MeOH, 54.0 mmol, 19.6 equiv). The vessel was sealed with a Teflon screw-cap and the contents heated at 60° C. for 24 h. The reaction mixture was cooled to room temperature and concentrated under reduced pressure. Purification by chromatography on silica gel (gradient elution: hexanes 1:1 hexanes/EtOAc) afforded guanidine JVM.6 as a white solid (1.64 g, 88%). TLC $R_f$=0.37 (1:1 hexanes/EtOAc); $^1$H NMR ($CD_3OD$, 400 MHz) δ 7.62-7.56 (m, 4H), 7.42-7.32 (m, 6H), 7.26-7.24 (m, 1H), 6.28-6.26

(m, 1H), 6.21 (dd, 1H, J=3.2, 3.2 Hz), 5.46 (br s, 1H), 4.62 (s, 2H), 3.80-3.76 (m, 1H), 3.66 (dd, 1H, J=10.4, 4.8 Hz), 3.45 (dd, 1H, J=10.0, 7.6 Hz), 0.99 (s, 9H) ppm; $^{13}C$ NMR ($CD_3OD$, 100 MHz) δ 156.5, 150.2, 135.6, 135.5, 132.7, 132.5, 129.90, 129.87, 127.83, 127.81, 127.2, 117.9, 111.19, 111.14, 94.5, 78.2, 64.3, 57.4, 43.6, 26.2, 18.9 ppm; IR (thin film) ν 3355, 2932, 2859, 2455, 1695, 1544, 1445, 1298, 1114, 1019, 848, 739 $cm^{-1}$.

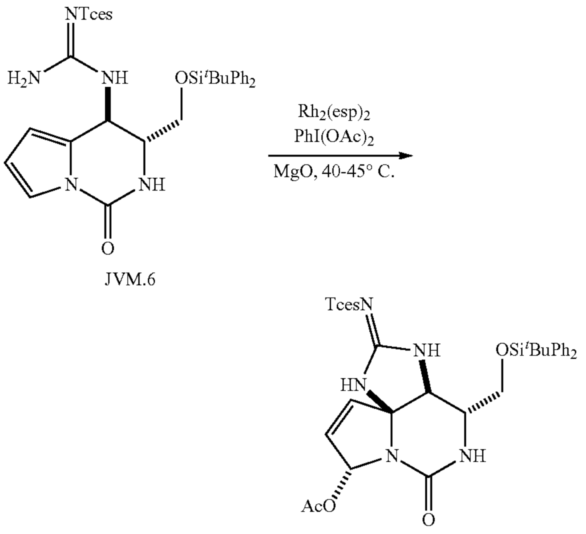

JVM.6

JVM.7

A 100 mL round-bottom flask was charged with Tces guanidine JVM.6 (422 mg, 0.63 mmol), $Rh_2(esp)_2$ (33 mg, 44 μmol, 0.07 equiv), $PhI(OAc)_2$ (404 mg, 1.25 mmol, 2.0 equiv), and MgO (114 mg, 2.8 mmol, 4.4 equiv). To the combined solids was added 25 mL of toluene. The resulting deep green reaction mixture was heated between 40-45° C. for 3 h. Following this time, the mixture was cooled to room temperature and applied directly to a column of silica gel. Gradient elution (hexanes→1:1 hexanes/EtOAc) afforded guanidine JVM.7 as a white solid (200 mg, 43%). TLC $R_f$=0.41 (1:1→hexanes/EtOAc); $^1H$ NMR ($CD_3OD$, 400 MHz) δ 7.63-7.60 (m, 4H). 7.47-7.37 (m, 6H), 6.44 (d, 1H, J=2.0 Hz), 6.25 (d, 1H, J=5.6 Hz), 6.07 (dd, 1H, J=5.6, 2.0 Hz), 4.63 (s, 1H), 4.62 (s, 1H), 4.46 (d, 1H, J=1.4 Hz), 3.65-3.60 (m, 1H), 3.48 (dd, 1H, J=3.0, 6.0 Hz), 2.05 (s, 3H), 1.05 (s, 9H) ppm; $^{13}C$ NMR ($CDCl_3$, 125 MHz) δ 170.5, 157.9, 154.3, 135.79, 135.77, 133.4, 132.3, 132.2, 130.6, 130.5, 130.4, 128.36, 128.33, 94.1, 85.8, 83.6, 78.4, 63.9, 56.4, 55.7, 27.1, 21.5, 19.4 ppm; IR (thin film) ν 3345, 2932, 2859, 1685, 1612, 1428, 1114, 734, 703 $cm^{-1}$.

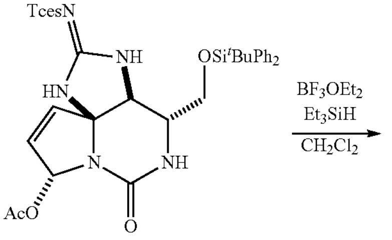

JVM.7

-continued

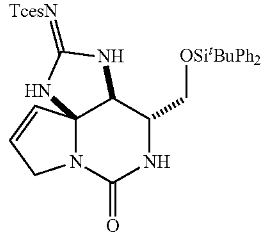
JVM.8

To a solution of allylic acetate JVM.7 (171 mg, 0.23 mmol) and triethylsilane (188 μL, 1.17 mmol, 5.0 equiv) in 5.0 mL of $CH_2Cl_2$ cooled to −78° C. was added $BF_3.OEt_2$ (68 μL, 0.54 mmol, 2.3 equiv). The reaction contents were allowed to slowly warm to room temperature and were stirred for 3 h. Following this time, the reaction was quenched by the addition of 5 mL of saturated aqueous $NaHCO_3$ and the mixture stirred vigorously for 15 min. The contents were diluted with 10 mL of EtOAc and transferred to a separatory funnel. The organic layer was collected and the aqueous phase was extracted with 2×10 mL of EtOAc. The combined organic extracts were dried over $MgSO_4$ and concentrated under reduced pressure. Purification of the isolated material by chromatography on silica gel (gradient elution: hexanes→2:1 hexanes/EtOAc) afforded olefin JVM.8 as a white solid (121 mg, 77%). TLC $R_f$=0.22 (1:1 hexanes/EtOAc); $^1H$ NMR ($CD_3OD$, 400 MHz) δ 7.64-7.60 (m, 4H), 7.46-7.38 (m, 6H), 6.15-6.12 (m, 1H), 5.92-5.89 (m, 1H), 4.60 (s, 2H), 4.43 (d, 1H, J=1.2 Hz), 4.13 (ddd, 17.0, 2.2, 2.2 Hz), 3.81 (ddd, 1H, J=17.0, 2.2, 2.2 Hz), 3.59-3.51 (m, 1H), 3.45 (dd, 1H, J=7.2, 9.6 Hz), 1.04 (s, 9H) ppm; $^{13}C$ NMR ($CDCl_3$, 125 MHz) δ 157.8, 156.2, 135.82, 135.77, 132.5, 132.4, 131.3, 130.5, 130.4, 128.3, 128.2, 94.1, 84.3, 78.4, 64.0, 57.8, 57.3, 52.2, (30.0), 27.1, 19.4 ppm; IR (thin film) ν 3231, 2930, 1673, 1631, 1526, 1183, 1114, 732, 702 $cm^{-1}$.

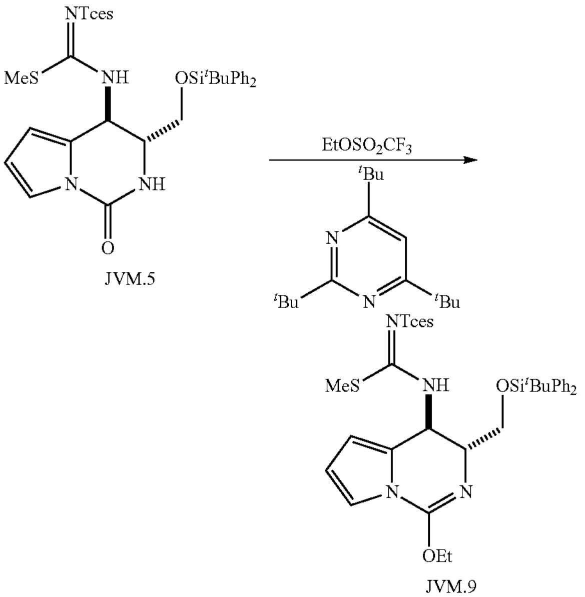

JVM.5

JVM.9

To a solution of isothiourea JVM.5 (6.62 g, 9.4 mmol) and 2,4,6-tri-tert-butylpyrimidine (8.64 g, 34.8 mmol, 3.7 equiv)

in 19.0 mL of $CH_2Cl_2$ was added ethyl trifluoromethanesulfonate (7.3 mL, 56.3 mmol, 6.0 equiv). The reaction vessel was sealed with a glass stopper, the solution warmed to 37° C. and stirred for 14 h. Following this time, the reaction was cooled to room temperature, diluted by the addition of 50 mL of $CH_2Cl_2$ and transferred to an Erlenmeyer flask containing 570 mL of saturated aqueous $NaHCO_3$. The biphasic mixture was vigorously stirred for 12 h, diluted with 150 mL of EtOAc and transferred to a separatory funnel. The organic layer was collected and the aqueous phase was extracted with 2×150 mL of EtOAc. The combined organic extracts were dried over $MgSO_4$ and concentrated under reduced pressure. Purification of the oily residue by chromatography on silica gel (gradient elution: 1:0→3:1 hexanes/EtOAc) afforded isourea JVM.9 as a yellow foam (5.30 g, 77%). TLC $R_f$=0.34 (3:1 hexanes/EtOAc); $^1H$ NMR ($CDCl_3$, 400 MHz) δ 8.08 (d, 1H, J=8.8 Hz), 7.65-7.58 (m, 4H), 7.43-7.30 (m, 6H), 7.03 (dd, 1H, J=3.2, 1.6 Hz), 6.35 (dd, 1H, J=3.2, 0.8 Hz), 6.19 (dd, 1H, J=3.2, 3.2 Hz), 5.38 (dd, 1H, J=8.6, 3.4 Hz), 4.62 (s, 2H), 4.36-4.19 (m, 2H), 4.02 (ddd, 1H, J=7.6, 3.8, 3.8 Hz), 3.75 (dd, 1H, J=10.2, 4.0 Hz), 3.25 (dd, 1H, J=10.2, 8.2 Hz), 2.50 (s, 3H), 1.35 (t, 3H, J=7.0 Hz), 1.04 (s, 9H) ppm; $^{13}C$ NMR ($CDCl_3$, 100 MHz) δ 170.6, 146.7, 135.5, 135.4, 132.8, 132.7, 129.8, 129.7, 127.7, 127.6, 125.2, 117.0, 111.0, 110.4, 93.6, 78.4, 63.4, 62.8, 60.8, 47.7, 26.6, 19.1, 14.5, 14.0 ppm; IR (thin film) ν 3289, 2932, 2858, 1669, 1561, 1428, 1333, 1160, 1113, 732 $cm^{-1}$; HRMS ($ES^+$) calcd for $C_{30}H_{37}Cl_3N_4O_5S_2Si$ 730.1040 found 753.0940 ($MNa^+$).

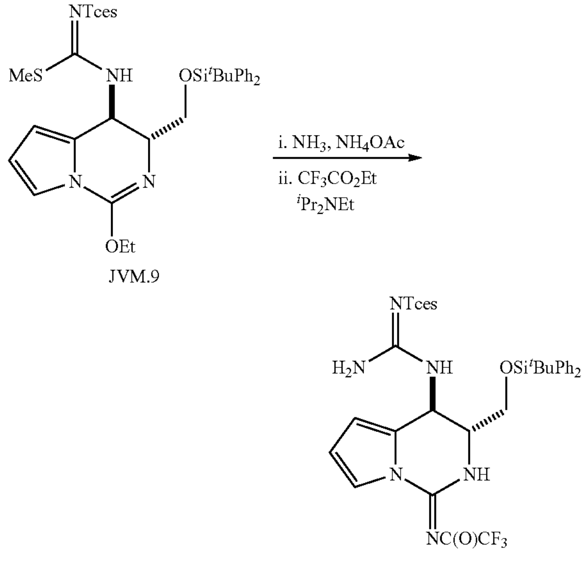

JVM.9

JVM.10

A 100 mL thick-walled tube containing a magnetic stir bar was charged with isourea JVM.9 (1.98 g, 2.71 mmol), $NH_4OAc$ (1.0 g, 13.0 mmol, 4.8 equiv), and $NH_3$ (40 mL of a 2.0 M solution in MeOH, 80.0 mmol, 29.5 equiv). The vessel was sealed with a Teflon screw-cap and the contents heated at 70° C. for 24 h. The reaction mixture was cooled to room temperature and concentrated under reduced pressure. $^1H$ NMR analysis of the unpurified product indicated that the material was of sufficient purity for subsequent use.

The unpurified guanidine was dissolved in 13.0 mL of MeCN and $^iPr_2NEt$ (2.36 mL, 13.5 mmol, 5.0 equiv) was added. The solution was then cooled to 0° C. and neat $CF_3CO_2Et$ (966 μL, 8.12 mmol, 3.0 equiv) was added. The contents were warmed to room temperature and stirred for 24 h. Following this time additional portions of $^iPr_2NEt$ (2.36 mL, 13.5 mmol, 5.0 equiv) and $CF_3CO_2Et$ (966 μL, 8.12 mmol, 3 equiv) were added. After stirring the mixture for 24 h, all volatiles were removed under reduced pressure. Purification of the isolated product by chromatography on silica gel (gradient elution: hexanes→2:1 hexanes/EtOAc afforded di-guanidine JVM.10 as a white solid (1.64 g, 79%). TLC $R_f$=0.43 (2:1 hexanes/EtOAc); $^1H$ NMR ($CD_3OD$, 400 MHz) δ 7.58-7.52 (m, 5H), 7.42-7.23 (m, 6H), 6.40-6.38 (m, 1H), 6.30 (dd, 1H, J=3.2, 3.2 Hz), 5.41 (br s, 1H), 4.64 (d, 1H, J=11.2 Hz), 4.60 (d, 1H, J=11.2 Hz), 4.07 (ddd, 1H, J=5.2, 5.2, 2.4 Hz), 3.78-3.66 (m, 2H), 0.94 (s, 9H) ppm; $^{13}C$ NMR ($CDCl_3$, 100 MHz) δ 169.2 (q, J=36.4 Hz), 155.9, 154.6, 135.54, 135.50, 132.13, 132.10, 130.3 (2H), 128.1 (2H), 125.0, 120.1, 116.4 (d, J=284 Hz), 114.5, 113.2, 94.0, 78.3, 63.5, 57.2, 43.7, 26.8, 19.1 ppm; IR (thin film) ν 3448, 3351, 1645, 1535, 1261, 1202, 1116, 855, 736, 702 $cm^{-1}$.

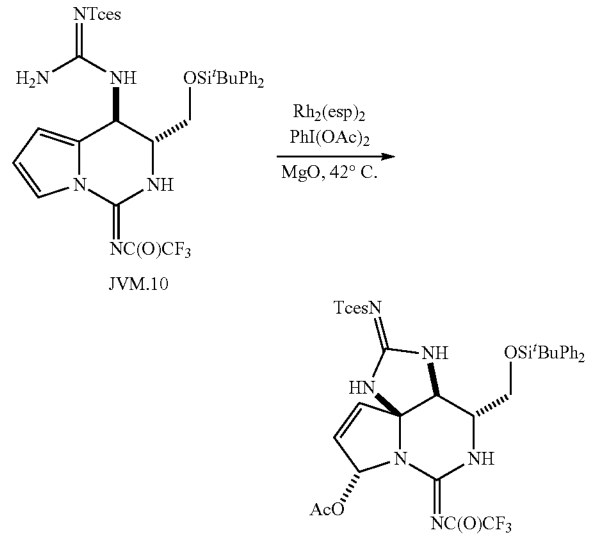

JVM.10

JVM.11

A 50 mL round bottom flask was charged with Tces-guanidine JVM.10 (131 mg, 0.17 mmol), $Rh_2(esp)_2$ (6.5 mg, 8.6 μmol, 0.05 equiv), $PhI(OAc)_2$ (137 mg, 0.43 mmol, 2.5 equiv), and MgO (31 mg, 0.77 mmol, 4.5 equiv). To the combined solids was added 6.8 mL of toluene. The resulting deep green reaction mixture was heated at 42° C. for 3 h. Following this time, the mixture was cooled to room temperature and applied directly to a column of silica gel. Gradient elution (hexanes→1:1 hexanes/EtOAc) afforded guanidine JVM.11 as a white solid (74 mg, 52%). TLC $R_f$=0.39 (3:2 hexanes/EtOAc); $^1H$ NMR ($CD_3OD$, 400 MHz) δ 7.63-7.56 (m, 4H), 7.48-7.39 (m, 6H), 6.80 (dd, 1H, J=2.0, 0.8 Hz), 6.31 (dd, 1H, J=6.0, 0.4 Hz), 6.09 (dd, 1H, J=6.0, 2.0 Hz), 4.65 (d, 1H, J=11.2 Hz), 4.62 (d, 1H, J=11.2 Hz), 4.33 (d, 1H, J=2.8 Hz), 3.86-3.82 (m, 1H), 3.74 (dd, 1H, J=10.4, 4.4 Hz), 3.51 (dd, 1H, J=7.6, 10.4 Hz), 2.07 (s, 3H), 1.01 (s, 9H); $^{13}C$ NMR ($CDCl_3$, 125 MHz) δ 169.8, 168.1 (q, J=36.5 Hz), 159.1, 157.7, 135.55, 135.52, 132.5, 131.9, 131.7, 130.6, 130.5, 130.4, 128.2, 128.1, 116.6 (d, J=285.0 Hz), 93.7, 84.7, 81.4, 78.2, 63.4, 57.0, 55.8, 26.7, 20.9, 19.1 ppm; IR (thin film) ν 3282, 2933, 2860, 1743, 1622, 1429, 1351, 1150, 1017, 853, 703 $cm^{-1}$.

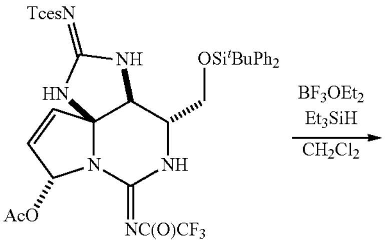

JVM.11

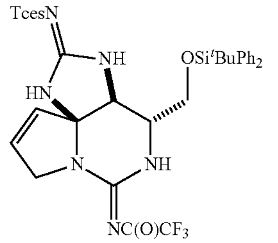

JVM.12

To a solution of allylic acetate JVM.11 (352 mg, 0.43 mmol) and triethylsilane (688 μL, 4.26 mmol, 10.0 equiv) in 9.0 mL of $CH_2Cl_2$ cooled to −78° C. was added $BF_3.OEt_2$ (216 μL, 1.70 mmol, 4.0 equiv). The reaction contents were allowed to slowly warm to 0° C. and stirred for 3 h at this temperature. Following this time, the reaction was quenched by the addition of 15 mL of saturated aqueous $NaHCO_3$. The resulting biphasic solution was stirred vigorously for 15 min. The mixture was then diluted with 25 mL of EtOAc and transferred to a separatory funnel. The organic layer was collected and the aqueous phase was extracted with 2×25 mL of EtOAc. The combined organic extracts were dried over $MgSO_4$ and concentrated under reduced pressure. Purification of the isolated material by chromatography on silica gel (gradient elution: hexanes→2:1 hexanes/EtOAc) afforded the olefin JVM.12 as a white solid (251 mg, 73%). TLC $R_f$=0.45 (1.5:1 hexanes/EtOAc); $^1H$ NMR ($CD_3OD$, 400 MHz) δ 7.64-7.57 (m, 4H), 7.48-7.37 (m, 6H), 6.17 (ddd, 1H, J=6.0, 2.0, 2.0 Hz), 5.93 (ddd, 1H, J=6.0, 2.0, 2.0 Hz), 4.62 (d, 1H, J=11.2 Hz), 4.59 (d, 1H, J=11.2 Hz), 4.35 (m, 2H), 4.09 (ddd, 17.0, 2.2, 2.2 Hz, 3.81-3.77 (m, 1H), 3.71 (dd, 1H, J=11.2, 5.2 Hz), 3.54 (dd, 1H, J=11.2, 8.4 Hz), 1.01 (s, 9H) ppm; $^{13}C$ NMR ($CDCl_3$, 125 MHz) δ 167.8 (q, J=35.6 Hz), 160.2, 157.8, 135.79, 135.77, 132.2, 132.1, 131.9, 130.50, 130.48, 128.3 (2H), 127.1, 116.8 (d, J=285 Hz), 93.9, 82.4, 78.4, 63.7, 59.1, 56.1, 53.9, 26.9, 19.3 ppm; IR (thin film) ν 3286, 2933, 1634, 1569, 1429, 1114, 907, 736 $cm^{-1}$.

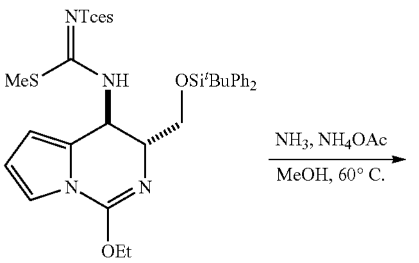

JVM.9

-continued

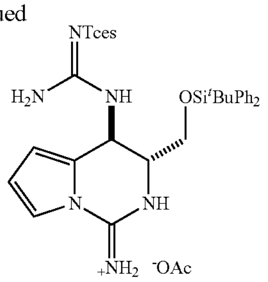

JVM.13

A 100 mL thick-walled tube containing a magnetic stir bar was charged with isourea JVM.9 (3.98 g, 5.44 mmol), $NH_4OAc$ (2.10 g, 27.2 mmol, 5.0 equiv), and $NH_3$ (32 mL of a 2.0 M solution in MeOH, 64.0 mmol, 11.8 equiv). The vessel was sealed with a Teflon screw-cap and the contents heated at 70° C. for 24 h. The reaction mixture was cooled to room temperature and concentrated under reduced pressure. Purification of the isolated material by chromatography on silica gel (gradient elution: 1:1 hexanes/EtOAc→3:17 MeOH/EtOAc) afforded di-guanidine JVM.13 as a white foam (3.38 g, 85%). TLC $R_f$=0.31 (6:1 EtOAc/MeOH); $^1H$ NMR ($CD_3OD$, 500 MHz) δ 7.56-7.61 (m, 4H), 7.36-7.45 (m, 7H), 6.45 (d, 1H, J=3.4 Hz), 6.42 (dd, 1H, J=3.4, 3.4 Hz), 5.44 (bs, 1H), 4.61 (d, 1H, J=2.5 Hz), 3.91-3.95 (m, 1H), 3.70 (dd, 1H, J=10.8, 4.5 Hz), 3.60 (dd, 1H, J=10.6, 5.8 Hz), 1.91 (s, 3H), 0.96 (s, 9H) ppm; $^{13}C$ NMR ($CD_3OD$, 125 MHz) δ 157.7, 151.9, 136.73, 136.72, 133.59, 133.47, 131.2 (2H), 129.09, 129.08, 128.5, 119.2, 115.5, 114.2, 95.7, 79.3, 65.3, 57.6, 44.8, 27.4, 20.0 ppm; IR (thin film) ν 2932, 1699, 1627, 1542, 1427, 1330, 1184, 1114, 1019, 846, 703 $cm^{-1}$.

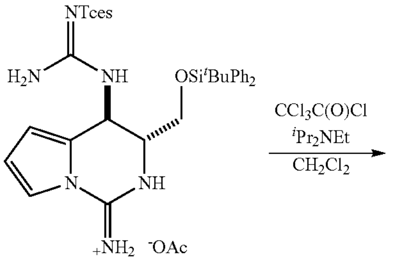

JVM.13

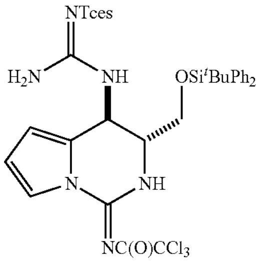

JVM.14

To a solution of di-guanidine JVM.13 (3.24 g, 4.43 mmol) in 44 mL of $CH_2Cl_2$ cooled to −20° C. were added sequentially $^iPr_2NEt$ (1.54 mL, 8.84 mmol, 2.0 equiv) and trichloroacetyl chloride (572 μL, 5.10 mmol, 1.15 equiv). The reaction mixture was stirred at −20° C. for 1 h and then quenched by the addition of 50 mL of saturated aqueous $NaHCO_3$. The biphasic contents were diluted with 100 mL of EtOAc and transferred to a separatory funnel. The organic layer was collected and the aqueous phase was extracted with 2×50 mL of EtOAc. The combined organic extracts were dried over $MgSO_4$ and concentrated under reduced pressure. Purification of the isolated material by chromatography on silica gel (gradient elution: 1:0→3:1 hexanes/EtOAc) afforded guanidine JVM.14 as a white solid (3.14 g, 89%). TLC $R_f$=0.43 (2:1 hexanes/EtOAc); mp 174-176° C.; $[\alpha]_{Na}$−51.6° (c=0.71, MeOH); $^1H$ NMR ($CD_3OD$, 400 MHz) δ 7.59 (dd, 1H, J=3.2, 1.6 Hz), 7.58-7.53 (m, 4H), 7.40-7.32 (m, 6H), 6.40-6.37 (m, 1H), 6.28 (dd, 1H, J=3.2, 3.2 Hz), 5.42 (br s, 1H), 4.65 (d, 1H, J=11.2 Hz), 4.61 (d, 1H, J=11.2 Hz), 4.12 (ddd, 1H, J=5.2, 5.2, 2.4), 3.75-3.66 (m, 2H), 0.93 (s, 9H) ppm; $^{13}C$ NMR ($CD_3OD$, 125 MHz) δ 173.9, 157.5, 155.5, 136.57, 136.55, 133.4, 133.3, 131.0(2), 128.96, 128.92, 127.3, 120.5, 114.0, 113.4, 97.3, 95.5, 79.2, 65.4, 58.2, 44.9, 27.2, 19.8 ppm; IR (thin film) ν 3464, 3358, 2931, 2859, 1603, 1589, 1363, 1212, 1115, 840, 739 $cm^{-1}$; HRMS ($ES^+$) calcd for $C_{29}H_{32}Cl_6N_6O_5SSi$ 814.0055 found 836.9949 ($MNa^+$).

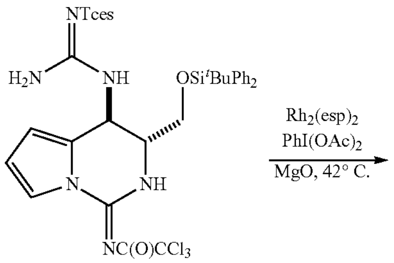

JVM.14

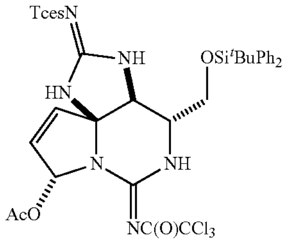

JVM.15

A 200 mL round bottom flask was charged with Tces guanidine JVM.14 (1.675 g, 2.05 mmol), $Rh_2(esp)_2$ (78 mg, 0.10 mmol, 0.05 equiv), $PhI(OAc)_2$ (1.65 g, 5.12 mmol, 2.5 equiv), and MgO (372 mg, 9.23 mmol, 4.5 equiv). To the combined solids was added 81 mL of $CH_2Cl_2$. The flask was sealed with a glass stopper and the resulting deep green reaction mixture was heated at 42° C. for 2.5 h. Following this time, the suspension was filtered through a small pad of Celite. The flask and filter cake were rinsed with $CH_2Cl_2$. To the combined filtrates was added 80 mL of a 1:1 solution of saturated aqueous $NaHCO_3$/saturated $Na_2S_2O_3$. The mixture was then transferred to a separatory funnel, the organic layer collected, and the aqueous phase extracted with 2×50 mL of EtOAc. The combined organic extracts were dried over $MgSO_4$ and concentrated under reduced pressure. Purification of the oily residue by chromatography on silica gel (gradient elution: 1:0→2:1 hexanes/EtOAc) afforded the desired tricycle JVM.15 as a white solid (1.12 g, 62%). TLC $R_f$=0.27 (2:1 hexanes/EtOAc); $^1H$ NMR ($CD_3OD$, 400 MHz) δ 7.64-7.58 (m, 4H), 7.47-7.40 (m, 6H), 6.86 (d, 1H, J=2.0 Hz), 6.32 (d, 1H, J=6.0 Hz), 6.10 (dd, 1H, J=5.8, 2.2 Hz), 4.67 (d, 1H, J=11.2 Hz), 4.63 (d, 1H, J=11.0 Hz), 4.36 (d, 1H, J=2.4 Hz), 3.86 (ddd, 1H, J=8.0, 4.4, 2.4 Hz), 3.73 (dd, 1H, J=10.4, 4.4 Hz), 3.51 (dd, 1H, J=10.6, 7.8 Hz), 2.09 (s, 3H), 1.02 (s, 9H) ppm; $^{13}C$ NMR ($CDCl_3$, 125 MHz) δ 172.6, 169.6, 158.8, 157.4, 135.52, 135.50, 132.4, 131.8, 131.7, 130.6, 130.4, 130.3, 128.17, 128.13, 95.8, 93.7, 85.2, 81.4, 78.2, 63.6, 56.8, 55.7, 26.8, 21.1, 19.1 ppm; IR (thin film) ν 3286, 2932, 2859, 1742, 1624, 1574, 1374, 1179, 1088, 1015, 909, 831, 735, 703 $cm^{-1}$; HRMS ($ES^+$) calcd for $C_{31}H_{34}Cl_6N_6O_7SSi$ 872.0110 found 895.0004 ($MNa^+$).

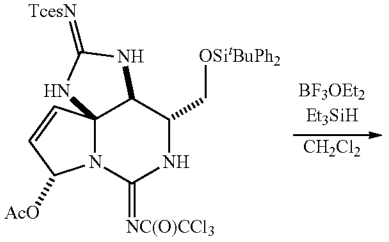

JVM.15

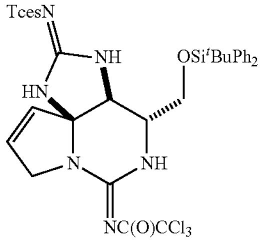

JVM.16

To a solution of allylic acetate JVM.15 (1.02 g, 1.16 mmol) and triethylsilane (940 μL, 5.82 mmol, 5.0 equiv) in 24.0 mL of $CH_2Cl_2$ cooled to −78° C. was added $BF_3.OEt_2$ (339 μL, 2.68 mmol, 2.3 equiv). The reaction contents were allowed to slowly warm to room temperature and stirred for 1.5 h. Following this time, the reaction was quenched by the addition of 40 mL of saturated aqueous $NaHCO_3$. The resulting biphasic solution was stirred vigorously for 15 min. The mixture was then diluted with 50 mL of EtOAc and transferred to a separatory funnel. The organic layer was collected and the aqueous phase was extracted with 2×25 mL of EtOAc. The combined organic extracts were dried over $MgSO_4$ and concentrated under reduced pressure. Purification of the isolated material by chromatography on silica gel (gradient elution: hexanes→2:1 hexanes/EtOAc) afforded olefin JVM.16 as a white solid (792 mg, 83%). TLC $R_f$=0.48 (2:1 hexanes/EtOAc); $^1H$ NMR ($CD_3OD$, 400 MHz) δ 7.65-7.59 (m, 4H), 7.46-7.37 (m, 6H), 6.17 (ddd, 1H, J=6.0, 1.8, 1.8 Hz), 5.95 (ddd, 1H, J=6.0, 2.2, 2.2 Hz), 4.63 (d, 1H, J=11.2 Hz), 4.60 (d, 1H, J=11.2 Hz), 4.37 (ddd, 1H, J=17.0, 2.2, 2.2 Hz), 4.32 (d, 1H, J=2.4 Hz), 4.17 (ddd, 1H, J=17.0, 2.0, 2.0 Hz), 3.82 (ddd, 1H, J=8.0, 4.4, 2.0 Hz), 3.70 (dd, 1H, J=10.6, 4.8 Hz), 3.55 (dd, 1H, J=10.6, 8.0 Hz), 1.02 (s, 9H) ppm; $^{13}C$ NMR ($CDCl_3$, 125 MHz) δ 172.4, 159.7, 157.7, 135.6(2), 131.9(2), 131.7, 130.3(2), 128.1(2), 127.0, 96.3, 93.8, 82.3, 78.2, 63.8, 58.3, 55.8, 53.8, 26.8, 19.1 ppm; IR (thin film) ν 3281, 2933, 2859, 1631, 1565, 1377, 1179, 1113, 908, 840, 734 $cm^{-1}$; HRMS ($ES^+$) calcd for $C_{29}H_{32}Cl_6N_6O_5SSi$ 814.0055 found 836.9951 ($MNa^+$).

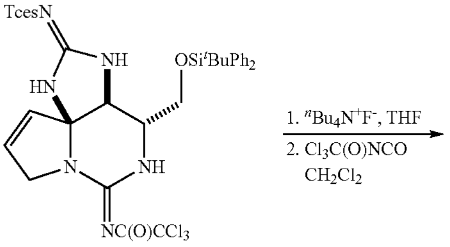

JVM.16

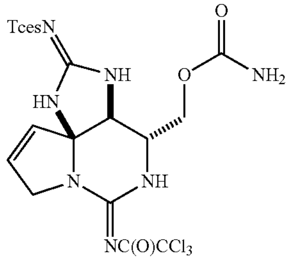

JVM.17

To a solution of olefin JVM.16 (206 mg, 0.25 mmol) in 5.0 mL of THF cooled to −78° C. was added tetrabutylammonium fluoride (305 μL of a 1.0 M solution in THF, 0.305 mmol, 1.2 equiv). The mixture was warmed to 0° C. and stirred at this temperature for 20 min Following this time, the reaction was quenched by the addition of 5.0 mL of saturated aqueous $NH_4Cl$. The contents were diluted with 10 mL of EtOAc and transferred to a separatory funnel. The organic layer was collected and the aqueous phase was extracted with 3×10 mL of EtOAc. The combined organic extracts were dried over $MgSO_4$ and concentrated under reduced pressure. This material was deemed suitably pure by $^1H$ NMR analysis and used immediately in the subsequent reaction. A sample of pure desilylated alcohol was obtained by chromatography on silica gel (2:1→1:2 hexanes/EtOAc). TLC $R_f$=0.33 (1:2 hexanes/EtOAc); $^1H$ NMR ($CD_3OD$, 400 MHz) δ 6.28 (ddd, 1H, J=6.2, 2.0, 2.0 Hz), 6.08 (ddd, 1H, J=6.2, 2.2, 2.2 Hz), 4.67 (d, 1H, J=11.2 Hz), 4.64 (d, 1H, J=11.2 Hz), 4.43 (m, 2H), 4.35 (d, 1H, J=2.8 Hz), 3.69-3.63 (m, 2H), 3.57 (dd, 1H, J=12.4, 8.4 Hz) ppm; $^{13}C$ NMR ($CDCl_3$, 125 MHz) δ 172.3, 159.4, 157.9, 130.9, 127.4, 96.5, 94.1, 83.1, 78.4, 61.7, 55.5, 55.2, 54.5 ppm; IR (thin film) ν 3289, 1616, 1562, 1379, 1175, 905, 841, 730 $cm^{-1}$.

To a solution of unpurified alcohol in 10.0 mL of $CH_2Cl_2$ cooled to −20° C. was added dropwise trichloroacetyl isocyanate (508 μL of a 0.5 M solution in $CH_2Cl_2$, 0.25 mmol). The mixture was stirred at −20° C. for 15 min, diluted with 20 mL EtOAc and quenched by the addition of 10 mL of saturated aqueous $NaHCO_3$. The contents were transferred to a separatory funnel and the organic layer was collected. The aqueous layer was extracted with 2×10 mL of EtOAc. The combined organic extracts were dried over $MgSO_4$, filtered and concentrated under reduced pressure. The isolated material was re-dissolved in 10.0 mL of MeOH and the solution stirred for 12 h. Following this time, the mixture was concentrated under reduced pressure. Purification of the oily residue by chromatography on silica gel (gradient elution: hexanes→1:2 hexanes/EtOAc) afforded carbamate JVM.17 as a white solid (121 mg, 76% over 2 steps). TLC $R_f$=0.18 (1:2 hexanes/EtOAc); $^1H$ NMR ($CD_3OD$, 400 MHz) δ 6.32 (ddd, 1H, J=6.2, 2.0, 2.0 Hz), 6.04 (ddd, 1H, J=6.2, 2.2, 2.2 Hz), 4.64 (d, 1H, J=11.2 Hz), 4.61 (d, 1H, J=11.2 Hz), 4.44 (d, 1H, J=2.4 Hz), 4.43-4.40 (m, 2H), 4.15-4.03 (m, 2H), 3.86 (ddd, 1H, J=7.4, 4.8, 2.4 Hz) ppm; $^{13}C$ NMR ($CD_3OD$, 125 MHz) δ 172.9, 161.3, 159.0, 158.6, 131.7, 129.0, 97.7, 95.5, 83.3, 79.4, 64.3, 60.5, 55.0, 54.7 ppm; IR (thin film) ν 3292, 2951, 2457, 1723, 1617, 1565, 1494, 1341, 1175, 1086, 895, 842, 752 $cm^{-1}$; HRMS ($ES^+$) calcd for $C_{14}H_{15}Cl_6N_7O_6S$ 618.8936 found 641.8830 ($MNa^+$).

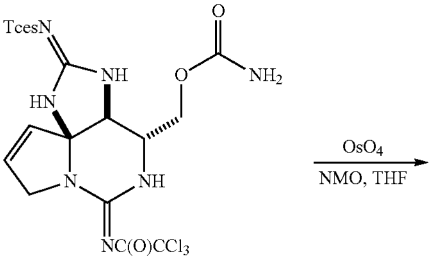

JVM.17

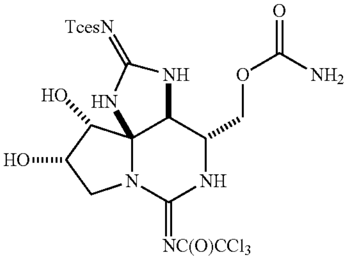

JVM.18

To a solution of olefin JVM.17 (117 mg, 0.20 mmol) in 4.0 mL of THF were added sequentially N-methylmorpholine-N-oxide (44 mg, 0.38 mmol, 2.0 equiv) and $OsO_4$ (24 μL of a 4% aqueous solution, 3.8 μmol, 0.02 equiv). The reaction mixture was stirred for 12 h and then quenched by the addition of 4 mL of saturated aqueous $Na_2S_2O_3$. The contents were diluted with 8 mL of EtOAc and transferred to a separatory funnel. The organic layer was collected and the aqueous phase was extracted with 2×4 mL of EtOAc. The combined organic extracts were dried over $MgSO_4$ and concentrated under reduced pressure. Purification of the oily residue by chromatography on silica gel (gradient elution: 2:1→0:1 hexanes/EtOAc) afforded the diol JVM.18 as a white solid (102 mg, 82%). TLC $R_f$=0.33 (neat EtOAc); $^1H$ NMR ($CD_3OD$, 400 MHz) δ 4.63 (s, 2H), 4.56 (d, 1H, J=2.8 Hz), 4.54 (ddd, 1H, J=7.6, 7.6, 4.0 Hz), 4.21-4.14 (m, 2H), 3.98 (dd, 1H, J=11.6, 8.0 Hz), 3.95 (d, 1H, J=4.0 Hz), 3.79 (ddd, 1H, J=7.2, 6.0, 2.8 Hz), 3.45 (dd, 1H, J=11.6, 7.6 Hz) ppm; $^{13}C$ NMR ($CD_3OD$, 125 MHz) δ171.6, 160.4, 158.2, 157.8, 96.7, 94.3, 80.7, 78.2, 76.1, 67.9, 63.0, 55.7, 53.4, 50.0 ppm; IR (thin film) ν 3299, 2985, 1711, 1618, 1567, 1376, 1321, 1177, 1088, 902, 845, 760 $cm^{-1}$; HRMS ($ES^+$) calcd for $C_{14}H_{17}Cl_6N_7O_8S$ 652.8990 found 675.8892 ($MNa^+$).

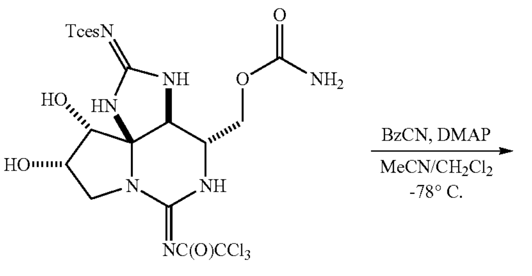

JVM.18

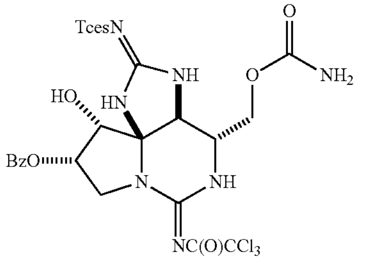

JVM.19

Benzoyl cyanide (1.64 mL of a 0.1 M solution in $CH_2Cl_2$, 0.164 mmol, 1.1 equiv) was added dropwise to a −78° C. solution of diol JVM.18 (98 mg, 0.149 mmol) and 4-dimethylaminopyridine (72.8 mg, 0.60 mmol, 4.0 equiv) in 6.0 mL of a 3:1 $CH_2Cl_2$/MeCN mixture. The reaction was stirred at −78° C. for 1.5 h and then quenched with 50 μL of MeOH. The contents were diluted with 10 mL of EtOAc and 5 mL of saturated aqueous $NaHCO_3$, and transferred to a separatory funnel. The organic layer was collected and the aqueous phase was extracted with 2×10 mL of EtOAc. The combined organic extracts were dried over $MgSO_4$ and concentrated under reduced pressure. Purification of the oily residue by chromatography on silica gel (gradient elution: hexanes→1:2 hexanes/EtOAc) afforded the benzoate JVM.19 as a white solid (78 mg, 69%). $^1H$ NMR ($CD_3OD$, 400 MHz) δ 8.12-8.09 (m, 2H), 7.66-7.61 (m, 1H), 7.53-7.48 (m, 2H), 5.61 (ddd, 1H, J=8.4, 7.6, 4.0 Hz), 4.67 (d, 1H, J=10.8), 4.64 (d, 1H, J=10.8 Hz), 4.63 (d, 1H, J=3.2 Hz), 4.40 (d, 1H, J=4.0 Hz), 4.29-4.15 (m, 3H), 3.85 (ddd, 1H, J=8.4, 5.2, 2.8 Hz), 3.77 (dd, 1H, J=11.8, 7.4 Hz) ppm; $^{13}C$ NMR ($(CD_3)_2CO$, 100 MHz) δ 171.0, 165.5, 160.0, 158.1, 156.15, 133.5, 129.8, 129.5, 128.6, 94.4, 81.0, 77.9, 74.3, 71.0, 62.5, 54.4, 53.1, 47.9 ppm; IR (thin film) ν 3294, 2985, 1715, 1620, 1274, 1177, 902, 846, 760, 716 $cm^{-1}$.

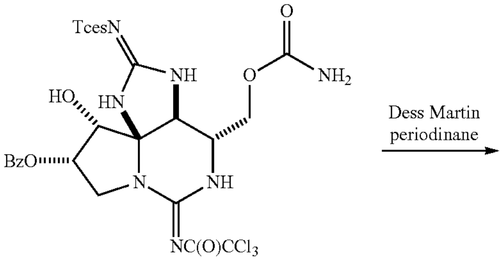

JVM.19

-continued

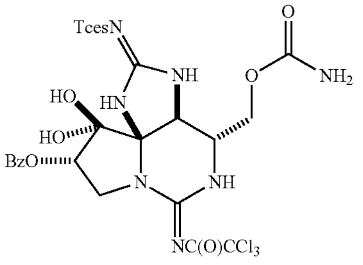

JVM.20

To a solution of benzoate JVM.19 (12.7 mg, 16.7 μmol) in 700 μL of $CH_2Cl_2$ was added Dess-Martin periodinane (10.9 mg, 26.0 μmol, 1.5 equiv). The reaction was stirred for 20 min and then quenched by the addition of 700 μL of 1:1 saturated aqueous $NaHCO_3$/saturated aqueous $Na_2S_2O_3$. The biphasic mixture was stirred vigorously for 10 min, diluted with 1 mL of $CH_2Cl_2$ and transferred to a separatory funnel. The organic layer was collected and the aqueous phase was extracted with 1×1 mL of $CH_2Cl_2$. The combined organic extracts were applied directly to a column of silica gel. Purification by chromatography on silica gel (gradient elution: hexanes→1:2 hexanes/EtOAc) afforded JVM.20 as a white solid (10 mg, 78%). $^1H$ NMR ($(CD_3)_2CO$, 400 MHz) δ 9.44 (br s, 1H), 8.20-8.17 (m, 2H), 7.70-7.65 (m, 1H), 7.56-7.50 (m, 2H), 6.76 (br s, 1H), 6.65 (br s, 1H), 6.00 (br s, 2H), 5.72 (dd, 1H, J=8.6, 7.0 Hz), 4.87 (d, 1H, J=2.4 Hz), 4.61 (s, 2H), 4.35 (dd, 1H, J=12.2, 8.6 Hz), 4.28-4.25 (m, 2H), 4.08 (m, 1H), 3.62 (dd, 1H, J=12.2, 7.2 Hz) ppm; $^{13}C$ NMR ($(CD_3)_2CO$, 100 MHz) δ 171.0, 165.9, 160.2, 158.6, 156.2, 133.7, 130.0, 129.2, 128.5, 98.4, 96.8, 94.4, 80.6, 77.9, 73.6, 62.6, 54.9, 53.7, 47.5 ppm; IR (thin film) ν 3286, 1714, 1618, 1566, 1318, 1274, 1175, 1088, 1016, 903 $cm^{-1}$.

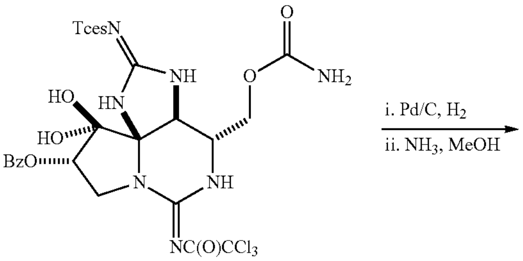

JVM.20

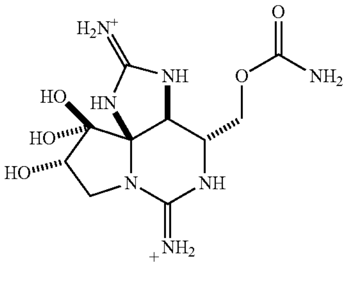

11β-OH-STX

To a solution of diol JVM.20 (5.8 mg, 7.6 μmol) in 2.0 mL of MeOH was added 50 μL of $CF_3CO_2H$. The reaction was stirred for 30 min and then Pd/C (22 mg of 10 wt. %, 0.021 mmol, 2.75 equiv) was added. The reaction vessel was placed in a high pressure Parr bomb, which was sealed and flushed six times with $H_2$ gas (800 psi). The bomb was pressurized to 800 psi of $H_2$ and the contents stirred at this pressure for 12 h. After this time, the bomb was vented and the reaction mixture was filtered through a Fisher 0.2 μm PTFE syringe filter. The flask and filter were washed with 2 mL of MeOH and the filtrate concentrated under reduced pressure. The thin-film residue was dissolved in 1.0 mL of a 2.0 M MeOH solution of $NH_3$. After stirring this solution for 15 min, all volatiles were removed under reduced pressure. The isolated material was immediately dissolved in 2.0 mL of a 0.5 M aqueous $CF_3CO_2H$ solution and was stirred for 24 h. Concentration of this solution under reduced pressure afforded the product as a thin film, which was purified by reversed-phase HPLC (Alltima C18, 10 μM, 10×250 mm column, eluting with gradient flow over 20 min of 1:99→30:70 MeCN/10 mM aqueous $C_3F_7CO_2H$, 214 nm UV detection). At a flow rate of 6 mL/min, 11β-OH-STX had a retention time between 13.7-15.5 min and was isolated as a white, hygroscopic solid (4.6 mg, 83%). $^1$H NMR ($D_2O$, 400 MHz) δ 4.80 (1H), 4.45 (dd, 1H J=8.0, 7.2 Hz), 4.33 (dd, 1H, J=11.6, 9.6 Hz), 4.07-3.98 (m, 2H), 3.82 (dd, 1H, J=9.6, 4.4 Hz), 3.27 (dd, 1H, J=10.4, 7.2 Hz) ppm; $^{13}$C NMR ($D_2O$, 600 MHz, determined by HMBC and HSQC) δ 158.7, 157.6, 155.5, 97.6, 81.7, 70.5, 63.0, 57.5, 53.0, 48.5 ppm; HRMS ($ES^+$) calcd for $C_{10}H_{17}N_7O_5$ 315.1291 found 316.1366 ($MH^+$).

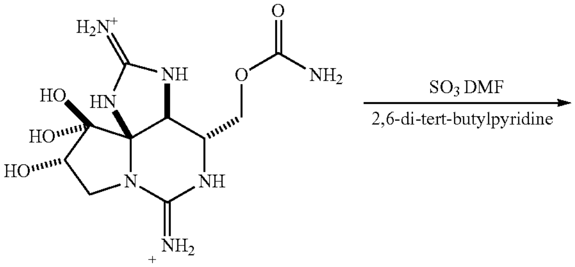

11β-OH-STX

-continued

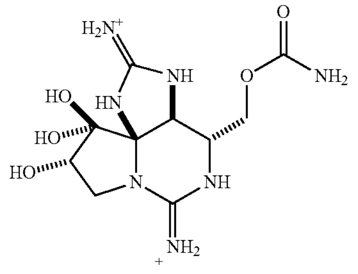

GTX 3

To a solution of 11β-OH-STX (7.3 mg, 9.8 μmol) and 2,6-di-tert-butyl-4-methylpyridine (55 mg, 0.27 mmol, 27.5 equiv) was added dropwise $DMF.SO_3$ (893 μL of a 0.1 M solution in N-methylpyrrolidinone, 89.3 μmol, 9.1 equiv). The reaction mixture was stirred for 3 h, then quenched by the addition of 300 μL of $H_2O$. The solution was concentrated in vacuo and the thin-film residue was purified by reversed-phase HPLC (Alltima C18 column, 10 μM, 10×250 mm column, eluting with gradient flow over 20 min of 1:99 MeCN/10 mM aqueous $C_3F_7CO_2H$, 214 nm UV detection). At a flow rate of 6 mL/min, GTX 3 had a retention time between 6.8-7.9 min and was isolated as a white, hygroscopic solid (4.2 mg, 71%). $[\alpha]_{Na}$+43.3° (c=0.40 ($CF_3CF_2CF_2CO_2^-$ salt)); $^1$H NMR ($D_2O$, 400 MHz) δ 4.96 (dd, 1H, J=8.2, 6.8 Hz), 4.82 (d, 1H, J=1.2 Hz), 4.30 (dd, 1H, J=11.8, 9.4 Hz), 4.17 (dd, 1H, J=10.6, 8.2 Hz), 4.06 (dd, 1H, J=11.8, 5.4 Hz), 3.82 (ddd, 1H, J=9.0, 5.4, 1.2 Hz), 3.58 (dd, 1H, J=10.6, 6.8 Hz) ppm; $^{13}$C NMR ($D_2O$, 600 MHz, determined by HMBC and HSQC) δ 158.7, 157.6, 155.5, 97.3, 81.6, 75.7, 63.0, 57.2, 53.1, 47.4 ppm; HRMS ($ES^+$) calcd for $C_{10}H_{15}N_7O_7S$ 377.0754 found 378.0833 ($MH^+$).

Comparison of Spectral Data for Synthetic and Natural (+)-Gonyautoxin 3 (see, Onodera, H.; Satake, M.; Oshima, Y.; Yasumoto, T.; Carmichael, W. W. *Nat. Toxins.* 1997, 5, 146-151)

| | Synthetic GTX 3 | | Natural GTX 3 | |
|---|---|---|---|---|
| Position | $^{13}$C | $^1$H | $^{13}$C | $^1$H |
| 2 | 55.5 | | 55.5 | |
| 4 | 81.6 | | 81.6 | |
| 5 | 57.2 | 4.82 (d, 1H, J = 1.2 Hz) | 57.2 | 4.82 (s, 1H) |
| 6 | 53.1 | 3.82 (ddd, 1H, J = 9.0, 5.4, 1.2 Hz) | 53.0 | 3.82 (dd, 1H, J = 9.3, 5.4 Hz) |
| 8 | 57.6 | | 57.6 | |
| 10 | 47.4 | 4.17 (dd, 1H, J = 10.6, 8.2 Hz)<br>3.58 (dd, 1H, J = 10.6, 6.8 Hz) | 47.5 | 4.17 (dd, 1H, J = 10.5, 8.4 Hz)<br>3.58 (dd, 1H, J = 10.5, 7.2 Hz) |
| 11 | 75.7 | 4.96 (dd, 1H, J = 8.2, 6.8 Hz) | 75.7 | 4.96 (dd, 1H, J = 8.4, 7.2 Hz) |
| 12 | 97.3 | | 97.3 | |
| 13 | 63.0 | 4.06 (dd, 1H, J = 11.8, 5.4 Hz)<br>4.30 (dd, 1H, J = 11.8, 9.4 Hz) | 63.0 | 4.06 (dd, 1H, J = 11.7, 5.4 Hz)<br>4.29 (dd, 1H, J = 11.7, 9.3 Hz) |
| 14 | 58.7 | | 58.7 | |

Example 3

Having utilized the advanced oxazolidinone intermediate to access a number of saxitoxin-derived molecular probes with long linear side chains, we further exploited this chemistry to synthesize a number of branched derivatives. These molecules have greater steric bulk near the saxitoxin core, potentially destabilizing binding of the toxin. We envision employing these molecules in conjunction with mutant sodium channels to map out the steric environment around the side chain when STX is bound in the channel. Further, one can imagine engineering a saxitoxin derivative incorporating an additional chemical moiety (a "bump") that binds with low affinity to the wild-type channel but with high affinity to a mutant with a corresponding "hole." (*Annual Review of Cell and Developmental Biology* 2001, 17, 405-433, which is incorporated herein by reference).

In initial studies, we designed a set of molecules with branching at the nitrogen of the carbamate side chain as well as the carbon adjacent to the nitrogen. Two mutant channels were also constructed by site-directed mutagenesis. The initial patch-clamping results are presented in Example 3, Table 1. The β-STXol data points were collected to demonstrate that STX and its derivatives were oriented similarly within the channel pore. The similar reductions in affinity for STX to β-STXol and for cyclohexyl STX to cyclohexyl β-STXol provide strong initial evidence that the two molecules both reside in a similar orientation in the channel pore.

Though none of these saxitoxin derivatives show greater affinity for one of the two mutants over the wild-type channel, they do demonstrate notable affinity differences compared to native STX. In particular, the parent compound is destabilized by ~40-fold when tested against the M1240A mutant while the cyclohexylamine derivative is only destabilized by 4-fold. This difference potentially suggests that mutation of methionine to the smaller alanine creates a larger void space for the carbamate to occupy thereby better accommodating the cyclohexyl side chain. Additional mutations of the sodium channel are currently being explored to further investigate potential creation of a "hole" to accommodate a larger carbamate side chain (a "bump").

TABLE 1

Affinity of various STX derivatives for $Na_v1.4$ and its mutants

| Compound | WT $Na_v1.4$ | I757A $Na_v1.4$ | M1240A $Na_v1.4$ |
|---|---|---|---|
| 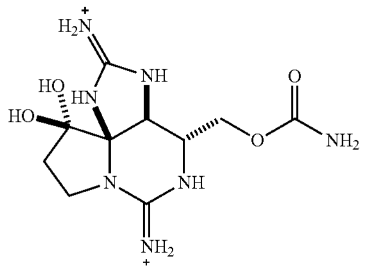 | $IC_{50}$ = 2.4 nM | $IC_{50}$ = 30 nM | $IC_{50}$ = 90 nM |
| 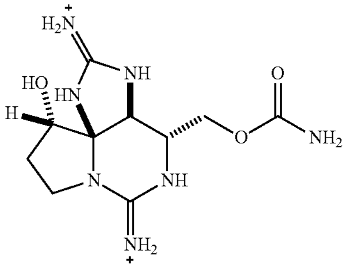 [SMILES: NC(=O)OC[C@@H]1NC(=[NH2+])N2CC[C@H](O)[C@@]23NC(=[NH2+])N[C@@H]13] | | — | — |
| | = 230 nM | = 700 nM | = 1 μM |
| 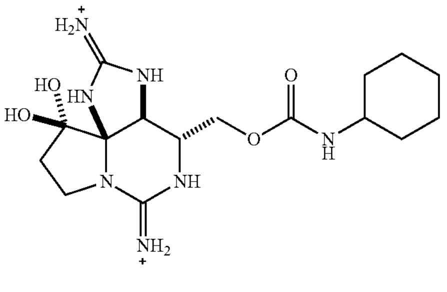 | | | |

TABLE 1-continued

| Affinity of various STX derivatives for $Na_v1.4$ and its mutants | | | |
|---|---|---|---|
| Compound | WT $Na_v1.4$ | I757A $Na_v1.4$ | M1240A $Na_v1.4$ |
| 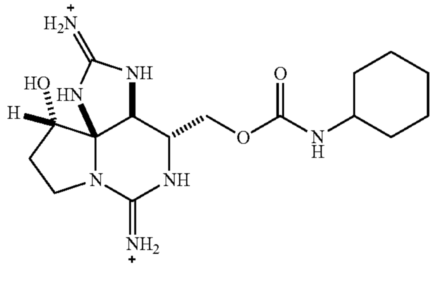 [SMILES: [NH2+]=C1N[C@H]2[C@H](COC(=O)NC3CCCCC3)NC(=[NH2+])N3CC[C@H](O)[C@]23N1] | = ~600 μM (extrapolated) | — | — |
| 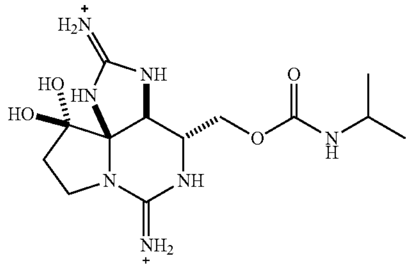 | = 50-60 nM | = 150-200 nM | = 500 nM |
| 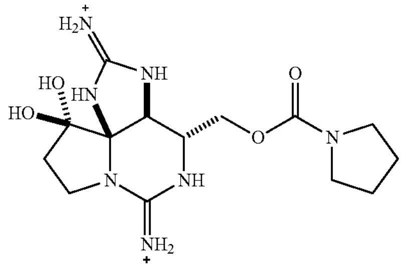 | = 15-30 nM | = 100 nM | = 500 nM |
| 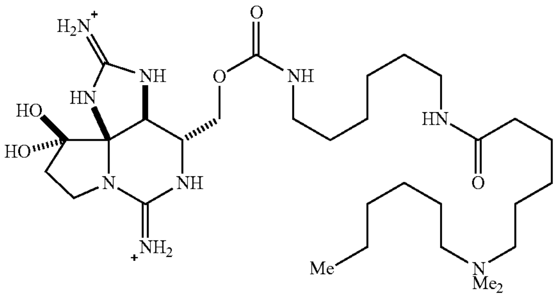 | = 10-20 nM | | |

Figure 12:
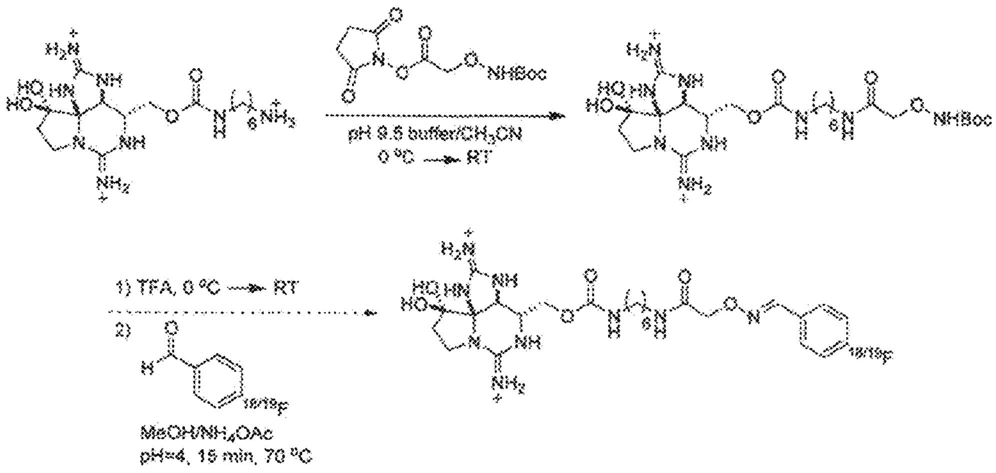
FIG. 12 provides an example of a synthetic approach for the synthesis of a saxitoxin analogue linked to a label suitable for use in imaging studies.

In addition to these structural studies, we have designed other probes for imaging sodium channels in vivo. Specifically, we have designed an STX derivative in which $^{18}F$-labeled benzaldehyde can be incorporated via a physiologically stable oxime linkage. (*Journal of Nuclear Medicine* 2008, 49, 804-813, which is incorporated herein by reference). An exemplary synthetic route to this molecule from our commonly employed hexylamine-terminated intermediate is presented in FIG. 12. FIG. 12 illustrates the synthetic scheme for synthesis of PET-imaging probe. Synthetic studies indicate that the initial coupling can be successfully performed while the work of Cheng, et al provides confidence that the oxime linkage should be readily formed and stable in vivo.

Example 4

Example 4 describes the effect of (+)-saxitoxin applied by cutaneous microneedles. When testing the analgesic efficacy of saxitoxin by means of microneedle delivery, all rats were deeply anesthetized with isoflurane (2.5%). Both the left and right cheeks of each male, Sprague-Dawley rat (Harlan, 250 g) were completely depilated and thereafter thoroughly cleansed with ethanol wipes.

While still deeply anesthetized, each rat was subject to microneedle patch application. With a pair of blunt-edged forceps, the tester pulled back on the skin of one cheek in order to make the rat's skin taut. At this point, the tester would push a single microneedle patch containing saxitoxin down into the skin. Likewise, the same application process was carried out on the contralateral cheek; this patch however served as a control and had no drugs within the microneedle tips. Each test group consisted of 6 rats that received the saxitoxin.

The microneedle patches remained on the rats' skin for approximately 20 minutes in order to ensure adequate drug delivery. During this time, the rats were taken off isoflurane and allowed to recover in their individual cages. Once their patches were removed, the rats were lightly anesthetized with an IP injection of 25% urethane (1 mg/kg), which allowed for behavioral measurements without disruptive movement. Beginning 20 minutes later, cheek withdrawal latencies for continuous, noxious heat were assessed repeatedly at 10-minute intervals over a 30-minute timeframe and then every 30 minutes thereafter for the next 2.5 hours. Using a heating lamp (set to 40V and positioned 7 cm above the rat's cheeks), focused, radiant heat was applied to the rat's left cheek; the time it took for the rat to respond to the heat stimuli was recorded. The same process was repeated for the right cheek. Rats that did not respond after 20 seconds of heat exposure were considered nonresponsive.

Figure 13:
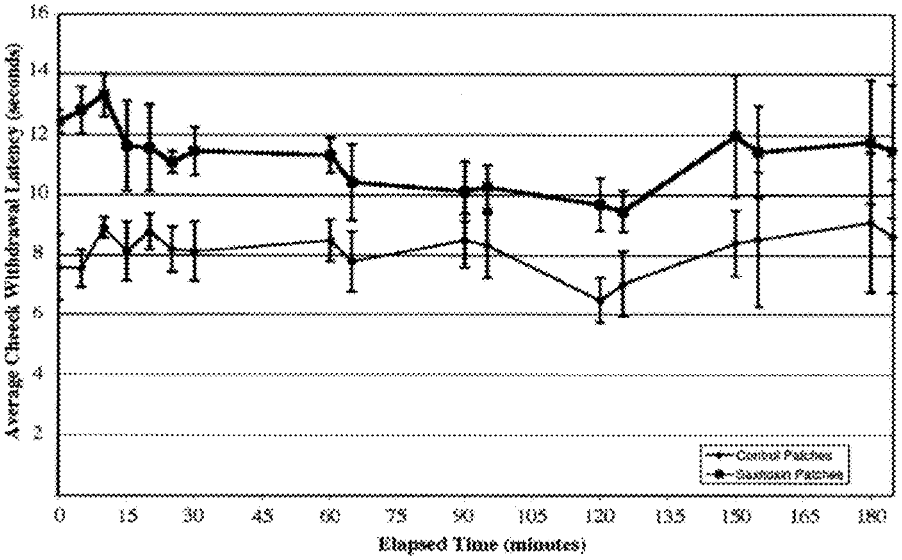
FIG. 13 provides graphic illustration of the results of studies on rats administered STX (0.44 μg) by microneedle patch as compared with control rats. Skin treated with STX was significantly less responsive to noxious stimulus (heat) than control.

Results:

Skin treated with the saxitoxin patch was significantly ($p<0.05$, ANOVA) less responsive to noxious heat than was control skin (FIG. 13). Thus, the latency to response to heat was 2-2.5 s higher than was observed for skin treated with a control microneedle patch, representing a moderate decrease in pain sensitivity.

Example 5

Figure 14A:
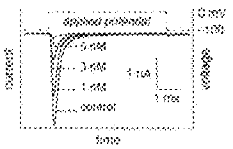
FIG. 14A illustrates the results of experiments showing the effects of several C-13 modified forms of STX on sodium currents ($rNa_v1.4$ currents in CHO cells).
Figure 14B:
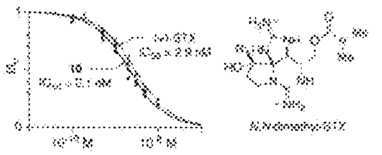
FIG. 14B plots the normalized current versus the applied concentration, and notes the $IC_{50}$ values for STX and for saxitoxin analogue N,N-dimethyl-saxitoxin (compound 10 shown in FIG. 14B).
Figure 14C:
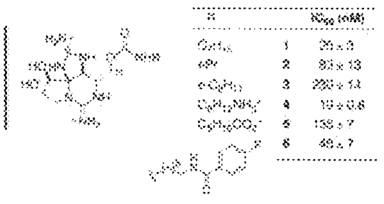
FIG. 14C presents $IC_{50}$ values for several saxitoxin analogues with substituents R as shown in the figure.

5.1 Saxitoxin and gonyautoxin can be synthesized and modified. Syntheses of saxitoxin and gonyautoxin 2/3 have been achieved in our labs, along with methods to modify the form and function of these unique toxins (FIG. 14A, FIG. 14B, and FIG. 14C). A detailed discussion of our analysis of the STX problem has appeared in the literature. (see, (a) Fleming, J. J., M. D. McReynolds, and J. Du Bois, (+)-*saxitoxin: a first and second generation stereoselective synthesis*. J Am Chem Soc, 2007. 129(32): p. 9964-75. (b) Fleming, J. J. and J. Du Bois, A synthesis of (+)-*saxitoxin*. J Am Chem Soc, 2006. 128(12): p. 3926-7.) Our studies have demonstrated that modifications to the primary carbamate unit in STX (C13) do not dramatically alter the affinity of this compound for TTX-s $Na_V$ channels. Based on these data, we have prepared an amine-derived STX ($NH_2$-STX) to which different prosthetic groups (e.g., fluorophores, $^{18}$F-labels, biotin) may be attached. The synthetic route to this compound and related structures has been highly optimized to facilitate multi-gram production of key intermediates. We have used these chemistries to prepare Oregon-Green-STX and Cy5-STX conjugates, and have tested these compounds for potency against $rNa_V1.4$ expressed in CHO cells. Whole-cell voltage-clamp recording indicate that both molecules retain mid-nanomolar affinity against this $Na_V$ isoform. We are currently conducting electrophysiology measurements against heterologous $rNa_V1.7$ and intend to also perform binding studies with $rNa_V1.3$ and the TTX-r channel, $rNa_V1.8$ as a control.

We have demonstrated that $NH_2$-STX can be efficiently coupled to the N-hydroxysuccinimide ester of 4-fluorobenzoic acid (SFB) to give [19F]benzamide-STX. This non-radioactive analogue of our first-generation PET agent displays an $IC_{50}$ of 46±7 nM against $rNa_V1.4$, as determined by whole-cell electrophysiology measurements Importantly, the conditions for attaching SFB to $NH_2$-STX are suitable for generation of the [18F] analogue (see below).

Figure 15:
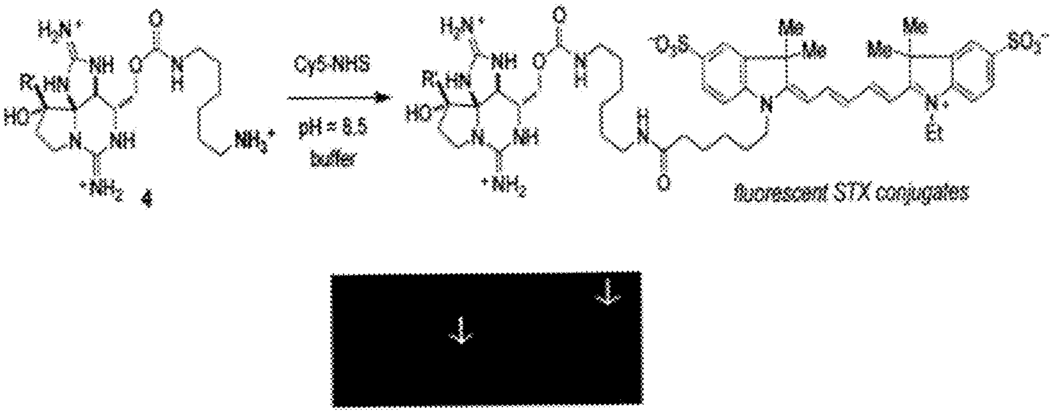
FIG. 15 illustrates a method of synthesizing a fluorescent STX conjugate and shows the fluorescence of such molecules bound to sodium channels in CHO cells. Single-step chemoselective NHS-ester conjugation to $NH_2$-STX 4. Single-molecule images of Cy5-STX bound to rNav1.4 expressed in CHO cells (figure courtesy of H. Lu and W. E. Moerner, Stanford University).

Gonyautoxins (GTXs) comprise a family of sulfated guanidinium toxins closely related to STX in both structure and function. These molecules display low-to-mid nanomolar potencies against TTX-s $Na_V$ s. Interestingly, qualitative measurements in our lab have revealed that GTX 3 has considerably slower off-rate binding kinetics as compared to STX. With our ability to access these toxins through de novo synthesis, similar steps have been taken to prepare carbamate derivatives and to evaluate the influence on channel binding of these novel constructs. In addition, we have synthesized an analogous $NH_2$-GTX 3 and have demonstrated that this material will smoothly undergo a single-step chemical ligation with reactive NHS esters of fluorogenic dyes (FIG. 15). We are now uniquely positioned to conduct comparative in vivo studies (i.e., biodistribution, excretion rates, metabolism) between labeled forms of STX and GTX 3, in addition to other non-natural derivatives of these toxins having altered binding affinities and binding kinetics to the channel (i.e., slower off-rate kinetics, see below). These studies are made possible only through the advent of synthetic protocols for the de novo assembly of these toxins.

5.2 Carbamate-Modified STXs Retain Nanomolar Affinity for $Na_V$ and can have Longer Duration of Action.

A key question to address is whether saxitoxin can be functionalized with an imaging agent without significantly perturbing binding efficacy. We have prepared novel fluorescent- and PET-conjugates of STX by devising a scheme that capitalizes on the availability of STX derivatives such as 4 (FIG. 15) for selective chemical ligation to electrophilic ester reagents. For example, compound 4, when treated under mild alkaline conditions with the Cy5-N-hydroxysuccinimidoyl (NHS) ester, affords exclusively the coupled product. This ligation step is typically complete in <3 h and is compatible with a variety of NHS ester derivatives, thus making possible the synthesis of Oregon Green, Cy5 and p-19F-benzamide derivatives. These compounds all retain low-to-mid nanomolar potencies against $Na_V1.4$, as determined by electrophysiology recordings.

Figure 16:
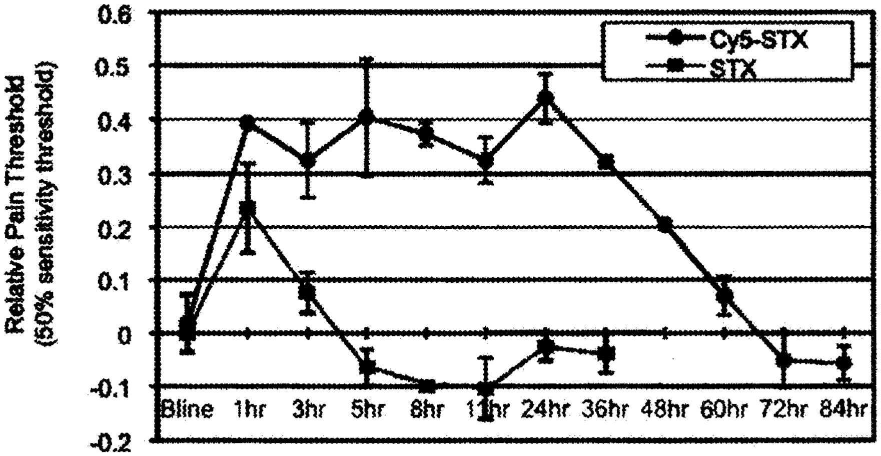
FIG. 16 shows measurements of relative local anesthesia to mechanical stimulation following injection of STX-Cy5 conjugate (shown in red) or STX (shown in blue) directly into the hindpaw of a mouse. Measurements of relative local anesthesia to mechanical stimulation following direct hindpaw injection of STX-Cy5 or STX.

We have observed pronounced differences between STX and Cy5-STX in the period of anesthesia (decreased sensitivity or increased pain threshold) to mechanical stimulation when murine animals are given a subcutaneous injection of either Cy5-STX or native STX into the hindpaw, (FIG. 16). With Cy5-STX, local anesthesia persists for 60 hours or more than 20 times longer than STX itself. To account for this dramatic difference in drug duration of action, it is believed that the large lipophilic Cy5 dye molecule may associate tightly to the plasma membrane to serve, in effect, as a membrane 'anchor' with the STX moiety nestled in the outer mouth of the channel pore.

5.3 Synthesis of [18F]Benzamide-STX.

Figure 17:
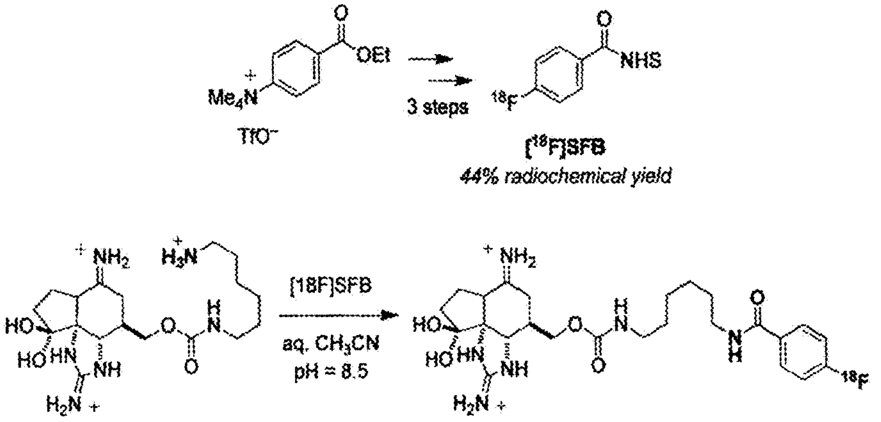
FIG. 17 shows a radiochemical synthesis of N-succinimidyl 4-[$^{18}$F]fluorobenzoate, [$^{18}$F]SFV, and chemoselective ligation to $NH_2$-STX to produce an in vivo imaging agent for TTX-s $Na_v$ isoforms.

We have shown that $NH_2$-STX can be coupled selectively to reactive NHS-esters such as [19F]-4-fluorobenzoic acid. Recently, this coupling reaction has been successfully reproduced with [18F]-SFB to generate radiolabeled [18F]benzamide-STX (FIG. 17). The details for [18F]-SFB preparation have been described previously. (see, (a) Li, Z. B., et al., 18*F-Labeled BBN-RGD Heterodimer for Prostate Cancer Imaging*. J Nucl Med, 2008. 49(3): p. 453-61. (b) Wu, Z., et al., 18*F-labeled mini-PEG spacered RGD dimer* (18*F-FPRGD*2): *synthesis and microPET imaging of alphavbeta*3 *integrin expression*. Eur J Nucl Med Mol Imaging, 2007. 34(11): p. 1823-31.) Coupling to $NH_2$-STX is performed in aqueous $CH_3CN$ at pH 9.5 and the product is purified by preparative HPLC. All of this chemistry can be completed semi-automatically using a modified GE TRACERlab FX-FN synthesis module (GE Medical Systems; Milwaukee, Wis.). The purified fraction of [18F]benzamide-STX is sterilized with a sterile filter to give the final product. A sample of formulated [18F]benzamide-STX was removed from the prepared batch vial with a sterile syringe that is part of a pre-assembled batch vial. This aliquot is distributed for the following QC tests: visual inspection, radiochemical and chemical purities, specific radioactivity, sterility, pyrogenicity, pH, residual solvent analysis, radionuclidic identity, and bacterial endotoxins (LAL test).

5.4 Preliminary Biodistribution Studies of [18F]Benzamide-STX Indicate Stability of the Tracer in Vivo.

Following intravenous injection of [18F]STX into mice (n=3), organs were harvested to determine biodistribution of the radiolabel. No statistically relevant amount of bone uptake (0.05±0.03% ID/gm) is observed, indicating that defluorination of the fluorobenzamide group does not occur in vivo. Additionally, it appears that urinary excretion is the major pathway for tracer clearance with 10.7±8.9% ID/gram found in the kidneys. As expected, given the dicationic nature of the STX probe, no tracer was detected in the brain (0.03±0.02% ID/gm); accordingly, no central nervous system effects are to be expected from this radiotracer.

5.5 [18F]Benzamide-STX Small Animal PET-MRI (MicroPET-MRI) Shows Increased Binding of Tracer to Site of Nerve Injury in a Neuropathic Pain Rat Model.

In our first attempt to image $Na_V$ expression, [18F]benzamide-STX microPET-MRI has been performed on a Sprague-Dawley rat that had sustained a Spared Nerve Injury (SNI), a widely-accepted model of neuropathic pain that involves ligation of 2 out of the 3 major branches of the sciatic nerve. (see, e.g., Decosterd, I. and C. J. Woolf, *Spared nerve injury: an animal model of persistent peripheral neuropathic pain*. Pain, 2000. 87(2): p. 149-58.) Since MRI offers exquisite soft tissue contrast and delineation of the peripheral nerves and dorsal root ganglia, we utilized a 7.0T small animal MRI available in our Small Animal Imaging Facility to generate an anatomic map of the sciatic nerves. In this particular example, the animal was imaged at 5 weeks post-injury, well after post-surgical inflammation has resolved. Under isoflurane anesthesia, the animal was rigidly positioned into a transferable holder, which supports a mouse or rat in a fixed position for whole body studies with both imaging modalities: microPET (GEHC (Suisna) eXplore Vista microPET) and microMRI (General Electric “MicroSigna 7.0” 7T). Following intravenous injection of 500 μCi [18F]benzamide-STX, the rat was imaged with microPET for 10 minutes (20 minutes after radiotracer injection) and then transferred to microMRI. Fiducial markers fixed on the holder as well as the animal make possible the co-registration of the microPET and microMRI data sets. The mouse holder does not interfere with the imaging process in any of the discussed imaging modalities.

Figure 18:
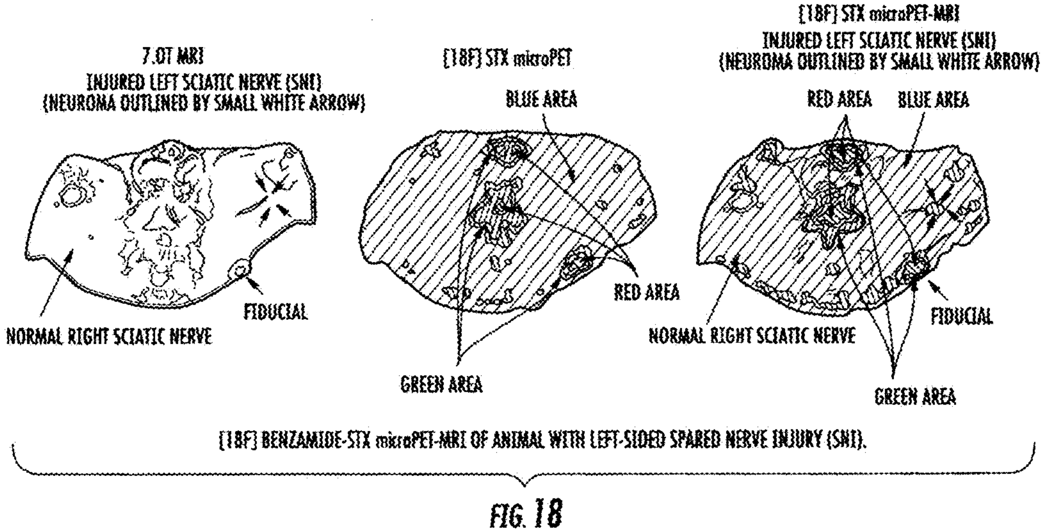
FIG. 18 provides microPET-MRI images (PET: positron emission tomography; MRI: magnetic resonance imaging) of a rat with left-sided spared nerve injury (SNI).

In FIG. 18, a transverse microMR image (left image) through the thigh at the level of the left sciatic nerve injury shows an enlarged neuroma while the right sciatic nerve is normal in size and caliber. The central image is of the [18F]benzamide-STX microPET experiment, obtained at the same view, and the right figure shows the two co-registered images. Increased microPET signal is seen in the vicinity of the neuroma created by the SNI. By comparison, no signal is seen in the right nerve. Additionally, in the soft tissues near the injured nerve, there also appears increased radiotracer uptake (red arrows). The finding of activity outside of the neuroma may be telling of other changes related to the nerve injury, which may be an important part of the pain experience. The finding of [18F]STX activity outside of the neuroma suggest that $Na_V$ upregulation of non-injured tissues in the vicinity of the nerve injury may also be an important factor in the development of chronic pain syndromes. Others have observed such pro-nociceptive events in both injured and neighboring non-injured nerves. The upregulation β2 subunits of $Na_V$, for example, has been observed in the cell body and peripheral axons of both the injured tibial and common peroneal nerves as well as the non-injured sural nerve in the SNI model. (see, e.g., Pertin, M., et al., Upregulation of the voltage-gated sodium channel beta2 subunit in neuropathic pain models: characterization of expression in injured and non-injured primary sensory neurons. J Neurosci, 2005. 25(47): p. 10970-80.) Further, the observation of increased [18F]benzamide-STX in the nerve injury correlates with the animal’s increased allodynia in the left hindpaw, as determined by von Frey tests. MicroPET signal in the center and anterior aspect of the image is related to excreted radiotracer material.

Example 6

Figure 19:
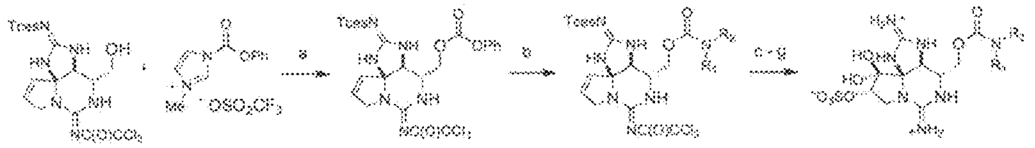
FIG. 19 illustrates a synthetic scheme for synthesis of saxitoxin analogues such as gonyautoxins. Conditions: (a) $CH_2Cl_2$, 70%; (b) $HNR_1R_2$, $CH_2Cl_2$; (c) 4 mol % $OsO_4$, NMO, THF/$H_2O$; (d) PhC(O)CN, DMAP, $CH_2Cl_2$, −78° C.; (e) Des-Martin periodinane, $CH_2Cl_2$; (f) $H_2$, Pd/C, $CF_3CO_2H$, MeOH; then $NH_3$, MeOH; (g) DMF.$SO_3$, 2,4,6-tri-t-butylpyrimidine, DMF.

We provide herein a modified preparative route that gives access to derivatives of the C11-sulfated $Na^+$ channel blockers, known as gonyautoxins. Our procedure begins with alcohol 1 (FIG. 19), which may be prepared as outlined in Example 2. Treatment of this material with the electrophilic imidazolium salt 2 gives rise to a phenyl carbonate. Primary and secondary amines may be added to this species, producing carbamate-modified intermediates such as 4a and 4b. A sequence of five steps completes the synthesis of N21-substituted analogues of STX/GTX, such as 5a and 5b.

Experimental Protocols and Characterization Data:

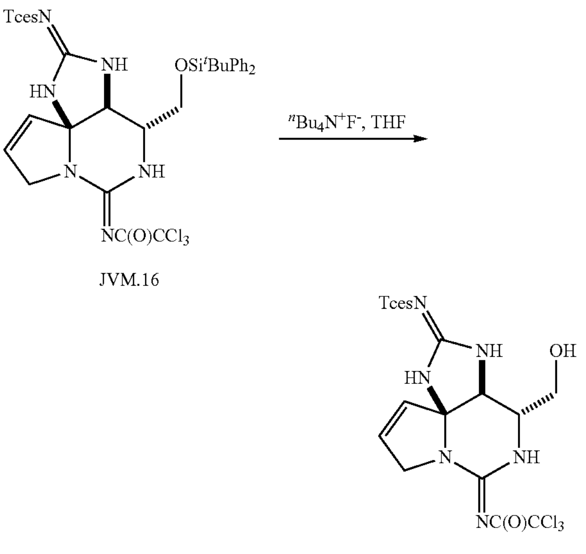

JVM.16

JVM.21

To a solution of olefin JVM.16 (792 mg, 0.97 mmol) in 20 mL of THF cooled to −78° C. was added tetrabutylammonium fluoride (1.16 mL of a 1.0 M solution in THF, 1.16 mmol, 1.2 equiv). The mixture was warmed to 0° C. and stirred at this temperature for 20 min Following this time, the reaction was quenched by the addition of 20.0 mL of saturated aqueous $NH_4Cl$. The contents were diluted with 40 mL of EtOAc and transferred to a separatory funnel. The organic layer was collected and the aqueous phase was extracted with 3×40 mL of EtOAc. The combined organic extracts were dried over $MgSO_4$ and concentrated under reduced pressure. Purification by chromatography on silica gel (2:1→1:2 hexanes/EtOAc) afforded JVM.21 as a white solid (424 mg, 75%). TLC $R_f$=0.33 (1:2 hexanes/EtOAc); $^1H$ NMR ($CD_3OD$, 400 MHz) δ 6.28 (ddd, 1H, J=6.2, 2.0, 2.0 Hz), 6.08 (ddd, 1H, J=6.2, 2.2, 2.2 Hz), 4.67 (d, 1H, J=11.2 Hz), 4.64 (d, 1H, J=11.2 Hz), 4.43 (m, 2H), 4.35 (d, 1H, J=2.8 Hz), 3.69-3.63 (m, 2H), 3.57 (dd, 1H, J=12.4, 8.4 Hz) ppm; $^{13}C$ NMR ($CDCl_3$, 125 MHz) δ 172.3, 159.4, 157.9, 130.9, 127.4, 96.5, 94.1, 83.1, 78.4, 61.7, 55.5, 55.2, 54.5 ppm; IR (thin film) n 3289, 1616, 1562, 1379, 1175, 905, 841, 730 $cm^{-1}$.

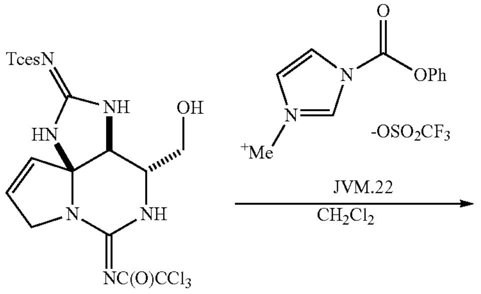

JVM.21

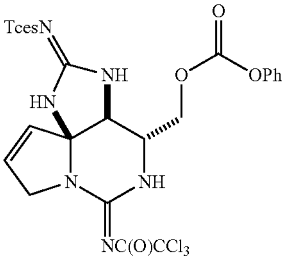

JVM.23

To a solution of alcohol JVM.21 (424 mg, 0.73 mmol) in 7.3 mL of THF was added JVM.22 (297 mg, 0.84 mmol, 1.2 equiv). The reaction was stirred for 23 h at room temperature and then quenched by the addition of 15 mL of saturated aqueous $NaHCO_3$ and 20 mL of EtOAc. The contents were transferred to a separatory funnel and the organic phase was collected. The aqueous phase was extracted with 2×10 mL of EtOAc. The combined organic extracts were dried over $MgSO_4$ and concentrated under reduced pressure. Purification by chromatography on silica gel (hexanes→1:2 hexanes/EtOAc) afforded JVM.23 as a white solid (357 mg, 70%). TLC $R_f$=0.52 (1:2 hexanes/EtOAc); $^1H$ NMR ($CD_2Cl_2$, 400 MHz) δ 9.57 (d, 1H, J=2.8 Hz), 7.44-7.39 (m, 2H), 7.32-7.27 (m, 1H), 7.20-7.16 (m, 2H), 6.36 (ddd, 1H, J=6.2, 2.0, 2.0 Hz), 6.04 (ddd, 1H, J=6.2, 2.2, 2.2 Hz), 4.64 (s, 2H), 4.60-4.54 (m, 1H), 4.51-4.45 (m, 1H), 4.40 (dd, 1H, J=12, 6.4 Hz), 4.35 (d, 1H, J=3.2 Hz), 4.31 (dd, 1H, J=12.0, 5.2 Hz), 3.98-3.93 (m, 1H) ppm.

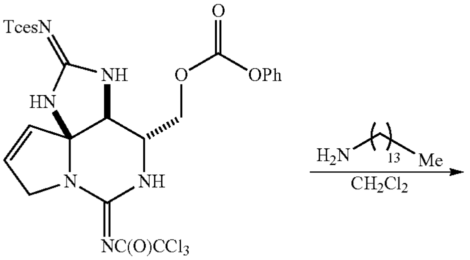

JVM.23

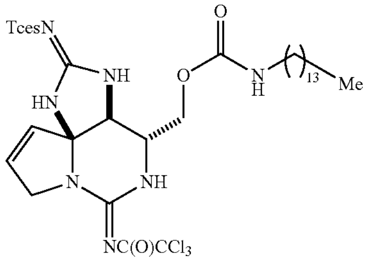

JVM.24

To a solution of JVM.23 (53 mg, 0.075 mmol)) dissolved in 750 μL of $CH_2Cl_2$ was added tetradecylamine (150 μL of a 1.0 M solution in $CH_2Cl_2$, 0.15 mmol, 2.0 equiv). The reaction was stirred for 5 h at room temperature and then additional tetradecylamine was added (300 μL of a 1.0 M solution in $CH_2Cl_2$). The reaction was stirred for an additional 12 h at room temperature and then transferred directly to a column of silica gel. Purification of the residue by chromatography on silica gel (hexanes→1:2 hexanes/EtOAc) afforded JVM.24 as a white solid (22.1 mg, 36%). TLC $R_f$=0.53 (1:2 hexanes/EtOAc); $^1H$ NMR ($CD_2Cl_2$, 400 MHz) δ 9.61 (br s, 1H), 6.33 (ddd, 1H, J=6.2, 2.0, 2.0 Hz), 6.05 (ddd, 1H, J=6.2, 2.2, 2.2 Hz), 4.98 (dd, 1H, J=5.6, 5.6 Hz), 4.67-4.60 (m, 3H), 4.48-4.41 (m, 1H), 4.23 (dd, 1H, J=12.0, 7.2 Hz), 4.16 (dd, 1H, J=12.0, 5.2 Hz), 4.11 (d, 1H, J=4.0 Hz), 3.87-3.81 (m, 1H), 3.17-3.10 (m, 2H), 1.53-1.44 (m, 2H), 1.27 (br s, 22H), 0.89 (t, 3H, J=6.8 Hz) ppm.

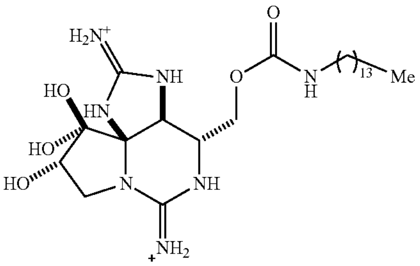

JVM.25

$^1H$ NMR ($CD_3OD$, 500 MHz) δ 4.81 (s, 1H), 4.41 (dd, 1H, J=7.0, 7.0 Hz), 4.31 (dd, 1H, J=11.5, 9.5 Hz), 4.06 (dd, 1H, J=11.5, 4.5 Hz), 3.79-3.72 (m, 1H), 3.22 (dd, 1H, J=10.5, 7.0 Hz), 3.18-3.06 (m, 2H), 1.51 (br s, 2H), 1.31 (br s, 22H), 0.92 (t, 3H, J=7.0 Hz) ppm.

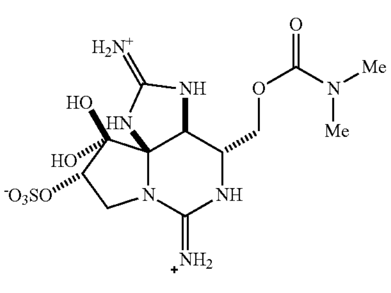

JVM.26
$IC_{50}$~15 nM
against $Na_V1.4$ $^1H$ NMR ($D_2O$, 500 MHz) δ 4.83 (dd, 1H, J=7.5, 7.5 Hz), 4.63 (d, 1H, J=0.5 Hz), 4.19 (dd, 1H, J=11.5, 9.0 Hz), 4.04 (dd, 1H, J=10.5, 8.0 Hz), 3.96 (dd, 1H, J=11.5, 5.5 Hz), 3.72 (dd, 1H, J=5.0, 9.0 Hz), 3.44 (dd, 1H, J=11.0, 7.5 Hz), 2.79 (s, 3H), 2.74 (s, 3H) ppm.

Example 7

Figure 20:
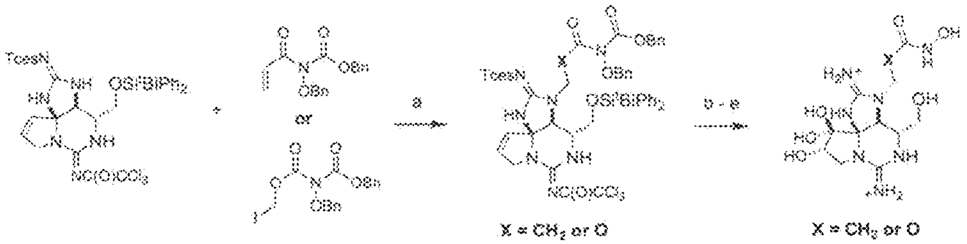
FIG. 20 illustrates a synthetic scheme for synthesis of saxitoxin analogues such as R7-substituted STX analogues. Conditions: (a) $(Me_2N)_2C{=}N^tBu$ or $(Me_2N)_2C{=}NH$, $CH_2Cl_2$; (b) 4 mol % $OsO_4$, NMO, THF/$H_2O$; (c) PhC(O)CN, DMAP, $CH_2Cl_2$, −78° C.; (d) Dess-Martin periodinane, $CH_2Cl_2$; (e) $H_2$, Pd/C, $CF_3CO_2H$, MeOH; then $NH_3$, MeOH.

We have developed conditions which allow for the selective functionalization of the R7 position of the bis-guanidinium framework depicted in Structure A. Most frequently, these species are prepared from the olefins JVM.16 or JVM.17, described in Example 2, but can also be prepared from related structures. Selective functionalization of the R7 position is possible using a variety of electrophiles, and the products can be converted to fully deprotected STX analogues through a series of steps following the general pathway described for the preparation of 11β-OH-STX (Example 2). FIG. 20 illustrates the installation of acrylate and hydroxymethylene moieties at this position, and elaboration of the products to R7-substituted analogues of STX. FIG. 21 illustrates a series of N7-substituted STX analogues that have been prepared by related methods and electrophysiological data regarding the ability of such compounds to inhibit a mammalian sodium channel isoform, $Na_V1.4$.

Experimental Protocols and Characterization Data:

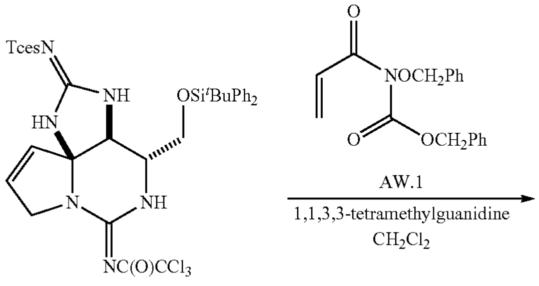

JVM.16

-continued

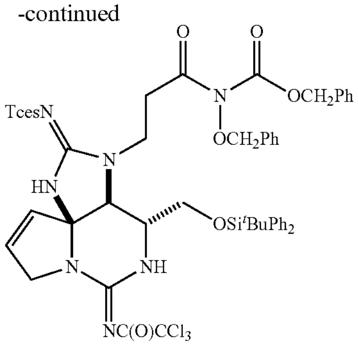

AW.2

To a solution of JVM.16 (100 mg, 0.12 mmol) in 3.5 mL of $CH_2Cl_2$ was added 1,1,3,3-tetramethylguanidine (15 μL, 0.12 mmol, 1.0 equiv). The mixture was stirred for 1 min, and then AW.1 (65 mg, 0.21 mmol, 1.7 equiv) was added. After 1.5 h the reaction was filtered through a short plug of silica gel. Purification by chromatography on silica gel (2:1 hexanes/EtOAc) afforded AW.2 as a white solid (98 mg, 71%). TLC $R_f$=0.31 (2:1 hexanes/EtOAc); $^1H$ NMR ($CDCl_3$, 500 MHz) δ 9.52 (s, 1H), 7.65-7.60 (m, 4H), 7.50-7.27 (m, 16H), 6.91 (s, 1H), 6.12 (d, 1H, J=6.0 Hz), 5.82 (d, 1H, J=6.0 Hz), 5.30 (s, 2H), 4.91 (q, 2H, J=10.0 Hz), 4.63 (s, 2H), 4.45-4.39 (m, 2H), 4.21-4.15 (m, 1H), 3.92-3.85 (m, 1H), 3.80-3.74 (br s, 1H), 3.67-3.58 (m, 2H), 3.43-3.35 (m, 1H), 3.33-3.26 (m, 1H), 3.06-2.99 (m, 1H), 1.06 (s, 9H) ppm; $^{13}C$ NMR ($CDCl_3$, 125 MHz) δ 172.7, 169.9, 160.1, 155.7, 152.5, 135.8, 134.5, 133.8, 132.1, 130.8, 130.5, 130.1, 129.3, 128.8, 128.3, 94.2, 81.5, 78.6, 69.8, 63.7, 62.5, 53.7, 53.3, 47.0, 37.7, 35.9, 31.9, 27.0, 22.9, 19.3, 14.4 ppm.

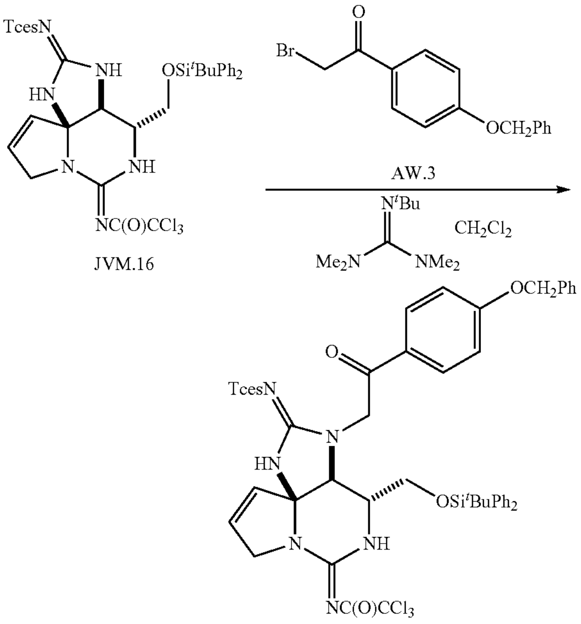

JVM.16

AW.4

To a solution of JVM.16 (30 mg, 0.037 mmol) in 1.48 mL of $CH_2Cl_2$ cooled to −20° C. were sequentially added 2-tert-butyl-1,1,3,3-tetramethylguanidine (7.1 μL, 0.037 mmol, 1.0 equiv) and AW.3 (13.5 mg, 0.044 mmol, 1.2 equiv). The reaction mixture was warmed slowly to room temperature and stirred for 1.5 h. Following this time the contents were applied directly to a column of silica gel. Purification by chromatography on silica gel (2.5:1 hexanes/EtOAc) afforded AW.4 (30 mg, 0.029 mmol, 78%). TLC $R_f$=0.36 (2:1 hexanes/EtOAc); $^1$H NMR ($CDCl_3$, 500 MHz) δ 9.46 (s, 1H), 7.90 (d, 2H, J=9.0 Hz), 7.55-7.32 (m, 15H), 7.19 (s, 1H), 7.08 (d, 2H, J=9.0 Hz), 6.21-6.14 (m, 2H), 5.24-5.14 (m, 3H), 4.60-4.49 (m, 3H), 4.43 (br s, 1H), 4.38-4.23 (m, 2H), 3.74 (br s, 1H), 3.60 (dd, 1H, J=10.5, 6.5 Hz), 3.47 (dd, 1H, J=10.5, 7.5 Hz), 0.93 (s, 9H) ppm.

AW.3

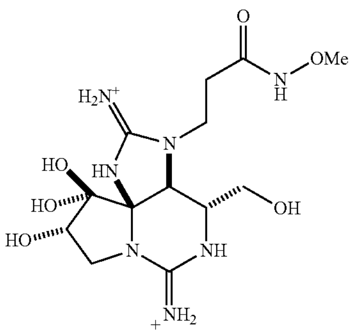

$^1$H NMR ($D_2O$, 500 MHz) δ 4.72 (s, 1H), 4.39 (dd, 1H, J=7.0, 7.0 Hz), 3.97 (dd, 1H, J=10.0, 8.0 Hz), 3.86-3.78 (m, 1H), 3.77-3.63 (m, 4H), 3.70 (s, 3H), 2.40 (dd, 1H, J=10.5, 7.0 Hz), 2.55-2.49 (m, 2H) ppm.

Example 8

We have developed conditions that make possible the selective functionalization of the R3 position of the bis-guanidinium framework depicted in Structure A. FIG. 22 illustrates the installation of an n-propyl group at this position, and elaboration of the product to a C10-substituted analogue of GTX 3. Similar conditions have also been developed for the installation of a methyl group at C10, and are provided in the experimental section of this example directly below. These procedures demonstrate our ability to prepare R3-substituted analogues of STX and GTX.

Experimental Protocols and Characterization Data:

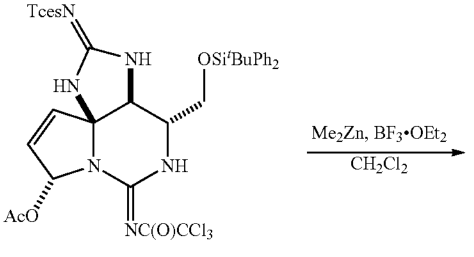

JVM.15

-continued

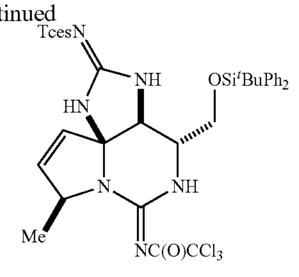

JW.1

To a solution of JVM.15 (20 mg, 0.023 mmol) in 460 μL of $CH_2Cl_2$ cooled to −78° C. were sequentially added $Me_2Zn$ (57 μL of a 2.0 M solution in toluene, 0.11 mmol, 5.0 equiv) and $BF_3$.$OEt_2$ (6.61 μL, 0.053 mmol, 2.3 equiv). The reaction contents were allowed to slowly warm to room temperature and stirred for 1 h. Following this time, the reaction was quenched by the addition of 1 mL of saturated aqueous $NaHCO_3$. The resulting biphasic solution was stirred vigorously for 15 min. The mixture was then diluted with 3 mL of EtOAc and transferred to a separatory funnel. The organic layer was collected and the aqueous phase was extracted with 2×3 mL of EtOAc. The combined organic extracts were dried over $MgSO_4$ and concentrated under reduced pressure. Purification of the isolated material by chromatography on silica gel (gradient elution: hexanes→2:1 hexanes/EtOAc) afforded olefin JW.1 as a white solid (11.7 mg, 61%). $^1$H NMR ($CD_3OD$, 500 MHz) δ 7.64-7.59 (m, 4H), 7.47-7.36 (m, 6H), 6.13 (dd, 1H, J=7.5, 2.5 Hz), 5.89 (dd, 1H, J=7.5, 2.0 Hz), 4.64 (d, 1H, J=13.5 Hz), 4.60 (d, J=13.5 Hz), 4.58-4.51 (m, 1H), 4.20 (d, 1H, J=3.5 Hz), 3.79-3.75 (m, 1H), 3.72 (dd, 1H, J=13.0, 5.5 Hz), 3.52 (dd, 1H, J=13.0, 10.0 Hz), 1.55 (d, 3H, J=8.5 Hz), 1.01 (s, 9H) ppm.

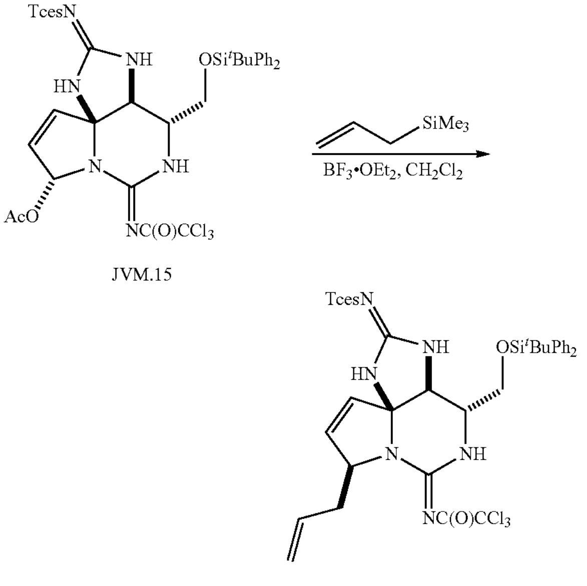

JVM.15

JW.2

To a solution of JVM.15 (150 mg, 0.171 mmol) in 3.42 mL of $CH_2Cl_2$ cooled to −78° C. were sequentially added allyltrimethylsilane (136 μL, 0.86 mmol, 5.0 equiv) and $BF_3$.$OEt_2$ (50 μL, 0.39 mmol, 2.3 equiv). The reaction contents were allowed to slowly warm to room temperature and stirred for 1.5 h. Following this time, the reaction was quenched by the addition of 5 mL of saturated aqueous $NaHCO_3$. The resulting biphasic solution was stirred vigorously for 15 min. The mixture was then diluted with 15 mL of EtOAc and transferred to a separatory funnel. The organic layer was collected and the aqueous phase was extracted with 2×10 mL of EtOAc. The combined organic extracts were dried over $MgSO_4$ and concentrated under reduced pressure. Purification of the isolated material by chromatography on silica gel (gradient elution: hexanes→2:1 hexanes/EtOAc) afforded olefin JW.2 as a white solid (102 mg, 70%). $^1H$ NMR ($CD_3OD$, 500 MHz) δ 7.64-7.58 (m, 4H), 7.46-7.36 (m, 6H), 6.15 (dd, 1H, J=7.5, 2.5 Hz), 5.95 (dd, 1H, J=7.5, 2.5 Hz), 5.84-5.72 (m, 1H), 5.23-5.14 (m, 2H), 4.61 (d, 2H, J=1.0 Hz), 4.53-4.48 (m, 1H), 4.19 (d, 1H, J=3.5 Hz), 3.78-3.70 (m, 2H), 3.54-3.48 (m, 1H), 2.99-2.92 (m, 1H), 2.68 (ddd, 1H, J=17.0, 10.5, 10.5 Hz), 1.02 (s, 9H) ppm; $^{13}C$ NMR ($CD_3OD$, 125 MHz) δ 171.5, 160.2, 157.9, 135.7, 135.6, 134.1, 133.5, 132.4, 132.3, 130.1, 127.9, 127.5, 119.0, 94.3, 82.0, 78.2, 67.1, 63.8, 58.0, 55.8, 47.4, 26.3, 18.8 ppm.

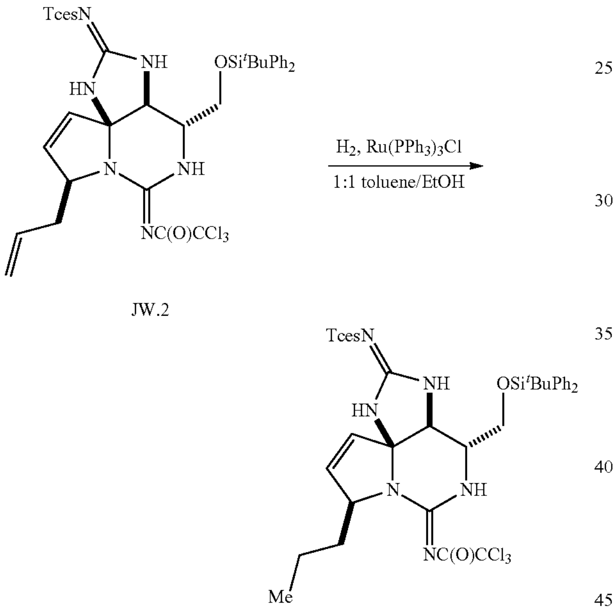

JW.2

JW.3

To solid JW.2 (102 mg, 0.12 mmol) and $Ru(PPh_3)_3Cl$ (1.1 mg, 0.0002 mmol, 0.01 equiv) under an atmosphere of $N_2$ was added 12 mL of deoxygenated 1:1 toluene/EtOH. An atmosphere of hydrogen was introduced and the reaction mixture was stirred at room temperature for 1 h. Following this time, the reaction was concentrated under reduced pressure. Purification of the isolated material by chromatography on silica gel (gradient elution: hexanes→2:1 hexanes/EtOAc) afforded JW.3 as a white solid (96 mg, 94%). $^1H$ NMR ($CD_3OD$, 500 MHz) δ 7.67-7.62 (m, 4H), 7.49-7.40 (m, 6H), 6.28 (dd, 1H, J=6.0, 2.0 Hz), 5.95 (dd, 1H, J=6.0, 2.0 Hz), 4.67 (d, 1H, 11.5 Hz), 4.64 (d, 1H, 11.5 Hz), 4.52-4.48 (m, 1H), 4.21 (d, 1H, J=3.0 Hz), 3.82-3.76 (m, 2H), 3.55 (dd, 1H, J=9.5, 7.0 Hz), 2.45-2.36 (m, 1H), 1.71-1.62 (m, 1H), 1.53-1.36 (m, 2H), 1.05 (s, 9H), 1.01 (t, 3H, J=7.5 Hz) ppm; $^{13}C$ NMR ($CD_3OD$, 125 MHz) δ 171.4, 160.0, 158.2, 135.7, 135.6, 134.8, 132.4, 130.0, 127.93, 127.90, 127.0, 81.6, 78.3, 67.2, 63.9, 58.2, 55.6, 37.0, 26.3, 19.1, 18.8, 13.3, 0.3 ppm.

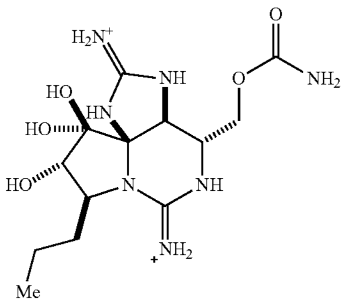

JW.4

$^1H$ NMR ($D_2O$, 500 MHz) δ 4.35 (d, 1H, J=6.0 Hz), 4.16-4.13 (m, 2H), 4.04 (d, 1H, J=6.0 Hz), 3.67-3.62 (m, 1H), 3.53-3.48 (m, 1H) 1.80 (br s, 1H), 1.63 (br s, 1H), 1.35 (br s, 2H), 0.86 (t, 3H, J=7.5 Hz) ppm.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of “about 0.1% to about 5%” should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term “about” can include traditional rounding according to significant figures of the numerical value. In addition, the phrase “about ‘x’ to ‘y’” includes “about ‘x’ to about ‘y’”.

Many variations and modifications may be made to the above-described embodiments. All such modifications and variations are intended to be included herein within the scope of this disclosure and protected by the following claims.

What is claimed is:

1. A compound having structure A shown below, a stereoisomer thereof, a tautomer thereof, or a pharmaceutically acceptable salt of any of the above:

Structure A

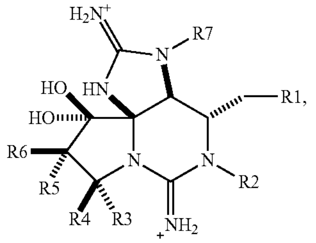

wherein R1 is selected from the group consisting of: halogen, alkyl, alkenyl, alkynyl, alkoxy, cyano, haloalkyl, dihaloalkyl, trihaloalkyl, perhaloalkyl, perfluoroalkyl, cycloalkyl, (cycloalkyl)alkyl, substituted phenyl, (substituted phenyl)alkyl, aryl, heteroaryl, heterocyclic, heterocyclo, alkanoyl, (monosubstituted) amino, protected (monosubstituted)amino, (disubstituted)amino, heteroaryl(alkyl), nitro, oxa, oxo, sulfonyl, sulfonamido, sulfone, —$OR_A$, ═O, —C(═O)$R_A$, —OC(═O)$OR_A$, —$CO_2R_A$, —CN, —SCN, —$SR_A$, —$SOR_A$, —$SO_2R_A$, —$NO_2$, —N$(R_A)_2$, —NHC(O)$R_A$, and —C$(R_A)_3$, wherein each occurrence of $R_A$ can be independently hydrogen, halogen, alkyl, alkenyl, alkynyl, alkoxy, cyano, haloalkyl, perhaloalkyl, cycloalkyl, (cycloalkyl)alkyl, substituted phenyl, (substituted phenyl)alkyl, aryl, heteroaryl, heterocyclic, heterocyclo, alkanoyl, (monosubstituted) amino, protected (monosubstituted)amino, (disubstituted)amino, heteroaryl(alkyl), nitro, oxa, oxo, sulfonyl, sulfonamido, and sulfone;

wherein R2 is hydrogen;

wherein R3 is hydrogen or alkyl;

wherein R4 is hydrogen or alkyl;

wherein R5 is hydrogen or —$OSO_3^-$;

wherein R6 is hydrogen or —$OSO_3^-$; and wherein R7 is hydrogen, with the proviso that the compound having structure A is not a compound selected from dcSTX, dcGTX2 and dcGTX3.

2. The compound of claim 1 having structure B shown below, a stereoisomer thereof, a tautomer thereof, or a pharmaceutically acceptable salt of any of the above:

Structure B

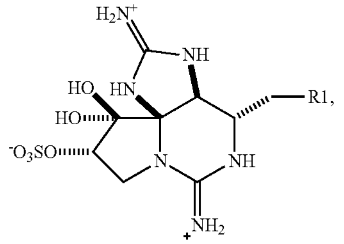

3. The compound of claim 1 having structure C shown below, a tautomer thereof, or a pharmaceutically acceptable salt of any of the above:

Structure C

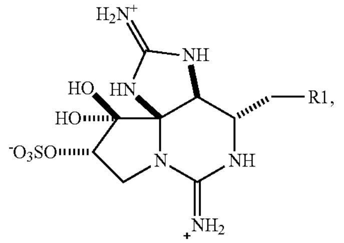

4. The compound of claim 1 linked to a label selected from the group consisting of: a radioisotope, a fluorescent moiety, a chemiluminescent moiety, an enzyme, an antibody, an antibody fragment, a magnetic particle, and a quantum dot.

5. A pharmaceutical composition comprising the compound of claim 1, or a stereoisomer thereof, a tautomer thereof, or a pharmaceutically acceptable salt of any of the above.

6. The compound of claim 1, wherein said compound has a longer duration of action of anesthetic effect than saxitoxin.

7. The compound of claim 1, wherein R1 is hydroxyl, alkoxyl, cyano, heteroaryl, (monosubstituted)amino, protected (monosubstituted)amino, (disubstituted)amino, —$OR_A$, ═O, —OC(═O)$OR_A$, —CN, —SCN, —$SR_A$, —$SOR_A$, —$SO_2R_A$, —$NO_2$, —N$(R_A)_2$, or —NHC(O)$R_A$, wherein each occurrence of $R_A$ can be independently a group such as hydrogen, halogen, alkyl, alkenyl, alkynyl, alkoxy, cyano, haloalkyl, perhaloalkyl, cycloalkyl, (cycloalkyl)alkyl, substituted phenyl, (substituted phenyl)alkyl, aryl, heteroaryl, heterocyclic, heterocyclo, alkanoyl, (monosubstituted)amino, protected (monosubstituted)amino, (disubstituted)amino, heteroaryl(alkyl), nitro, oxa, oxo, sulfonyl, sulfonamido, or sulfone.

8. The compound of claim 1, wherein $R_A$ is independently hydrogen, methyl, isopropyl, tetradecyl, or any one of the following:

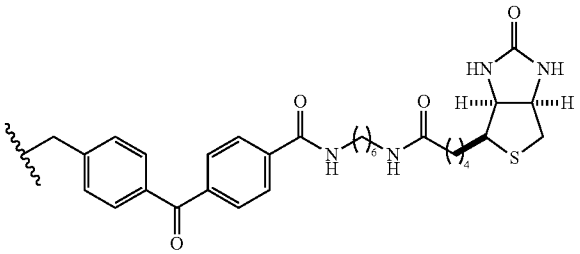

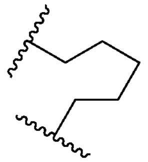

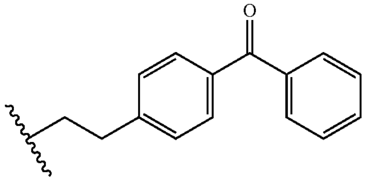

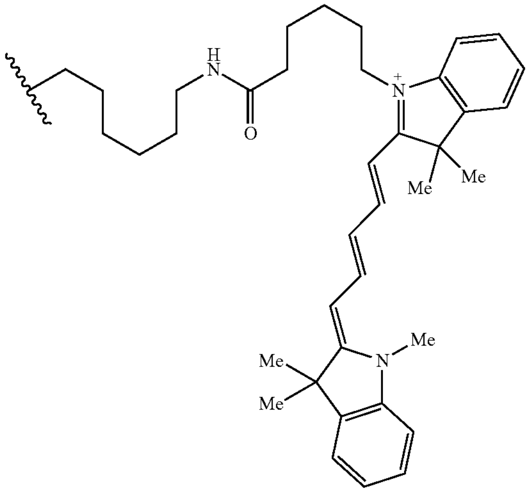

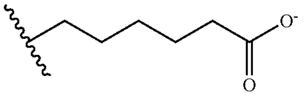

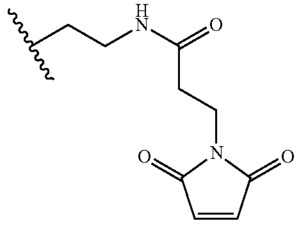

-continued
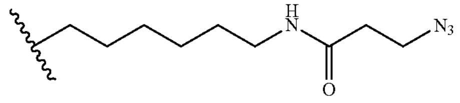
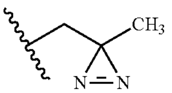
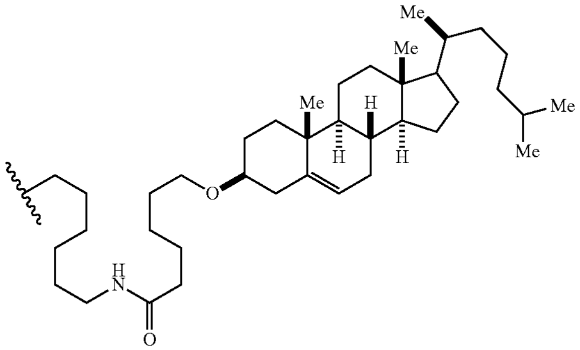
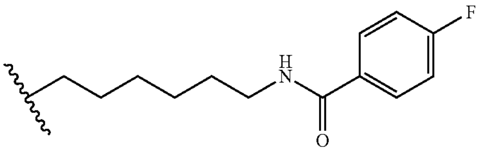
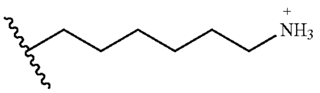
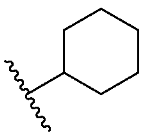
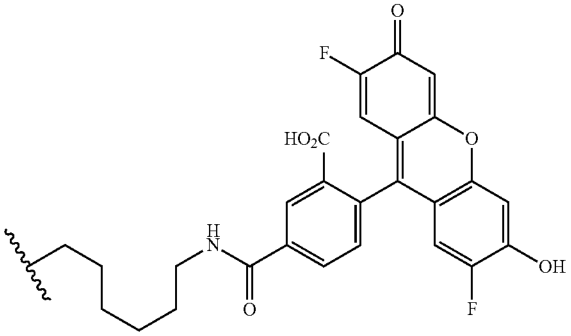
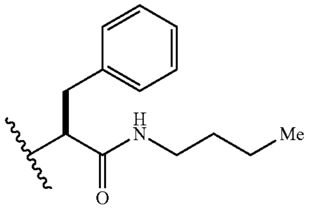
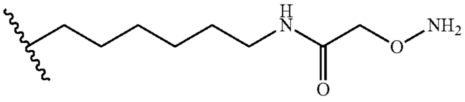
-continued
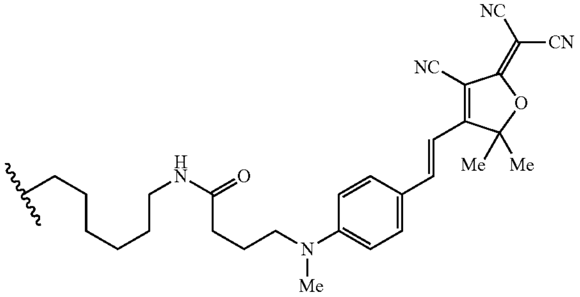
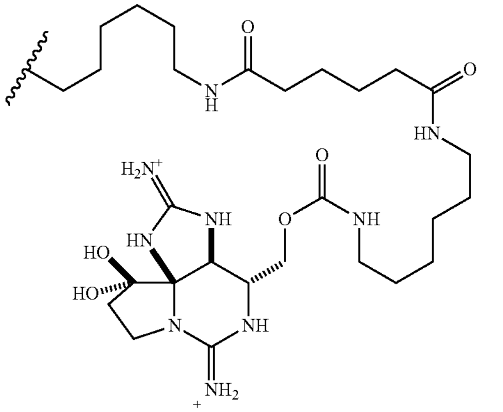
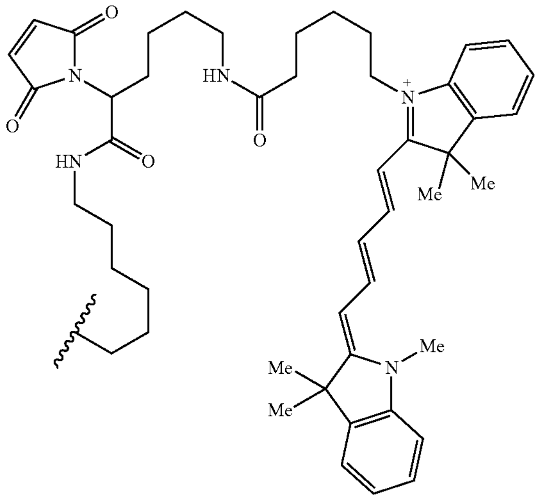
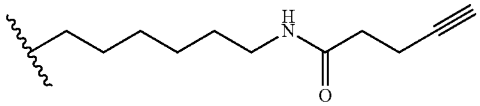
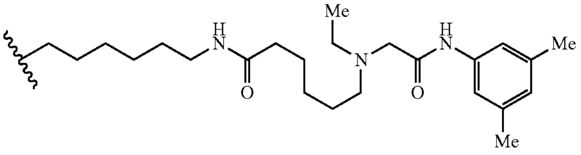

-continued
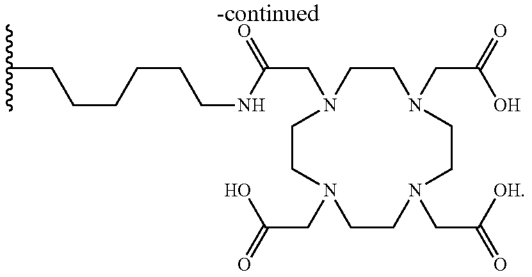
* * * * *